(12) United States Patent
Cheng

(10) Patent No.: US 12,697,096 B2
(45) Date of Patent: Aug. 4, 2026

(54) SYSTEMS AND METHODS FOR ULTRASOUND EXAMINATION

(71) Applicant: WUHAN UNITED IMAGING HEALTHCARE CO., LTD., Wuhan (CN)

(72) Inventor: Li Cheng, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 52 days.

(21) Appl. No.: 18/391,621

(22) Filed: Dec. 20, 2023

(65) Prior Publication Data

US 2024/0197292 A1      Jun. 20, 2024

(30) Foreign Application Priority Data

Dec. 20, 2022   (CN) .......................... 202211645966.1
Dec. 28, 2022   (CN) .......................... 202211692928.1

(51) Int. Cl.
*A61B 8/00*                (2006.01)

(52) U.S. Cl.
CPC .............. *A61B 8/463* (2013.01); *A61B 8/465* (2013.01)

(58) Field of Classification Search
CPC ......... A61B 8/463; A61B 8/465; A61B 8/467; A61B 8/469; A61B 8/585; A61B 8/54
See application file for complete search history.

(56) References Cited

U.S. PATENT DOCUMENTS

| | | | | |
|---|---|---|---|---|
| 5,161,535 | A | 11/1992 | Short et al. | |
| 5,897,503 | A * | 4/1999 | Lyon ........................ | A61B 8/00 |
| | | | | 600/459 |
| 8,038,619 | B2 * | 10/2011 | Steinbacher ........... | A61B 8/467 |
| | | | | 600/459 |
| 11,564,861 | B1 * | 1/2023 | Gaines ................... | A61H 23/04 |
| 2004/0015080 | A1 * | 1/2004 | Kelly ..................... | A61B 8/406 |
| | | | | 600/459 |
| 2007/0122021 | A1 * | 5/2007 | Zingaretti ............. | G06T 7/0014 |
| | | | | 382/132 |
| 2008/0247618 | A1 * | 10/2008 | Laine .................... | G06T 7/0012 |
| | | | | 382/128 |

(Continued)

FOREIGN PATENT DOCUMENTS

| | | |
|---|---|---|
| CN | 102440803 A | 5/2012 |
| CN | 110801248 A | 2/2020 |

(Continued)

OTHER PUBLICATIONS

First Office Action in Chinese Application No. 202211645966.1 mailed on Jul. 25, 2025, 15 pages.

*Primary Examiner* — Sanjay Cattungal

(74) *Attorney, Agent, or Firm* — METIS IP LLC

(57)                ABSTRACT

The present disclosure provides a method for ultrasound examination. The method may include obtaining, from a user terminal, an operation instruction of an operator input via a user interface implemented on the user terminal, the operation instruction for confirming or adjusting an initial adjustment mode of the scanning parameter; determining, based on the operation instruction of the operator, a target adjustment mode of the scanning parameter; and configuring the ultrasound imaging scanner based on the target adjustment mode.

20 Claims, 17 Drawing Sheets

<u>100</u>

(56) References Cited

U.S. PATENT DOCUMENTS

| | | | | |
|---|---|---|---|---|
| 2009/0012401 A1* | 1/2009 | Steinbacher | A61B 8/467 | 600/459 |
| 2010/0249598 A1* | 9/2010 | Smith | A61B 8/4455 | 600/459 |
| 2010/0324423 A1* | 12/2010 | El-Aklouk | A61B 8/4488 | 600/444 |
| 2011/0074244 A1* | 3/2011 | Osawa | B06B 1/0622 | 310/318 |
| 2011/0082369 A1* | 4/2011 | Mohr | A61B 1/043 | 600/431 |
| 2011/0087107 A1* | 4/2011 | Lindekugel | A61B 8/4455 | 600/459 |
| 2011/0313293 A1* | 12/2011 | Lindekugel | A61B 10/00 | 600/459 |
| 2012/0165679 A1* | 6/2012 | Orome | A61B 5/150748 | 600/461 |
| 2012/0179044 A1* | 7/2012 | Chiang | A61B 8/14 | 600/467 |
| 2012/0289836 A1* | 11/2012 | Ukimura | A61B 8/14 | 600/463 |
| 2013/0338503 A1* | 12/2013 | Cohen | A61B 8/4411 | 600/443 |
| 2013/0338508 A1* | 12/2013 | Nakamura | A61B 8/4494 | 600/459 |
| 2014/0031694 A1* | 1/2014 | Solek | A61B 8/4427 | 600/459 |
| 2014/0066779 A1* | 3/2014 | Nakanishi | A61B 8/4444 | 600/459 |
| 2014/0180116 A1* | 6/2014 | Lindekugel | A61B 8/4455 | 600/459 |
| 2014/0276069 A1* | 9/2014 | Amble | A61B 8/4488 | 600/447 |
| 2014/0376793 A1* | 12/2014 | Lee | G16H 50/20 | 382/131 |
| 2015/0359520 A1* | 12/2015 | Shan | A61B 8/0858 | 600/443 |
| 2016/0026894 A1* | 1/2016 | Nagase | A61B 8/463 | 600/443 |
| 2017/0328751 A1* | 11/2017 | Lemke | G01H 9/00 | |
| 2020/0163654 A1* | 5/2020 | Satir | A61B 8/58 | |
| 2021/0059639 A1* | 3/2021 | Howell | A61B 8/4444 | |
| 2021/0212668 A1* | 7/2021 | Li | G01S 17/66 | |
| 2022/0071593 A1* | 3/2022 | Tran | A61B 8/085 | |

FOREIGN PATENT DOCUMENTS

| | | | |
|---|---|---|---|
| CN | 105997141 B | | 4/2020 |
| CN | 113197595 A | | 8/2021 |
| CN | 113367723 A | | 9/2021 |
| CN | 114176631 A | | 3/2022 |
| JP | 2003240698 A | | 8/2003 |
| WO | 2018120840 A1 | | 7/2018 |
| WO | 2020082235 A1 | | 4/2020 |

* cited by examiner

<u>100</u>

300

400

Classifying multiple scanning parameters into multiple groups based on feature information of each of the multiple scanning parameters    — 410

Determining an adjustment mode for scanning parameters in the same group based on the feature information    — 420

| 610 Auto Optimization | ROI Res Add To Zoom | 660 Wide View   1   2   4 |
| --- | --- | --- |
| 620 uClean   −   1   + | 640 Tint Map   −   2   + | 670 Layout   1   2   4 |
| 630 TGC | 650 Rotate   0   90   180   270 | 680 Sight range   Up   Down |

710

900

1100

Determining multiple candidate configurations of the workbench interface ⟋1110

In response to receiving a configuration request instruction of an operator, providing one or more candidate configurations to the user interface and determining a target configuration of the workbench interface based on the one or more candidate configurations ⟋1120

<u>1600</u>

Obtaining an operation instruction of a user input via a user interface implemented on a user terminal from the user terminal ⌐1610

Based on the operation instruction of the operator, determining a target configuration of a workbench interface ⌐1620

Configuring the ultrasound imaging scanner based on the target adjustment mode ⌐1630

Mid to late pregnancy
ul 8-4

Mid to late pregnancy
uVC 6-2

Fetal heart rate
uC 6-1

Mid to late pregnancy
uT 8-3

Gynaecology
uT 8-3

Abdominal routine

Abdominal penetration

Abdominal kidneys

Abdominal blood
vessel

C6-1

2300

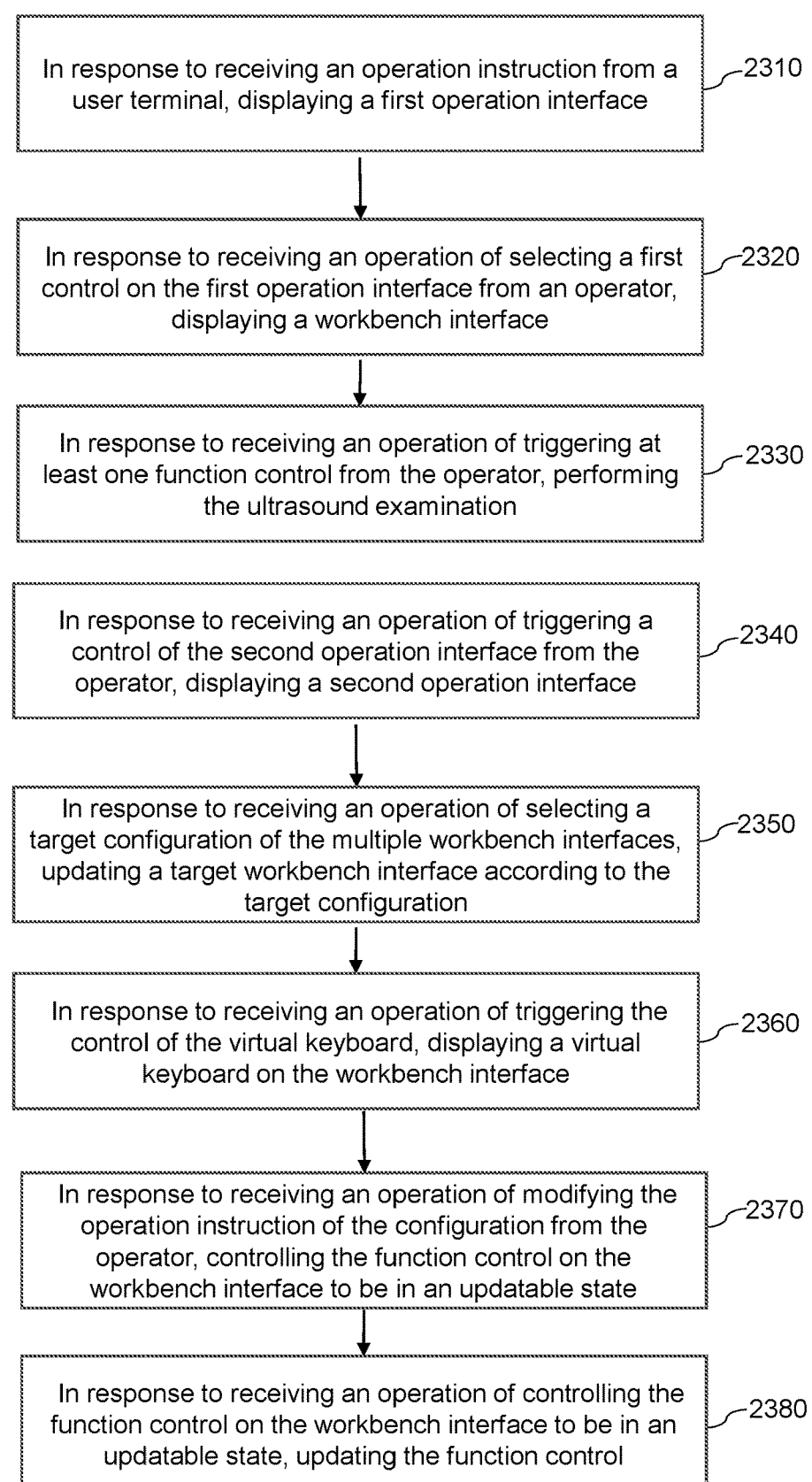

In response to receiving an operation instruction from a user terminal, displaying a first operation interface ⟋2310

In response to receiving an operation of selecting a first control on the first operation interface from an operator, displaying a workbench interface ⟋2320

In response to receiving an operation of triggering at least one function control from the operator, performing the ultrasound examination ⟋2330

In response to receiving an operation of triggering a control of the second operation interface from the operator, displaying a second operation interface ⟋2340

In response to receiving an operation of selecting a target configuration of the multiple workbench interfaces, updating a target workbench interface according to the target configuration ⟋2350

In response to receiving an operation of triggering the control of the virtual keyboard, displaying a virtual keyboard on the workbench interface ⟋2360

In response to receiving an operation of modifying the operation instruction of the configuration from the operator, controlling the function control on the workbench interface to be in an updatable state ⟋2370

In response to receiving an operation of controlling the function control on the workbench interface to be in an updatable state, updating the function control ⟋2380

FIG. 23

SYSTEMS AND METHODS FOR ULTRASOUND EXAMINATION

CROSS-REFERENCE TO RELATED APPLICATIONS

This application claims priority to the Chinese Patent Application No. 202211692928.1, filed on Dec. 28, 2022 and the Chinese Patent Application No. 202211645966.1, filed on Dec. 20, 2022 the contents of each of which are hereby incorporated by reference.

TECHNICAL FIELD

The present disclosure relates to a medical technology field, in particular, relates to systems and methods for ultrasound examination.

BACKGROUND

Ultrasound examination is configured to display a tissue structure and blood flow of a scanning subject in different visualization modes by processing various echo information generated by ultrasound within the scanning subject. The ultrasound examination is widely used in a field of medical technology due to non-invasive and radiation free.

During the ultrasound examination, a large number of scanning parameters need to be adjusted. For example, when performing an examination for different parts of a same subject or for different subjects, operators need to adjust a larger quantity of scanning parameters. The operators may need to find a position for adjusting the larger quantity of scanning parameters with time and effort, which can greatly affect the inspection efficiency of ultrasound scanning.

SUMMARY

In an aspect of the present disclosure, a system is provided. The system may include at least one storage medium including a set of instructions; at least one processor in communication with the at least one storage medium, wherein when executing the set of instructions, the at least one processor may be directed to cause the system to perform operations including: obtaining feature information of each of at least a portion of multiple scanning parameters; determining a target configuration of an adjustment mode of each of at least a portion of the multiple scanning parameters based on the feature information of each of at least a portion of the multiple scanning parameters, wherein the target configuration of the adjustment mode of the scanning parameter may include at least one of a type or an arrangement of the adjustment mode on a user interface; and configuring an ultrasound imaging device based on the target configuration.

In another aspect of the present disclosure, a system is provided. The system may include at least one storage medium including a set of instructions; at least one processor in communication with the at least one storage medium, wherein when executing the set of instructions, the at least one processor may be directed to cause the system to perform operations including: obtaining, from a user terminal, an operation instruction of an operator input via a user interface implemented on the user terminal, the operation instruction being for configuring an adjustment mode of a scanning parameter of an ultrasound imaging device; determining, based on the operation instruction of the operator, a target configuration of the adjustment mode of the scanning parameter, wherein the target configuration of the adjustment mode of the scanning parameter may include at least one of a type or an arrangement of the adjustment mode on the user interface; and configuring the ultrasound imaging device based on the target configuration.

In another aspect of the present disclosure, a system is provided. The system may include an ultrasound imaging device; and a user terminal in communication with the ultrasound imaging device, the user terminal including a user interface implemented on a touch screen, the user interface representing one of a workbench interface in a target configuration or a function module interface in response to receipt of an operation instruction for entering inputted by an operator, wherein the target configuration of the workbench interface includes one or more functions of each of different function modules of the ultrasound imaging device.

BRIEF DESCRIPTION OF THE DRAWINGS

This specification will be further illustrated by way of exemplary embodiments, which will be described in detail with the accompanying drawings. These examples are non-limiting, and in these examples, the same number indicates the same structure, wherein:

FIG. 23 is a flowchart illustrating an exemplary process for ultrasound examination according to some embodiments of the present disclosure.

DETAILED DESCRIPTION

Figure 1:
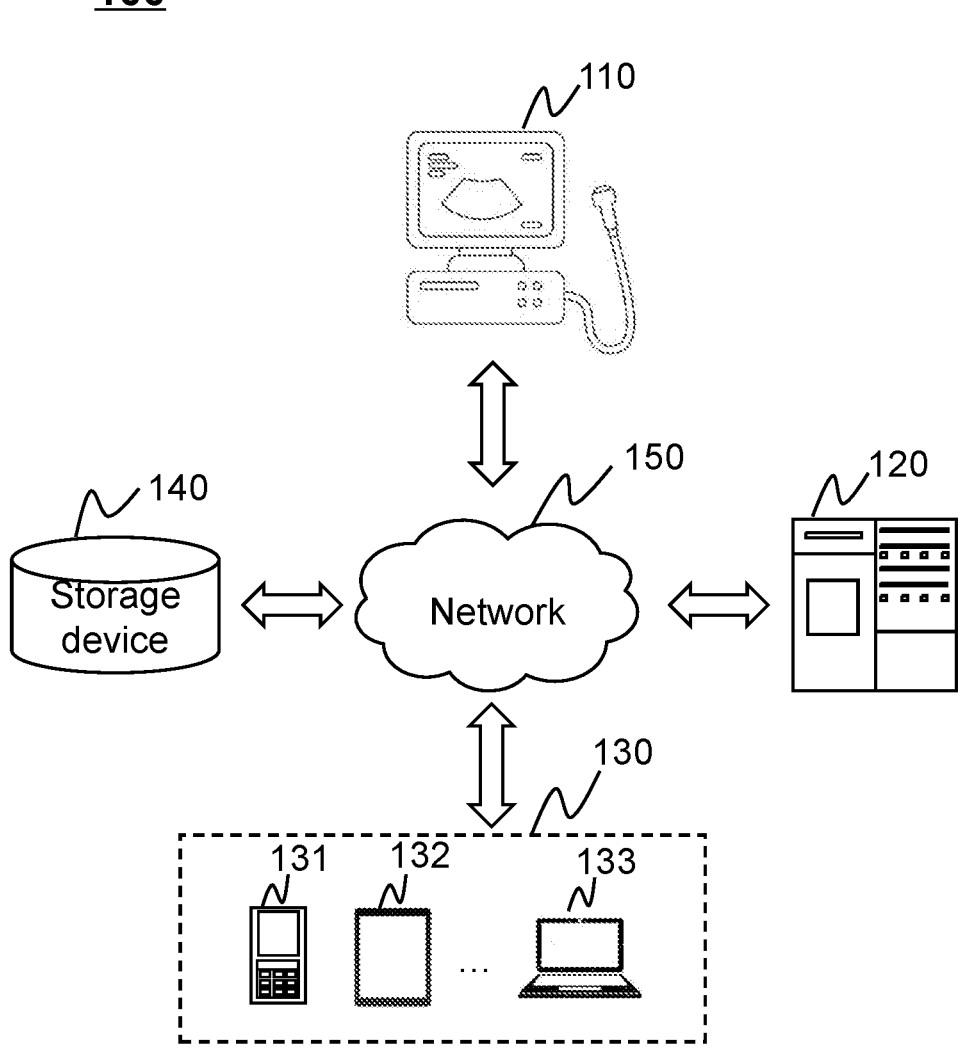
FIG. 1 is a schematic diagram illustrating an exemplary application scenario of an ultrasound imaging system according to some embodiments of the present disclosure.

In order to more clearly illustrate the technical solutions of the embodiments of the present specification, the following briefly introduces the drawings that need to be used in the description of the embodiments. Apparently, the accompanying drawings in the following description are only some examples or embodiments of this specification, and those skilled in the art can also apply this specification to other similar scenarios. Unless obviously obtained from the context or the context illustrates otherwise, the same numeral in the drawings refers to the same structure or operation.

It should be understood that "system," "device," "unit" and/or "module" as used herein is a method for distinguishing different components, elements, parts, parts or assemblies of different levels. However, the words may be replaced by other expressions if other words can achieve the same purpose.

Based on the following description of the accompanying drawings, these and other features, as well as the functions and operating methods of related structural elements, as well as component combinations and manufacturing economics, can become more apparent in this specification, all of which form a part of this specification. However, it should be understood that the accompanying drawings are for illustrative and descriptive purposes only and are not intended to limit the scope of the present disclosure. It should be understood that the attached drawings are not drawn to scale.

As indicated in the specification and claims, the terms "a," "an," "an" and/or "the" are not specific to the singular and may include the plural unless the context clearly indicates an exception. Generally speaking, the terms "comprising" and "comprising" only suggest the inclusion of clearly identified steps and elements, and these steps and elements do not constitute an exclusive list, and the method or device may also contain other steps or elements.

Flowcharts are used in the present disclosure to illustrate the operation performed by the system according to the embodiment of the present disclosure. It should be understood that the preceding or subsequent operations are not necessarily performed accurately in sequence. Instead, the steps may be processed in reverse order or simultaneously. At the same time, other operations may add to these procedures, or remove one or more operations from these procedures.

FIG. 1 is a schematic diagram illustrating an exemplary application scenario of an ultrasound imaging system according to some embodiments of the present disclosure.

As shown in FIG. 1, in some embodiments, an application scenario 100 of an ultrasound imaging system may include an ultrasound imaging scanner 110, a processing device 120, a user terminal 130, a storage device 140, and a network 150.

The ultrasound imaging scanner 110 may be configured to examine a target subject or a part of the target subject and generate an image related to the target subject or an image related to a part of the target subject (e.g., scanning images). In some embodiments, the target subject may include a body, a substance, or any combination thereof. In some embodiments, the target subject may include specific parts of a body, such as the head, the chest, the abdomen, or any combination thereof. In some embodiments, the target subject may include specific organs, such as the heart, the esophagus, the trachea, the bronchus, the stomach, the gallbladder, the small intestine, the colon, the bladder, the ureter, the uterus, a fallopian tube, or the like. In some embodiments, the target subject may include a human or other medical experimental subjects (e.g., an experimental mice and other animals).

In some embodiments, the ultrasound imaging scanner 110 may include a one-dimensional (1D) ultrasound imaging scanner, a two-dimensional (2D) ultrasound imaging scanner, a three-dimensional (3D) ultrasound imaging scanner, a four-dimensional (4D) ultrasound imaging scanner, or the like. In some embodiments, the ultrasound imaging scanner 110 may include a handheld ultrasound imaging scanner, an automated ultrasound imaging scanner, or the like. In some embodiments, the ultrasound imaging scanner 110 may include a medical ultrasound imaging scanner (e.g., an ultrasound imaging scanner used in hospitals), a household ultrasound imaging scanner (e.g., a small pregnancy examination ultrasound imaging scanner), a portable ultrasound imaging scanner (e.g., a handheld ultrasound imaging scanner that is easy to carry for travel), or the like.

In some embodiments, the ultrasound imaging scanner 110 may include an output device (e.g., a display, a printer, etc.), an input device (e.g., a touch screen, a mouse, a keyboard, a physical button, etc.), a processor (e.g., a processing device 120), a storage device (e.g., a storage device 140), or the like. In some embodiments, the ultrasound imaging scanner 110 may include a touch screen configured to display an image and/or adjust scanning parameters associated with the scanning or examination of the subject. In some embodiments, the ultrasound imaging scanner 110 may include a control panel configured to adjust one or more scanning parameters, and the control panel may include one or more physical adjustment buttons (e.g., a key, a knob, a trackball, etc.). In some embodiments, the ultrasound imaging scanner 110 may include a probe configured to obtain an image of the target subject. For example, the probe may emit and receive ultrasonic waves. The probe may perform an electroacoustic signal conversion. The probe may convert an electrical signal sent by a host to an ultrasound signal and emit the ultrasound signal to the subject. The probe may convert an ultrasound signal received and reflected from the subject (e.g., tissue organs) to an electrical signal. The electrical signal received by the probe may be processed by the ultrasound imaging scanner and further displayed on a display of the host (e.g., the processing device 120) and/or the user terminal 130.

The processing device 120 may process data and/or information obtained from the ultrasound imaging scanner 110, the user terminal 130, and/or the storage device 140. For example, the processing device 120 may process information generated by the ultrasound imaging scanner 110 to obtain a scanning image and/or generate a scanning report (also referred to as an examination report). As another example, the processing device 120 may configure the ultrasound imaging scanner 110 automatically or according to operator inputs. The configuration of the ultrasound imaging scanner 110 may include a target configuration of an adjustment mode of at least one scanning parameter of the ultrasound imaging scanner 110 for performing the ultrasound scanning, a configuration of a workbench interface, or the like, or a combination thereof. For example, the processing device 120 may obtain, from a user terminal, an operation instruction of a user input via a user interface implemented on the user terminal, and the operation instruction may be for configuring an adjustment mode of a scanning parameter of an ultrasound imaging scanner. The processing device 120 may determine, based on the operation instruction of the operator, a target configuration of the adjustment mode of the scanning parameter, and the target configuration of the adjustment mode of the scanning parameter may include at least one of a type or an arrangement of the adjustment mode on the user interface. The processing device 120 may configure the ultrasound imaging scanner based on the target configuration.

As a further example, the processing device 120 may obtain an operation instruction of a user input via a user interface implemented on the user terminal 130, and the operation instruction may be configured to configure a workbench interface. The processing device 120 may determine a target configuration of the workbench interface based on the operation instruction of the operator input, and configure the ultrasound imaging scanner 110 based on the target configuration. As a further example, the processor may obtain at least one personalized information of an operator, historical operations of the operator, a clinical scene, personalized information of a scanning subject, or a scanning mode of the scanning subject obtained in the storage device 140 and/or the ultrasound imaging scanner 110 based on the network 150. The processor may determine the target configuration based on the obtained information.

In some embodiments, the processing device 120 may be a single server or a servers group. The servers group may be centralized or distributed. In some embodiments, the processing device 120 may be local or remote. For example, the processing device 120 may access information and/or data from the ultrasound imaging scanner 110, the user terminal 130, and/or the storage device 140 through the network 150. As another example, the processing device 120 may connect to the ultrasound imaging scanner 110, the user terminal 130, and/or the storage device 140 directly to access information and/or data. In some embodiments, the processing device 120 may be implemented on a cloud platform. For example, the cloud platform may include one or several combinations of a private cloud, a public cloud, a hybrid cloud, a community cloud, a distributed cloud, a cross cloud, a multi cloud, or the like. In some embodiments, the processing device 120 may be part of ultrasound imaging scanner 110.

The user terminal 130 may include one or more user terminal devices or software used by the operator. The operator refers to a manager or operator (e.g., different doctors) of the ultrasound imaging system. In some embodiments, the user terminal 130 may interact with other components in the application scenario 100 of the ultrasound imaging system through the network 150. For example, the user terminal 130 may send personalized information of the scanning subject to the ultrasound imaging scanner 110 through the network 150. As another example, the user terminal 130 may also receive a scanning image obtained by the ultrasound imaging scanner 110 through the network 150, and/or display the scanning image for analysis and confirmation.

In some embodiments, the user terminal may communicate with the ultrasound imaging scanner and the at least one processor. The user terminal 130 may include a user interface on the touch screen. The user interface may be configured to achieve an interaction between the user and the ultrasound imaging system and/or between the ultrasound imaging scanner and the ultrasound imaging system. The user interface may be an interface displayed on the touch screen of the ultrasound imaging scanner, and the user interface may include a workbench interface and/or function modules. The operators may input the operation instruction through the user interface. The user interface may display the scanning image for user confirmation. In some embodiments, the user terminal 130 may include a mobile device 131, a tablet 132, a laptop 133, or any combination thereof. The mobile device 131 may include smart home devices, wearable devices, mobile devices, virtual reality devices, augmented reality devices, or any combination thereof. In some embodiments, the wearable devices may include bracelets, footwear, glasses, helmets, watches, clothing, backpacks, smart accessories, or any combination thereof. In some embodiments, the mobile devices may include mobile phones, personal digital assistants (PDAs), gaming devices, navigation devices, POS devices, laptops, tablets, desktops, or any combination thereof.

The storage device 140 may store data (e.g., the scanning image of the target subject, historical operation events of the scanning parameter of the operator, feature information of the scanning parameter, adjustment processes and/or controls for the scanning parameter configuration, layout of the display interface, the scanning report, etc.), instructions, and/or any other information. In some embodiments, the storage device 140 may store data obtained from the ultrasound imaging scanner 110, the user terminal 130, and/or the processing device 120. For example, the storage device 140 may store the patient information, the scanning image, and the scanning report obtained from ultrasound imaging scanner 110. As another example, the storage device 140 may store an adjustment process and/or adjustment control for the scanning parameter configuration obtained from the processing device 120. In some embodiments, the storage device 140 may store data and/or instructions that the processing device 120 can execute and/or use to execute the exemplary processes described in the present disclosure.

In some embodiments, the storage device 140 may include a large capacity memory, a removable memory, a volatile read write memory, a read-only memory (ROM), or any combination thereof. The large capacity storage may include disks, optical disks, solid-state drives, mobile storage, or the like. The removable storage may include flash drives, floppy disks, optical disks, storage cards, ZIP disks, magnetic tapes, or the like. In some embodiments, the storage device 140 may be implemented through the cloud platform described in the present disclosure. In some embodiments, the storage device 140 may be part of ultrasound imaging scanner 110.

In some embodiments, the storage device 140 may be connected to the network 150 to achieve communication with one or more components (e.g., the ultrasound imaging scanner 110, the processing device 120, the user terminal 130, etc.) in the application scenario 100 of the ultrasound imaging system. The one or more components in the application scenario 100 of the ultrasound imaging system may read the data and/or instructions from the storage device 140 through the network 150. In some embodiments, the storage device 140 may be part of processing device 120 or independent of the processing device 120, which is connected to the processing device 120 directly or indirectly.

The network 150 may include any suitable network that can facilitate the exchange of information and/or data for the application scenario 100 of the ultrasound imaging system. In some embodiments, the one or more components of the application scenario 100 of the ultrasound imaging system (e.g., the ultrasound imaging scanner 110, the processing device 120, the user terminal 130, the storage device 140, etc.) may exchange information and/or data with the one or more components of the application scenario 100 of the ultrasound imaging system through the network 150. In some embodiments, the network 150 may include public networks (e.g., Internet), private networks (e.g., local area networks (LANs), wide area networks (WANs), etc.), wired networks (e.g., Ethernet), wireless networks (e.g., 802.11 networks, wireless Wi Fi networks, etc.), cellular networks (e.g., Long Term Evolution (LTE) networks), frame relay networks, virtual private networks (VPNs), satellite networks, telephone networks, routers, hubs, server computers, or any combination thereof. In some embodiments, the network 150 may include one or more network access points. For example, the network 150 may include wired and/or wireless network access points, such as a base station and/or an internet switching point, and the one or more components of the application scenario 100 of the ultrasound imaging system may connect to the network 150 to exchange the data and/or information based on the access points.

It should be noted that the above description of the ultrasound imaging system is only for illustrative purposes and is not intended to limit the scope of the present disclosure. For those skilled in the field, various variants and modifications can be made according to the specification. However, the changes and modifications are not outside the scope of the present disclosure. For example, the ultrasound imaging scanner 110, the processing device 120, and the user terminal 130 may share a storage device 140 or have their own storage devices.

Figure 2:
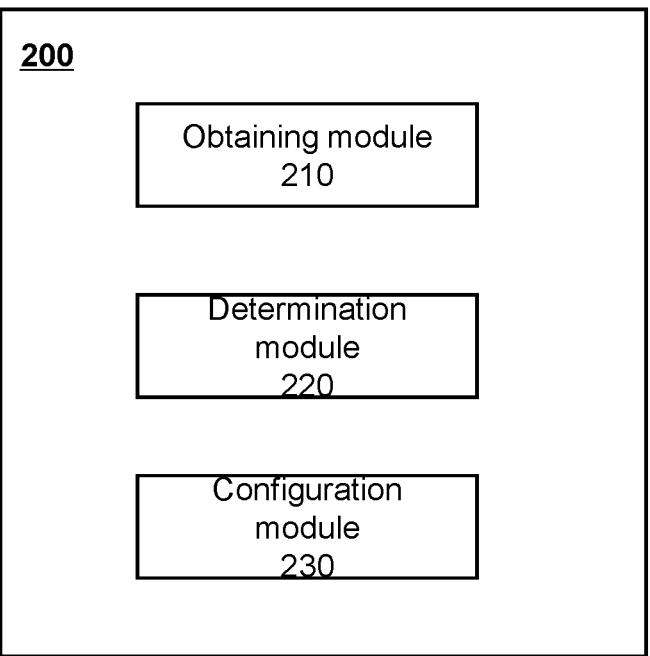
FIG. 2 is a schematic diagram illustrating exemplary modules of an ultrasound imaging system according to some embodiments of the present disclosure.

FIG. 2 is a schematic diagram illustrating exemplary modules of an ultrasound imaging system according to some embodiments of the present disclosure.

In some embodiments, the ultrasound imaging system may include at least one storage medium including a set of instructions; at least one processor in communication with the at least one storage medium, wherein when executing the set of instructions, the at least one processor is directed to cause the ultrasound imaging system to perform operations. The storage medium may store computer instructions, after the computer reads the computer instructions in the storage medium, the computer may operate the ultrasound examination process described in any embodiment. More specific storage medium may include but are not limited to portable disks, hard disks, random access memory, read-only memory, erasable programmable read-only memory, optical storage devices, magnetic memory devices, or any suitable combination of the above.

As shown in FIG. 2, in some embodiments, the ultrasound imaging system 200 may include an obtaining module 210, a determination module 220, and a configuration module 230. In some embodiments, the obtaining module 210, the determination module 220, and the configuration module 230 may be components in the processing device 120.

The obtaining module 210 may be configured to obtain data, instruction, or the like. In some embodiments, the obtaining module 210 may be configured to obtain an operation instruction of a user input via a user interface implemented on the user terminal from the user terminal, and the operation instruction may be configured for configuring the ultrasound imaging scanner. For example, the operation instruction may be configured to configure an adjustment mode of a scanning parameter of the ultrasound imaging scanner. As another example, the operation instruction may be configured to configure a workbench interface for the ultrasound imaging scanner.

The determination module 220 may be configured to determine the data, instruction, or the like. In some embodiments, the determination module 220 may be configured to determine a target configuration of the scanning parameter based on the operation instruction of the operator. The target configuration of the adjustment mode of the scanning parameter may include at least one of a type or an arrangement of adjustment mode on the user interface.

In some embodiments, the determination module 220 may be configured to determine a target configuration of the workbench interface based on the operation instruction of the operator. The user interface may represent a workbench interface and/or at least one of the one or more function module interfaces of the ultrasound imaging scanner. The target configuration may include types of one or more functions of each of the different function modules of the ultrasound imaging scanner and/or arrangement of the one or more functions included the workbench interface.

The configuration module 230 may be configured to configure the ultrasound imaging scanner. In some embodiments, the configuration module 230 may configure the ultrasound imaging scanner based on the target configuration of the scanning parameter and/or the target configuration of the workbench interface. More description of the obtaining module 210, the determination module 220, and the configuration module 230 may be found elsewhere in the present disclosure.

It should be noted that the above description of the ultrasound imaging system 200 is for illustrative purposes only and is not intended to limit the scope of the present disclosure. For those skilled in the field, various variants and modifications can be made according to the present disclosure. However, these changes and modifications are not outside the scope of the present disclosure.

Figure 3:
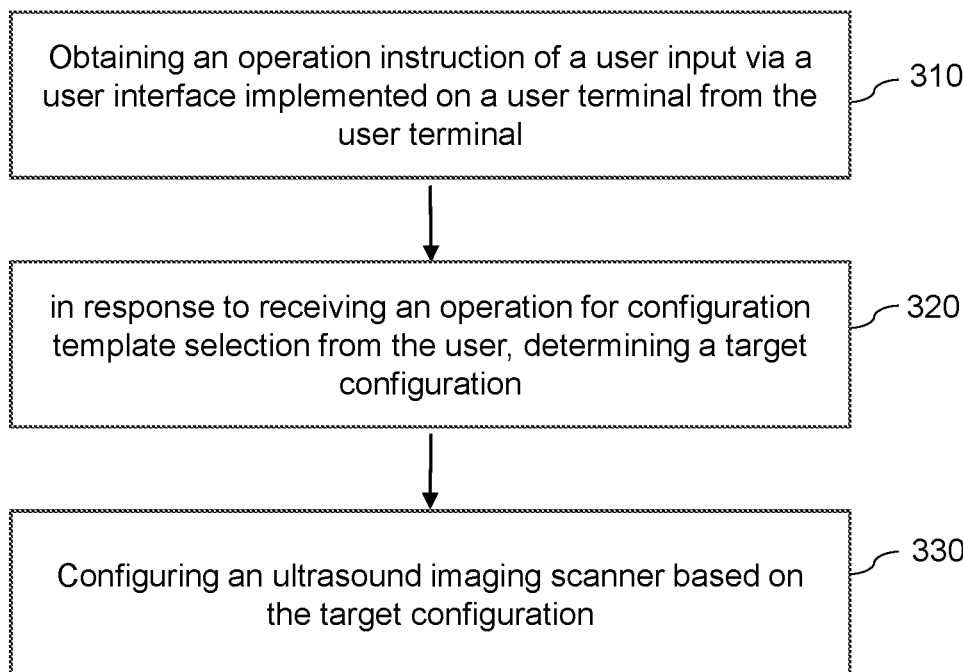
FIG. 3 is a schematic diagram illustrating an exemplary process of determining a target adjustment mode of a scanning parameter according to some embodiments of the present disclosure.

FIG. 3 is a schematic diagram illustrating an exemplary process of determining a target configuration of a scanning parameter according to some embodiments of the present disclosure.

In some embodiments, a process 300 may be executed by the processing device 120 or the ultrasound examination system 200. For example, the process 300 may be implemented as instructions (e.g., application programs) and stored in a memory such as the storage device 140 that can be accessed by the processing device 120. The processing device 120 may execute instructions, when executing the instructions, the processing device 120 may be configured to perform process 300. Process 300 presented below is illustrative. In some embodiments, the process may be accomplished by utilizing one or more undescribed additional operations and/or one or more undescribed operations. In addition, an operation sequence of the process 300 shown in FIG. 3 and described below is non-limited.

In some embodiments, the process 300 may be executed by a processing device (e.g., the processing device 120 or a processor that the ultrasound examination system 200 is implemented by). As shown in FIG. 3, the process 300 may include the following operations:

In 310, an operation instruction of a user input via a user interface implemented on a user terminal may be obtained from the user terminal.

More descriptions of the user terminal and the user interface may be found in FIG. 1 and related descriptions.

The operation instruction may include a computer instruction generated by the processing device in response to receipt of an operation behavior of an operator inputted through by the user via an input device (e.g., a mouse, a microphone, a touch screen, an image acquisition unit, etc.) of the user terminal. The operation behavior may be generated by at least a portion of an operator or user (e.g., a hand, the head, an eye, a finger, etc.) performing an action through the input device. For example, the operation behavior may include clicking a mouse, dragging the mouse, clicking a touch screen, keyboard input, voice input, eye tracking, or any combination thereof. The operation instruction may be configured to instruct a computer (e.g., the processing device 120, a processor in a user terminal, a processor in the ultrasound imaging scanner or system) to perform a function corresponding to the operation instruction. In some embodiments, the operation instruction may include a request (also referred to as a configuration request) for configuring the adjustment mode of the scanning parameter of the ultrasound imaging scanner. The processing device (e.g., the processing device 120 or a processor that the ultrasound examination system 200 is implemented by) may trigger the configuration of the adjustment mode of the scanning parameter of the ultrasound imaging scanner in response to receipt the operation instruction. In some embodiments, the operation instruction may include a request for selecting or adjusting the adjustment mode of the scanning parameter of the ultrasound imaging scanner. In some embodiments, the request for selecting or adjusting the adjustment mode of the scanning parameter of the ultrasound imaging scanner may include a target adjustment mode of the scanning parameter input by the operator, and the processing device may determine that the adjustment mode of the scanning parameters of the ultrasound imaging scanner corresponding to the operation instruction is the target probe-based adjustment mode inputted by the operator in response to receipt of the operation instruction. More descriptions of the adjustment mode of the scanning parameter may be found in operation 320 and related descriptions.

The scanning parameter may be used for the ultrasound examination performed by the ultrasound imaging scanner on a subject. In some embodiments, the scanning parameter of the ultrasound imaging scanner may include a depth, a gain, a scale, a dynamic range, an image storage, a freezing, a measurement, a harmonic, a frame rate, an auto optimization, a fusion imaging, a panoramic imaging, a spatial composition, a Gray Map/Color maps, a time gain compensation (TGC), a layout target range, a rotation, a wide view, an ROI res to zoom, a tint map, or the like.

In some embodiments, the operator may input the operation behavior via an input device (e.g., the user interface of the user terminal) and the input device may convert the operation behavior into the operation instruction and send the operation instruction to the processing device. The processing device may obtain the operation instruction of the operator input from the input device.

In 320, in response to receiving the operation instruction, a target configuration of the adjustment mode of the scanning parameter may be determined.

The target configuration refers to configuration information related to the adjustment mode of the scanning parameter used by the ultrasound imaging scanner. The adjustment mode of the scanning parameter may be defined by an entity (e.g., a key, a button, a knob, etc.) or a virtual subject (e.g., a virtual key, a control on a touch screen, etc.) operated by the operator to adjust the scanning parameter. In some embodiments, the target configuration may include at least one of a type or arrangement of the adjustment mode on a component of the ultrasound imaging scanner or system. The component of the ultrasound imaging scanner or system may include a probe, a control panel, a touch screen, etc., associated with the ultrasound imaging scanner. The arrangement of the adjustment mode may include a distribution position of the adjustment mode on the component of the ultrasound imaging scanner or system.

In some embodiments, the type of the adjustment mode of the scanning parameter may include a probe-based adjustment mode (also referred to as a probe-based adjustment mode), an adjustment mode implemented on a control panel of the ultrasound imaging scanner (also referred to as a control panel-based adjustment mode, an adjustment mode implemented on a touch screen of the ultrasound imaging scanner (also referred to as a touch screen-based adjustment mode, a voice-based adjustment mode, an EEG-based adjustment mode, an eye interaction-based adjustment mode, a gesture-based adjustment mode, etc.

The probe-based adjustment mode refers to a manner of adjusting the scanning parameter by operating an entity (e.g., a button, a key, a knob, a position, etc.) on the probe. For example, the scanning parameter may be adjusted by the operator double-clicking or clicking on a certain position of the probe. As a further example, a sensor may be configured in the probe to identify an operation of the operator inputted through the probe, such as picking up the probe, clicking or double-clicking on a shell of the probe, to input parameter adjustment instruction information to the ultrasound imaging scanner to achieve a corresponding parameter adjustment. The probe-based adjustment mode may further include a button-based adjustment mode, a knob-based adjustment mode, etc., according to different entities on the probe for adjusting the scanning parameter.

The control panel-based adjustment mode may be a manner of adjusting the scanning parameter by operating an entity such as a knob, a trackball, a button, etc., on the control panel. The entity (e.g., knob, a trackball, a button) on the control panel may be operated to increase or decrease the scanning parameter. For example, the button on the control panel may be set as different adjustment functions, such as increasing "+," and decreasing "−" on the control panel. The knob may be used to adjust the corresponding scanning parameter through rotation actions. For example, the clockwise rotation may be used to increase scanning parameter and the counterclockwise rotation may be used to decrease the scanning parameter. The trackball may be used to adjust the corresponding scanning parameter based on the movement of the trackball (e.g., the rotation). There may be a position mapping relationship between the movement of the trackball and a cursor in the display screen of the ultrasound imaging scanner, based on the position mapping relationship, as the trackball moves, the cursor may also move accordingly. For example, the operator may move the cursor by dragging the trackball, and adjust the ROI Res To Zoom of the ultrasound image based on a movement result of the cursor, such as zooming in or out. In some embodiments, the knob may include a fixed knob or a mode variable knob. The fixed knob refers to a knob used for adjusting only one scanning parameter. The mode variable knob refers to a knob used for adjusting more than one scanning parameter. For example, the same knob, which may adjust a scanning parameter-dynamic range in a mode B while adjust a scanning parameter-scale in mode C, may be the mode variable knob. The control panel-based adjustment mode may further include a button-based adjustment mode, a knob-based adjustment mode, a trackball-based adjustment mode, etc., according to different entities on the control panel for adjusting the scanning parameter.

The touch screen-based adjustment mode refers to a manner of adjusting a scanning parameter by operating an entity or virtual subject (e.g., a control, a virtual button) displayed on the touch screen with a finger or a touch screen tool (e.g., a stylus, touchable gloves, etc.). The touch screen-based adjustment mode may further include using an excitation type adjustment control, a switch type adjustment control, a tile type adjustment control, a gear adjustment control, and a sliding type adjustment control, etc.

The voice-based adjustment mode refers to a manner in which the operator adjusts the scanning parameter through voice control. For example, the operator may interact with the processing device through the voice, and the processing device may read keywords in the voice and adjust the scanning parameters accordingly.

The EEG-based adjustment mode refers to a manner for adjusting the scanning parameter according to operator side brain waves. For example, the processing device may directly obtain an EEG signal of the operator through an EEG device, and adjust the scanning parameter accordingly through the EEG signal.

The eye interaction-based adjustment mode refers to a manner adjusting the scanning parameter through eye interaction. For example, the processing device may obtain instruction information of a gaze point of the operator through an eye movement interaction, and adjust a scanning parameter based on the instruction information.

The gesture-based adjustment mode refers to a manner for adjusting the scanning parameter through interaction with gestures of the operator. In some embodiments, the gesture adjustment mode may be implemented through a display screen with a touch function (e.g., the touch screen) in the ultrasound imaging scanner. For example, the gesture adjustment mode may include adjusting the depth through sliding down or up, or adjusting the depth through sliding left and right. In some embodiments, the processing device may directly obtain a gesture of the operator through a finger sleeve device or an image acquisition device and adjust the scanning parameter accordingly through the gesture. A corresponding relationship between multiple gestures and different adjustments of different scanning parameters may be obtained. The processing device may determine the adjustment of the scanning parameter based on the obtained gesture and the corresponding relationship between multiple gestures and different adjustments of different scanning parameters. The gesture adjustment mode may help the operator pay more attention to the image and greatly increase the experience of parameter adjustment.

In some embodiments, the arrangement of adjustment mode on the user interface may include a target position of the adjustment mode in a parameter adjustment region on the user interface.

The parameter adjustment region refers to a region on the user interface configured to adjust the scanning parameter. More descriptions of the parameter adjustment region may be found in above descriptions of FIG. 3. The target position refers to a position of the adjustment mode of the scanning parameter in the parameter adjustment region.

In some embodiments, the processing device may determine the arrangement of one or more adjustment modes based on the feature information of the scanning parameter. For example, the processing device may display the adjustment control of the scanning parameter with a frequency greater than a frequency threshold on a homepage and/or target position of the parameter adjustment region in the target mode. In some embodiments, an adjustment control of the scanning parameter with an adjustment frequency greater than the frequency threshold and a count of adjustment levels greater than a quantity threshold may be displayed on the homepage and/or the target position of the parameter adjustment region in the target mode. The target position may be a position on the display interface that is easy to operate, such as a center position, a left side, a right side, or the like. In some embodiments, the target position may include a position on the homepage of the parameter adjustment region. In some embodiments, a size of the target location may be larger than other regions. In some embodiments, the target location may be customized and edited by the operator. More descriptions of the frequency threshold and the quantity threshold may be found in FIG. 4 and related descriptions.

In some embodiments, the operator may preset an arrangement of one or more scanning parameter adjustment modes manually.

In some embodiments, by determining the target position of the adjustment mode in the parameter adjustment region on the user interface, the operators may customize and determine the target configuration that conforms to the usage habits. While increasing the operator customization, the operator can adapt to the target configuration of the parameter adjustment region and find the target location of the parameter that need to be adjusted quickly.

In some embodiments, the operation instruction of the operator obtained in 310 may include a request for configuring the adjustment mode of the scanning parameter, the processing device may determine the target configuration of the adjustment mode of the scanning parameter automatically based on feature information of scanning parameters.

The feature information of the scanning parameter refers to relevant information that reflects features of the scanning parameter. In some embodiments, the feature information of a scanning parameter may include the count of adjustment levels of the scanning parameter, the adjustment frequency of the scanning parameter, at least one of adjustment stages, the importance degree, etc. An adjustment level of a scanning parameter refers to a degree, or value, or a range, or a state that the scanning parameter is able to be adjusted to. The count of the adjustment levels refers to a count of adjustable contents that can be selected for the scanning parameter. For example, if the scanning parameter can be adjusted to 1/2/3/4/5, the parameter may include 5 levels. As a further example, a parameter A may be adjusted to 11 adjustment levels of 0, 1, 2, . . . , 9, 10, while a parameter B may be adjusted to 3 adjustment levels of 1, 2, 3.

The adjustment frequency of a scanning parameter may indicate a count or times of the scanning parameter that has been adjusted in ultrasound examinations over a certain period of time. In some embodiments, the processing device may obtain the historical operation events associated with a scanning parameter of one or more operators for adjusting a scanning parameter and determine the adjustment frequency of the scanning parameter based on the historical operation events. The historical operation events associated with a scanning parameter may be configured to represent a historical adjustment condition of the scanning parameter. For example, a historical operation event may include click, drag, and selection generated by an operator for adjusting the scanning parameter. In some embodiments, the processing device may obtain the historical operation events of the operator for the scanning parameter from the terminal device (e.g., the user terminal 130), the storage device (e.g., the storage device 140), or the ultrasound imaging scanner (e.g., the ultrasound imaging scanner 110). In some embodiments, the processing device may obtain the historical operation events of the operator for the scanning parameter within a preset time period. For example, the preset time period may be within one month, one week, six months, or the like. The preset time period may be set by an operator independently, or the system may automatically determine based on the actual situation. In some embodiments, the processing device may directly obtain the adjustment frequency of the scanning parameter. For example, the processing device may obtain a click frequency, a drag frequency, and a selection frequency a scanning parameter recorded by the user terminal 130 or the ultrasound imaging scanner 110.

The adjustment stage of a scanning parameter refers to a stage of an ultrasound examination during which the scanning parameter is adjusted. In some embodiments, the adjustment stage may include a pre-freezing stage and a post-freezing stage. The pre-freezing stage refers to a stage before the ultrasonic probe emits a sound signal. The post-freezing stage refers to a stage after the ultrasonic probe emits the sound signal. In some embodiments, the processing device may determine the adjustment stage based on whether the probe in the ultrasound imaging scanner 110 emits a sound wave signal.

In some embodiments, the feature information may include an importance degree of the scanning parameter (e.g., a parameter that needs to be adjusted for each ultrasound examination is of a high importance degree). The importance degree of the scanning parameter may be a default setting of the system 100 or may be set by the operator manually.

In some embodiments, the processing device may determine one or more adjustment modes of the scanning parameter based on the feature information of the scanning parameter. A preset corresponding relationship may be between the feature information of the scanning parameter and the adjustment mode of the scanning parameter. The processing device may determine the adjustment mode of the scanning parameter based on the preset corresponding relationship and the feature information. For example, if the feature information of the scanning parameter is a large count of adjustment levels or a low adjustment frequency, the processing device may determine the adjustment mode as a touch screen-based adjustment mode through a preset corresponding relationship.

In some embodiments, the processing device may customize the adjustment mode based on the feature information and/or personalized information of the operator. For example, if the doctor prefers to use the left hand, an adjustment control of a parameter with a relatively high usage frequency may be set in a left area of the control panel and/or touch screen. By allowing the operator to modify the adjustment process, the adjustment control, and/or a position of the ultrasound scanning parameter on a display page according to personal habits of the operator, which can greatly increase customization to meet different operator needs.

In some embodiments, the processing device may use the voice adjustment mode, the EEG adjustment mode, the eye interaction adjustment mode, or the gesture probe-based adjustment mode of the ultrasound imaging scanner as a supplementary adjustment mode. The processing device may adjust the adjustment mode of the scanning parameter in real-time based on the measurement position. For example, when performing the ultrasound examination on the lower limbs, since the doctor is far from the operating platform, it is difficult to touch the control panel and touch screen directly. In this case, the voice adjustment mode or probe-based adjustment mode of the ultrasound imaging scanner may be used to complete freezing, image storage, and other operations. By using the adjustment mode, the voice adjustment mode, the EEG adjustment mode, the eye interaction adjustment mode, or the gesture probe-based adjustment mode of ultrasound imaging scanner as a supplementary adjustment mode, a better role can be played in some special ultrasound examination scenes and the examination efficiency of various ultrasound examination scenes can be improved.

In some embodiments, the operator may preset one or more adjustment modes of the scanning parameter manually. For example, the operator may customize the adjustment mode. For example, the operator may set the scanning parameter such as freezing and image storage with the voice adjustment mode according to the personal needs, and the scanning parameters such as automatic optimization and fusion imaging may be set to be with the adjustment mode (e.g., entity button adjustment, etc.) implemented on the control panel-based adjustment mode. As another example, an adjustment mode of a new scanning parameter may be set based on information such as the count of adjustment levels and functional characteristics added by the operator. More descriptions for determining the target configuration based on feature information may be found elsewhere in the present disclosure (e.g., FIG. 4 and FIG. 9, and the descriptions thereof).

In some embodiments, the touch screen-based adjustment mode may include using one of an excitation type adjustment control, a switch type adjustment control, a tile type adjustment control, a gear adjustment control, a sliding type adjustment control, etc.

The excitation type adjustment control or switch type adjustment control may activate (e.g., turn on) or turn off a corresponding function of the parameter by clicking or other operations. In some embodiments, the excitation type adjustment control or the switch type adjustment control may display a current status of the scanning parameter through a status display or a backlight display.

Figures 5, 6:
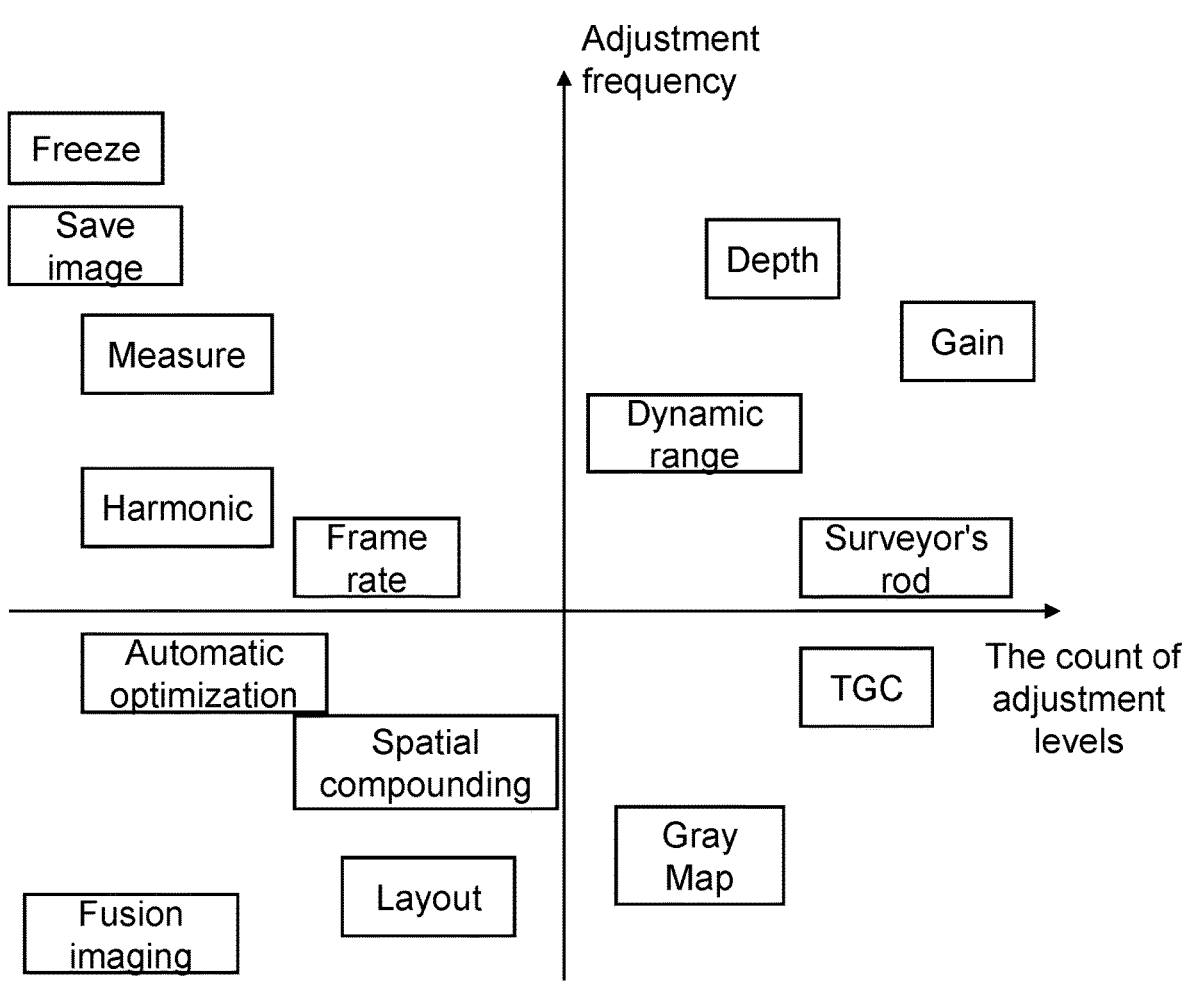
FIG. 5 is a schematic diagram illustrating an exemplary classified result of a scanning parameter according to some embodiments of the present disclosure.
FIG. 6 is a schematic diagram illustrating an exemplary adjustment control of a scanning parameter according to some embodiments of the present disclosure.

The tile type adjustment control may display all options (e.g., adjustment levels, adjustment modes, adjustment views, etc.) in tile types. For example, a tile type adjustment control of a scanning parameter may display all adjustment levels of the scanning parameter. The tile type adjustment control may include a parameter name, an icon, a current selection contents, and an adjustment symbol. As shown in FIG. 6, a control 640 is a tile type adjustment control. The left side of control 640 may display a name "Tint Map" of the scanning parameter and an icon of the canning parameter. The three small rectangular boxes on the right side may display the adjustment symbols "+," "−," and a current selected level "2".

The gear adjustment control may be used to adjust a scanning parameter through "+" and "−".

The sliding type adjustment control may display a current status of a parameter (e.g., the scanning parameter) in a first state (e.g., a current level value, a current mode, or a current view, etc.), and display an option of the parameter (e.g., optional levels, adjustment modes, adjustment views, etc.) in a second state. Generally, the sliding type adjustment control may be initially in the first state, when the parameter (e.g., a target scanning parameter) needs to be adjusted, the second state may be activated by clicking or other operations, and all the optional options (e.g., the adjustment levels) of the parameter may be tiled and displayed in the second state.

Figure 7:
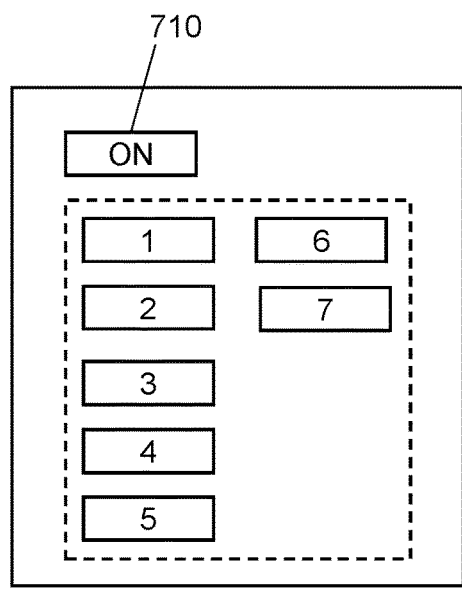
FIG. 7 is a schematic diagram illustrating an exemplary sliding type adjustment control according to some embodiments of the present disclosure.

Merely for example, as shown in FIG. 6, the control 610 is an active type adjustment control, the control 650, the control 670, and the control 680 are tile type adjustment controls, the control 620, the control 640, and the control 660 are gear adjustment controls, and the control 630 is a sliding type adjustment control in the first state. When clicking or other operations are performed on the control 630 in the first state, a second state of the control 630 may be activated to enter a page shown in FIG. 7. In the page shown in FIG. 7, the switch button 710 in the second state may be displayed at the top of the page. Since the page currently displayed shown in FIG. 7 corresponds to the second state of the control 630, the button 710 may displays "ON," if the second state needs to be closed, the button 710 may be clicked, and a corresponding state of the button 710 may switch to "OFF," the page may return to a page shown in FIG. 6; adjustment levels of the corresponding parameter may be displayed below the button 710 (in the white dashed box): 1, 2, 3, 4, 5, 6, and 7, the operator may select a target level to adjust a level of the corresponding parameter.

In some embodiments of the present disclosure, since the control includes the excitation type adjustment control, the switch type adjustment control, the tile type adjustment control, the gear adjustment control, and the sliding type adjustment control, different control types may be determined for different scanning parameters, which can further improve the accuracy of types of the adjustment modes of one or more candidate configurations, and help the operator to adopt more reasonable target configuration subsequent, and find the control corresponding to the scanning parameter quickly when the operator actually adjusts the scanning parameter.

In some embodiments, the processing device may determine a type of adjustment modes of one or more candidate configurations based on the count of adjustment levels of the scanning parameter.

In some embodiments, the processing device may determine that the adjustment mode of the scanning parameter include using an excitation type adjustment control or a switch type adjustment control in response to determining the count of adjustment levels of the scanning parameter is less than a first count threshold. The first count threshold may be determined based on the actual situation, such as 1 or 2. For example, a scanning parameter such as automatic optimization and fusion imaging may be set to be with an adjustment mode using the excitation type adjustment control or the switch type adjustment control.

In some embodiments, the processing device may determine that the adjustment mode of the scanning parameter include using a tile type adjustment control in response to determining that the count of adjustment levels of the scanning parameter is greater than the first count threshold and less than a second count threshold. The second counting threshold may be determined based on the actual situation, such as 2, 3, or 4. For example, a scanning parameter such as spatial composition and layout may be set to be with an adjustment mode using a tile type adjustment control.

In some embodiments, the processing device may determine that the adjustment mode of a scanning parameter include using a gear adjustment control in response to determining that the count of adjustment levels of the scanning parameter is greater than the second counting threshold and less than a third counting threshold. The third threshold may be determined based on the actual situation, such as 4, 5, or 6. For example, the scanning parameter such as Wide View may be set to be with an adjustment mode using a gear adjustment control.

In some embodiments, the processing device may determine that the adjustment mode of a scanning parameter include using a sliding type adjustment control in response to determining that the count of levels of the scanning parameter is greater than the third count threshold. For example, the scanning parameter such as TGC and grayscale image may be set to be with an adjustment mode using a sliding type adjustment control.

In some embodiments, the processing device may determine whether the adjustment control of the scanning parameter is an excitation type adjustment control or a switch type adjustment control in response to the count of adjustment levels of the scanning parameter is less than the first count threshold. In response to the count of adjustment levels of the scanning parameter is greater than or equal to the first count threshold and less than or equal to the second count threshold, the adjustment control of the scanning parameter may be determined as a tile type adjustment control or a gear adjustment control. In response to the count of adjustment levels of the scanning parameter is greater than the second count threshold, the adjustment control of the scanning parameters may be determined as a sliding type adjustment control.

In some embodiments, the processing device may determine that the adjustment control of the scanning parameter includes using an excitation type adjustment control or a switch type adjustment control in response to determining that the count of adjustment levels of the scanning parameter is in a first range. The processing device may determine that the adjustment control of the scanning parameter includes using a tile type adjustment control or a gear adjustment control in response to determining that the count of adjustment levels of the scanning parameter is in a second range. The processing device may determine that the adjustment control of the scanning parameter includes using a sliding type adjustment control in response to determining that the count of adjustment levels of the scanning parameter is in a third range. The first range, the second range, and the third range may be determined based on the actual situations, for example, the first range is 1-3, the second range is 3-6, and the third range is 6-20, or the like.

In some embodiments, the processing device may classify multiple scanning parameters into multiple groups based on the feature information of each of the multiple scanning parameters; and determine an initial adjustment mode for scanning parameters in the same group based on the feature information. More descriptions for classifying the scanning parameters and determining the adjustment mode of the scanning parameters based on the classification results and the feature information may be found in FIG. 4 and related descriptions.

In some embodiments, the processing device may determine the target configuration based on an operation instruction of an operator. For example, the operation instruction of the operator may include the type and/or arrangement of adjustment modes of the scanning parameter. The processing device may configure the type and/or arrangement of adjustment mode of the scanning parameter in the operation instruction as the target configuration of the adjustment mode of the scanning parameter directly. As another example, the processing device may determine the target configuration of the adjustment mode of the scanning parameter based on a corresponding relationship between the operation instruction and the target configuration. The corresponding relationship between the operation instruction and the target configuration may be preset manually or by the system.

In some embodiments, the adjustment mode of the scanning parameter may be determined based on operational convenience. For example, when the doctor needs to zoom in on an image, a process of adjusting physical operation buttons on the control panel may be cumbersome, and an interactive experience may be far less than a gesture operation directly performed on the image, i.e., setting a parameter such as image magnification to a touch screen adjustment.

In some embodiments, the target configuration may be determined based on the feature information of multiple parameters or based on the operation instruction of the operator. More descriptions regarding determination of the target configuration may n be found in FIG. 9 and related descriptions.

In some embodiments, the processing device may determine the target configuration based on one or more candidate configurations (also referred to as candidate configuration templates). For example, the processing device may provide the one or more candidate configurations to the user interface and receive an operation instruction for determining one of the one or more candidate configurations generated by an operator through the user interface. The processing device may designate the determined candidate configuration as the target configuration. As another example, the processing device may modify one of the candidate configurations based on an operation instruction inputted by an operator and designate the modified candidate configuration as the target configuration. As still another example, the processing device may determine one of the one or more candidate configurations based on historical operation events of an operator and designate the determined candidate configuration as the target configuration.

In some embodiments, the processing device may provide one or more candidate configurations of the adjustment mode in response to receipt of the operation instruction. For example, the processing device may generate a configuration interface presented on the user interface of the user terminal of the ultrasound imaging scanner and display the one or more candidate configurations of the adjustment mode of the scanning parameter on the configuration interface. In some embodiments, based on the one or more candidate configurations, the operator may input another operation instruction indicating whether to select one of the candidate configurations as the target configuration and/or select which one among the candidate configurations as the target configuration, so that the processing device may determine the target configuration based on the another operation instruction.

The candidate configuration may include at least one candidate type or candidate arrangement in the adjustment mode of the scanning parameter.

In some embodiments, the processing device may determine the candidate configuration based on historical operation events of the operator for the scanning parameter. For example, the probe-based adjustment mode of the scanning parameter in historical operation event may have a highest frequency of use for the scanning parameter. The processing device may determine the probe-based adjustment mode of the scanning parameter as the type of the adjustment mode of the scanning parameter in one of the candidate configurations of the scanning parameter. The candidate configuration may be determined by other feasible manners, which may not be limited herein.

In some embodiments, the processing device may determine the one or more candidate configurations based on the feature information of the scanning parameter.

In some embodiments, the processing device may determine one or more candidate configurations based on the feature information of the scanning parameter according to a preset rule. The preset rule may present a matching relationship between the feature information of a scanning parameter and a candidate configuration. For example, the preset rule may include that a scanning parameter whose feature information includes a large count of adjustment levels and/or a low adjustment frequency may match a candidate configuration including a touch screen-based mode. As another example, the preset rule may include that a scanning parameter whose feature information includes an adjustment stage being the pre-freezing stage may match a candidate configuration including a candidate arrangement of the adjustment mode of the scanning parameter in the corresponding candidate configuration may be set by setting a front-end parameter at a relatively high position in the parameter adjustment region of the user interface; the preset rule may include the adjustment stage in the feature information being the post-freezing stage, and the candidate arrangement of the adjustment mode of the scanning parameter in the corresponding candidate configuration may be by setting a back-end parameter at a relatively high position in the parameter adjustment region of the user interface. The front-end parameter refers to a scanning parameter that changes the sound output signal (e.g., a depth). After adjusting the front-end parameter, the sound wave signal emitted by the ultrasonic probe may change. The back-end parameter refers to a scanning parameter that does not change the sound output signal (e.g., a gain). After adjusting the back-end parameter, even if the image may change, the sound output signal of the ultrasound probe may not be affected, so that the adjustment may be performed in the post-freezing stage. The preset rule may be other feasible rules, which may not be limited.

In some embodiments of the present disclosure, the one or more candidate configurations may be determined based on the feature information of the scanning parameter, the candidate configurations of the adjustment mode of the scanning parameter can be optimized, which can help the operator to select an optimal target configuration among the candidate configurations.

In some embodiments, the type of the adjustment model of each of the one or more candidate configurations may include a probe-based adjustment mode in response to determining, by the processing device, that the adjustment frequency of the scanning parameter is greater than a first frequency threshold; an adjustment mode implemented on a control panel-based adjustment mode in response to determining, by the processing device, that the adjustment frequency of the scanning parameter is smaller than the first frequency threshold and greater than a second frequency threshold; or an adjustment mode implemented on a control panel-based adjustment mode in response to determining, by the processing device, that the adjustment frequency of the scanning parameter is smaller than the first frequency threshold and greater than a second frequency threshold.

The first frequency threshold and the second frequency threshold may be threshold conditions for determining the adjustment mode of candidate configurations of the scanning parameter. The first frequency threshold and the second frequency threshold may be set independently by the operator or automatically determined by the system based on the actual situation, and the first frequency threshold may be higher than the second frequency threshold.

In some embodiments, the processing device may determine candidate configurations based on a relationship among the adjustment frequency of the scanning parameter, the first frequency threshold, and the second frequency threshold, the adjustment mode of each of the one or more candidate configurations may be determined as a probe-based adjustment mode in response to determining, by the processing device, that the adjustment frequency of the scanning parameter is greater than a first frequency threshold; the adjustment mode of each of the one or more candidate configurations may be determined as an adjustment mode implemented on a control panel-based adjustment mode in response to determining, by the processing device, that the adjustment frequency of the scanning parameter is smaller than the first frequency threshold and greater than a second frequency threshold; or the adjustment mode of each of the one or more candidate configurations may be determined as an adjustment mode implemented on a control panel-based adjustment mode in response to determining, by the processing device, that the adjustment frequency of the scanning parameter is smaller than the first frequency threshold and greater than a second frequency threshold.

In some embodiments of the present disclosure, based on the adjustment frequency of the scanning parameter, the type of the adjustment mode of one or more candidate configurations may be determined, which can optimize the determination of the adjustment mode of the scanning parameter. For example, an adjustment mode of the candidate configurations with a high adjustment frequency may be determined as the probe-based adjustment mode of the ultrasound imaging scanner, which can enable the operator to adjust the scanning parameter with high adjustment frequency more coherently and conveniently during the scanning process, and improve the efficiency of scanning parameter adjustment.

In some embodiments, the type of the adjustment mode of a scanning parameter in a candidate configuration may include the touch screen-based adjustment mode of the ultrasound imaging scanner. The determining the adjustment mode of the candidate configuration may include determining the type of the adjustment control of the scanning parameter. The adjustment mode may correspond to the type of the adjustment control.

Figure 4:
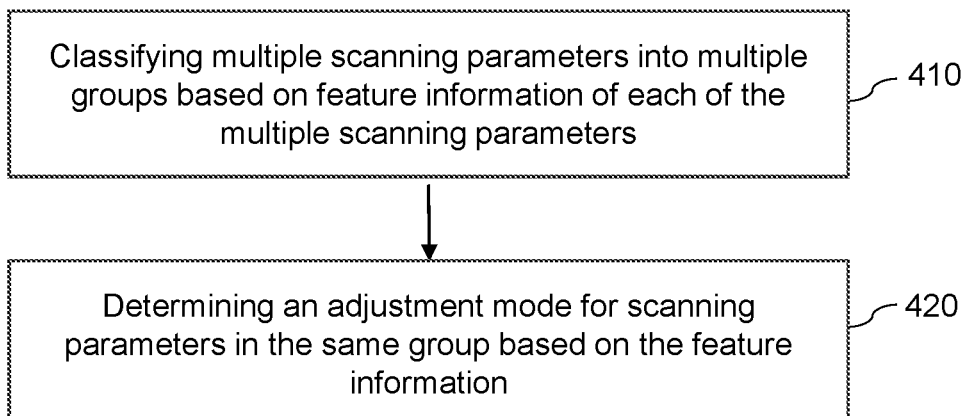
FIG. 4 is a flowchart illustrating an exemplary process of determining an initial adjustment mode according to some embodiments of the present disclosure.

In some embodiments, the type of the adjustment mode in a candidate configuration may be determined based on the feature information according to process 400 as described in FIG. 4. In some embodiments, a candidate configuration may be determined based on similarly as the target configuration according to process 900 as described in FIG. 9.

In some embodiments, the processing device may classify multiple scanning parameters into multiple groups based on the feature information of each of the multiple scanning parameters; and determine the adjustment mode for a scanning parameter in a candidate configuration based on classification results.

In some embodiments, based on the classified results, after the processing device may determine that the adjustment mode of the scanning parameter includes a touch screen-based adjustment mode, the processing device may further determine the type of the adjustment control of the scanning parameter based on the count of the adjustment levels. For example, for the scanning parameter belonging to a second group, the processing device may further determine the control type of the scanning parameter based on the count of adjustment levels. The process of determining the control type may be similar to the above descriptions, which may not be limited herein. More description of the classified result and the scanning parameter of the second group may be found in FIG. 4, FIG. 5, and related descriptions.

In some embodiments, the processing device may determine a control of the scanning parameter based on classified results. Merely for example, if the first count threshold is 2, the second count threshold is 4, and the third count threshold is 6, for a scanning parameter such as automatic optimization and fusion imaging located in a third group shown in FIG. 5, the scanning parameter may be with a relatively low usage frequency and the count of adjustment levels of the scanning parameter may be less than 2, the scanning parameter may be set to be with an adjustment mode including using an excitation type adjustment control or a switch type adjustment control on the touch screen. A scanning parameter Layout has a low usage frequency and the count of adjustment levels of Layout may be between 2-4, which may be adjusted using the tile type adjustment control. A scanning parameter space composite has a low usage frequency and the count of adjustment levels of space composite may be between 4-6, which may be adjusted using the level adjustment type control. A scanning parameter TGC and grayscale diagram located in a fourth group have a low usage frequency and the adjustment levels of TGC and grayscale diagram may be more than 6, which may be adjusted using the sliding type adjustment control.

More descriptions of the third group and the fourth group may be found in FIG. 5 and related descriptions.

In some embodiments of the present disclosure, by using the excitation type or switch type adjustment controls, for the scanning parameter with fewer adjustment levels such as automatic optimization, the parameter content can be fully displayed while having a large enough hot zone to help the operator select the corresponding parameter quickly. By displaying all optional levels directly using the tile type adjustment control, the relatively complex parameters such as a sight range can be adjusted in one step. The adjustment process may be adjusted convenient and fast, and real-time parameter content can also be displayed. By using the gear adjustment control, the current selection contents can be displayed while the efficiency of parameter adjustment can be improved effectively. By using the sliding type adjustment control, for the ultrasound scanning parameters with a large count of adjustment levels such as TGC, a screen space can be saved while providing a relatively large display space that allows more information about the levels to be displayed, which can help the operator select the target content from more than ten levels quickly.

In some embodiments of the present disclosure, the types of adjustment modes of one or more candidate configurations may be determined based on the count of adjustment levels of the scanning parameter, the adjustment mode of the scanning parameter with a relatively large count of adjustment levels may be an adjustment mode implemented by the touch screen-based adjustment mode, making it convenient for the operator to adjust the parameter quickly based on the count of adjustment levels. According to the different types of controls and matching rule for the parameters and controls provided in the present disclosure, device designers or operators only need to classify the parameters. After distinguishing different types of the parameters, a clear and appropriate control can be selected. Based on this, a new parameter design can be completed faster. In addition, doctors may also find a corresponding position of the parameter more quickly, which can effectively improve the efficiency and experience of parameter adjustment.

In some embodiments, the processing device may determine one or more candidate configurations based on feature information of the scanning parameter and historical operation data of the operator.

The historical operation data refers to historical operation data that the operator adjusts the ultrasound scanning parameter. For example, the historical operation data may include a historical operation instruction of the operator. In some embodiments, the processing device may obtain the historical operational data of the operator from the terminal device (e.g., the user terminal 130), the storage device (e.g., the storage device 140), or the ultrasound imaging scanner (e.g., the ultrasound imaging scanner 110).

In some embodiments, the processing device may determine candidate configurations of the scanning parameter based on the feature information of the scanning parameter and the historical operation data (e.g., historical operation events) of the operator use a first trained machine learning model.

The first trained machine learning model may be configured to determine candidate configurations of the scanning parameter and/or the target configuration. In some embodiments, the first trained machine learning model may be a machine learning model, such as convolutional neural networks (CNN), or the like.

In some embodiments, the first trained machine learning model may be trained based on multiple first training samples each of which may be with a first label. Merely for example, the processing device may input each of the multiple first training samples with the first labels into an initial first trained machine learning model, construct a loss function based on an output result of the initial first trained machine learning model and the first label, iteratively update a parameter of the initial first trained machine learning model based on the loss function. When the loss function of the initial first trained machine learning model satisfies a preset condition, the model training may be completed, and the trained first trained machine learning model may be obtained. The preset condition may be a convergence of the loss function, a count of iterations reaching a threshold, or the like. Each of the multiple first training samples may include historical operation data of the sample historical operator and feature information of the sample scanning parameter. The first label may include a historical configuration template actually used by the historical operator corresponding to the first training sample. The first label may be manually labeled. In some embodiments, the first trained machine learning model may be updated based on the historical operation data to recommend the candidate configurations of the adjustment mode of the scanning parameter that the operator is most accustomed to. For example, the processing device may reinput the updated historical operation data as the first training sample into the initial first trained machine learning model to update the parameter of the first trained machine learning model and reobtain the trained first trained machine learning model.

In some embodiments of the present disclosure, based on the feature information of the scanning parameter and the historical operation data of the operator, the candidate configurations may be determined through the first trained machine learning model, which can optimize the adjustment mode of the scanning parameter while recommending the candidate configurations that the operator is accustomed to, achieving personalized candidate configuration determination.

In some embodiments, the processing device may transmit the one or more candidate configurations of the adjustment mode to the user terminal based on the network.

In some embodiments, the operator may determine a target configuration by inputting the operation instruction on the user interface based on the one or more candidate configurations according to a personal preference and actual needs.

In some embodiments of the present disclosure, by transmitting the one or more candidate configurations of the adjustment mode to the operator, the operator may select the target configuration based on the candidate configurations, which can facilitate the operator to quickly select the adjustment mode of the scanning parameter and improve the efficiency of ultrasound examination.

In 330, an ultrasound imaging scanner may be configured based on the target configuration.

In some embodiments, the processing device may configure the ultrasound imaging scanner in multiple ways based on the target configuration. For example, the processing device may generate a control instruction containing information related to the target configuration based on the target configuration, and transmit the control instruction to the ultrasound imaging scanner for configuring the ultrasound imaging scanner based on the target configuration. More descriptions of the ultrasound imaging scanner may be found in FIG. 1 and related descriptions. More descriptions of the target configuration may be found in above description of FIG. 3.

In some embodiments, the user interface represents a parameter adjustment interface in response to receiving the operation instruction for parameter adjustment.

The parameter adjustment interface may be a user interface configured to adjust the scanning parameter. In some embodiments, the parameter adjustment interface may include multiple adjustment controls of the multiple scanning parameters, and the types or target positions of at least one of the multiple adjustment controls on the parameter adjustment interface may be configured based on the operation instruction input by the operator through the user interface. The adjustment control represents an adjustment mode of a scanning parameter. More descriptions of the type and the target position of the adjustment control may be found in above descriptions of FIG. 3 and FIG. 4 and related descriptions.

In some embodiments, the parameter adjustment interface may include a mode display region, a mode switch region, and a parameter adjustment region. The multiple adjustment controls may be arranged in the parameter adjustment region based on the target configurations of multiple parameter adjustment modes.

Figure 8:
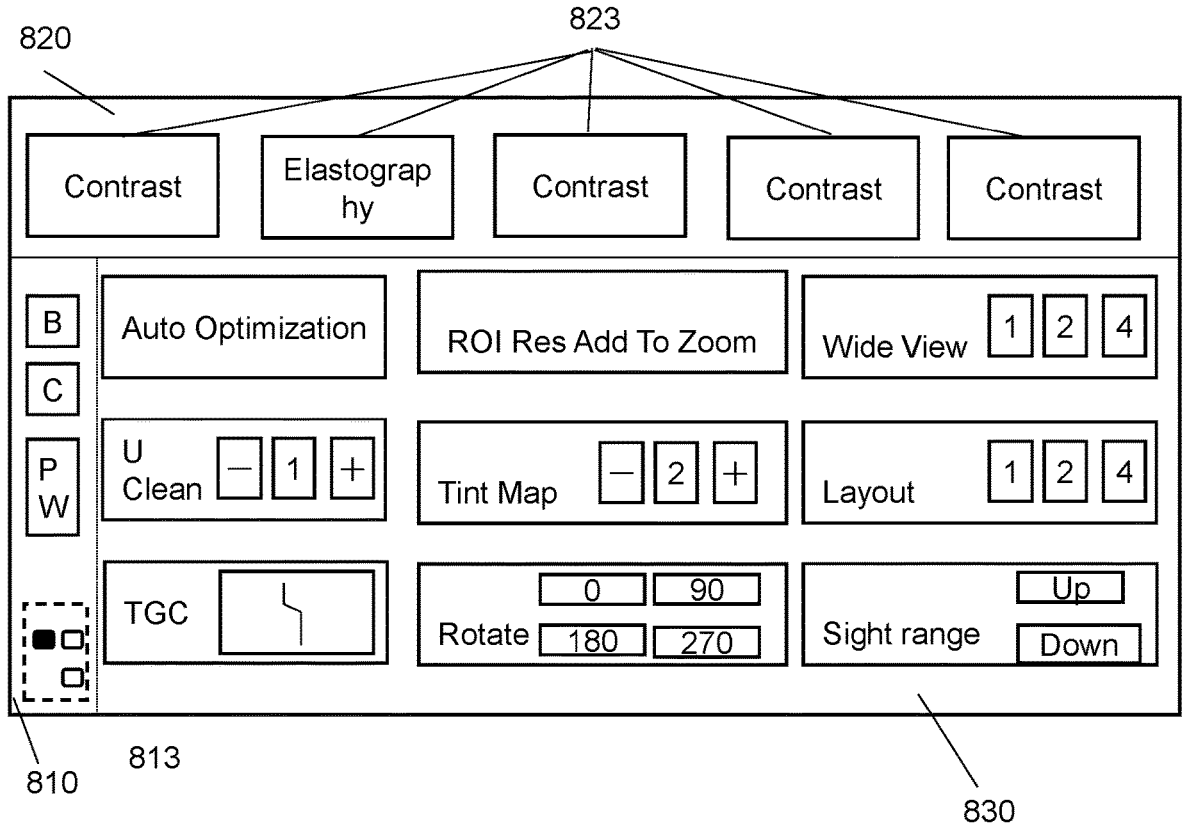
FIG. 8 is a schematic diagram illustrating an exemplary parameter configuration interface of a scanning parameter according to some embodiments of the present disclosure.

The mode display region may be configured to display a switchable mode supported by ultrasound imaging scanner (e.g., a contrast, a B mode, a C mode, a CW mode, or a PW mode, etc.), such as a region 810 shown on a left side of a white dashed line in FIG. 8.

In some embodiments, the mode display region may vary based on a current activated mode. The current activated mode may be selected through the control panel, keyboard input, or from the mode switch region. For example, if the operator inputs the B mode, the C mode, and the PW mode through the keyboard, the B mode, the C mode, and the PW mode may be activated and may be displayed in the mode display region (e.g., the region 810); if the operator selects the B mode through the control panel, the mode display region may only display the B mode; if the B mode is selected through the control panel and "radiography" is selected in the mode switch region (e.g., a region 820), the B mode and radiography may be activated and displayed in the mode display region. When entering a multi-synchronous mode, the mode display region may display a tab page for all optional modes. For example, when the B mode, the C mode, and the PW mode are activated, the mode display region may display the tab page for the B mode, the C mode, and the PW mode. The multi-synchronous mode refers to a mode where the multiple modes are activated.

The mode switch region may be configured to display an entrance of other modes allowed to enter in a current scanning mode (e.g., a contrast, a 3D/4D, a STE, a uFusion, a Panorama, etc.). For example, as shown in FIG. 8, the region 820 above the solid white line represents the mode switch region, and multiple icons 823 in the region 820 represent entrances of other modes allowed to enter in the current mode B.

In some embodiments, the display content of the parameter adjustment region may be switched in the mode display region as needed. After switching the display content of the parameter adjustment region, the parameter adjustment region of the displayed mode may automatically switch. The display content of the parameter adjustment region and the mode display region may change with the mode changes in the mode switch region. After switching a scanning mode from a current scanning mode via an entrance of the scanning mode in the mode switching region, a specific parameter content displayed on the display interface may be changed and mode switching may be carried out, while the ultrasonic scanning device may not undergo the parameter adjustment. After switching to the corresponding page, a function of the parameter adjustment region may be used. For example, as shown in FIG. 8, the region 810 may display a tab page for the B mode, the C mode, and the PW mode. The operator may activate a corresponding mode by clicking on any icon displayed in the region 820, such as clicking the contrast. When the corresponding mode is activated, the mode may be displayed in the region 810; by clicking on a mode button in the region 810, a display content of the parameter adjustment region may be changed to achieve the parameter adjustment. As shown in FIG. 8, the B mode may be selected. Correspondingly, a region 830 may display a corresponding adjustment control of the scanning parameters in the B mode.

In some embodiments, the mode switching may be achieved by operating an entrance of a scanning mode in the mode switch region to enter a display page of the scanning mode. For example, as shown in FIG. 8, the operator may activate a corresponding scanning mode by clicking on any icon in 823 to achieve the mode switching of the ultrasound scanning device. When one of the scanning modes in the mode switching region is selected, a display content of the mode display region may change accordingly. Correspondingly, the display content of the parameter adjustment region may change with the display content of the mode display region.

For example, after selecting the Contrast from the corresponding region 820 in the mode switching region, the Contrast may be displayed in the mode display region 810, and the Contrast may be selected in the region 810 by default. At the same time, the region 830 may display the adjustment control that allows for the parameter adjustment corresponding to the Contrast. At this point, the display content of the mode switch region may switch to the entrances of other modes allowed under the Contrast mode, such as 3D/4D, STE, or the like. If the selected mode in the mode display region is changed, the display content in the mode switching region and mode parameter adjustment region may correspondingly change. It should be understood that the icon 823 shown in the region 820 of FIG. 8 is only for illustration. In practical applications, the multiple "Contrast" icons in the figure may be replaced with 3D/4D, STE, uFusion, or Panorama icons according to the actual situation.

The parameter adjustment region may be configured to display the scanning parameter that are allowed to be adjusted in the current mode corresponding to the mode display region. For example, when the mode B in the region 810 in FIG. 8 is selected, the adjustment controls of the scanning parameters that allows to be adjusted in the mode B may be displayed in the region 830 to a right side of the dashed line.

In some embodiments, the scanning parameter in the current mode may be adjusted by operating the adjustment control in the parameter adjustment region. For example, the operator may adjust the scanning parameter in the B mode by operating the adjustment control in the region 830. In some embodiments, when adjusting the scanning parameter, in addition to different changes in the image displayed in the image region, only a display value of the scanning parameter or closely related parameter may be affected on the touch screen, without changing the scanning parameter displayed in other areas and the overall display interface layout.

By dividing the parameter configuration interface of the scanning parameter into a mode display region, a mode switch region, and a parameter adjustment region, a corresponding region and position of the adjustment control in the corresponding region may be determined based on the feature information of the ultrasonic scanning parameter, not only the parameter adjustment interface may be reasonably partitioned, but also a display rule of the parameter may be effectively clarified, which can present a more logical interface for the operator, enable the operator to quickly find the target scanning parameter, making it more convenient to use and improving the efficiency of parameter adjustment. Moreover, the layout of the editing parameter adjustment interface may be customized, which can be more flexible and applicable. In addition, based on the divided parameter adjustment interface, when the operator needs to add new scanning parameter, the parameter may be added to the corresponding parameter adjustment region in the corresponding mode according to the function, importance degree, and/or the count of the adjustment levels of the parameters, which can provide the reference for the operator.

In some embodiments, for the different scanning modes, different scanning subjects, or different operators, the multiple parameters displayed in the parameter adjustment region may be different. The scanning mode refers to a scanning mode used by the ultrasound imaging scanner for the ultrasound examination, such as the contrast, the B mode, the C mode, the CW mode, the PW mode, or the like. The scanning subject refers to a subject scanned by the ultrasound imaging scanner, such as a patient. For example, in the PW mode, the multiple scanning parameters displayed in the parameter adjustment region may include the scanning parameters that needs to be adjusted in the PW mode; in the B mode, the multiple scanning parameters displayed in the parameter adjustment region may include the scanning parameters that needs to be adjusted in the B mode. In some embodiments of the present disclosure, for the different scanning modes, different scanning subjects, or different operators, the multiple scanning parameters displayed in the parameter adjustment region may be different, which can make the scanning parameters displayed in the parameter adjustment region change according to the actual scanning mode, scanning subject, and operator, which helps to improve the efficiency of parameter adjustment during the ultrasound examination.

In some embodiments, for the different scanning modes, different scanning subjects, or different operators, a target configuration of the multiple parameters and types displayed in the parameter adjustment region may be different. For example, in the PW mode, the scanning parameter with a high adjustment frequency in the PW mode in the parameter adjustment region may be arranged at a relatively high position; in the B mode, the scanning parameter with high adjustment frequency in the parameter adjustment region be arranged at a relatively high position, and the target configuration may also be changed according to different operator habits. In some embodiments of the present disclosure, the target configuration of the multiple parameters displayed in the parameter adjustment region may be changed according to different scanning modes, different scanning subjects, or different operators. The operators may quickly find a position of scanning parameter adjustment, which can improve the efficiency of parameter adjustment during the ultrasound examination.

In some embodiments of the present disclosure, the target configuration of the adjustment mode for the scanning parameter may be determined in response to the operation instruction of the operator, and the ultrasonic imaging device may be configured, which can quickly and efficiently determine the adjustment mode of the scanning parameter that meet the operator needs, thus avoiding a parameter search process effectively and improving the examination efficiency greatly.

FIG. 4 is a flowchart illustrating an exemplary process of determining a type of an adjustment mode according to some embodiments of the present disclosure. In some embodiments, a process 400 may be executed by the processing device 120 or the ultrasound examination system 200. For example, the process 400 may be implemented as instructions (e.g., application programs) and stored in memory such as the storage device 140 that may be accessed by the processing device 120. The processing device 120 may execute the instructions, and when executing the instructions, the process 400 may be executed. The diagram of the process 400 presented below is illustrative. In some embodiments, the process may be accomplished by utilizing one or more undescribed additional operations and/or one or more undescribed operations. In addition, an operation sequence of the process 400 is shown in FIG. 4 and described below is non-restrictive.

In some embodiments, the process 400 may be executed by a processing device. As shown in FIG. 4, the process 400 may include the following operations:

In 410, multiple scanning parameters may be classified into multiple groups based on feature information of each of the multiple scanning parameters. More descriptions of the scanning parameter and the feature information may be found in FIG. 3 and related descriptions. In 420, an adjustment mode for scanning parameters in the same group may be determined based on the feature information. The adjustment mode for the scanning parameters in the same group may be the same. In some embodiments, the adjustment mode of a scanning parameter may include a probe-based adjustment mode, a control panel-based adjustment mode, a touch screen-based adjustment mode, a voice-based adjustment mode, an EEG-based adjustment mode, an eye interaction-based adjustment mode, a gesture-based adjustment mode, etc. The probe-based adjustment mode may further include a button-based adjustment mode, a knob-based adjustment mode, a sensor-based adjustment mode, etc. The control panel-based adjustment mode may further include a button-based adjustment mode, a knob-based adjustment mode, a trackball-based adjustment mode, etc. The touch screen-based adjustment mode may further include using an excitation type adjustment control, a switch type adjustment control, a tile type adjustment control, a gear adjustment control, and a sliding type adjustment control, etc. More descriptions for the adjustment mode may found elsewhere in the present disclosure (e.g., FIG. 3 and the descriptions thereof).

In some embodiments, the processing device may classify the multiple scanning parameters into two groups based on the adjustment frequency of each of the scanning parameters and determine the adjustment mode of each scanning parameter based on the adjustment frequency. For example, the processing device may classify a scanning parameter whose adjustment frequency is greater than the frequency threshold (e.g., the parameters in the first and second groups in FIG. 5) into the same group (also referred to as group A1). The adjustment mode of the scanning parameter may be a probe-based adjustment mode or a control panel-based adjustment mode (e.g., a button adjustment mode) if the scanning parameter belongs to the group A1. The processing device may classify a scanning parameter whose adjustment frequency is less than the frequency threshold (e.g., the parameters in the third and fourth groups in FIG. 5) into the same group (e.g., also referred to as group B1). The adjustment mode of the scanning parameter may be a touch screen-based adjustment mode if the scanning parameter belongs to the group B1. For example, for the scanning parameters shown in FIG. 5, the scanning parameters in the first and second groups may be set to be a probe-based adjustment mode or a control panel-based adjustment mode (e.g., a button adjustment mode), while the scanning parameters of the third and fourth groups may be set to the touch screen-based adjustment mode. More descriptions of the adjustment frequency may be found in FIG. 3 and related descriptions.

In some embodiments, the processing device may classify the multiple scanning parameters into three groups based on the adjustment frequency of each of the scanning parameters and determine the adjustment mode of each scanning parameter based on the adjustment frequency. For example, the processing device may classify a scanning parameter whose adjustment frequency is greater than a first frequency threshold into the same group (also referred to as group A2). The adjustment mode of the scanning parameter may be a probe-based adjustment mode if the scanning parameter belongs to the group A2. The processing device may classify a scanning parameter whose adjustment frequency is less than the first frequency threshold and exceed a second frequency threshold into the same group (e.g., also referred to as group B2). The adjustment mode of the scanning parameter may be a control panel-based adjustment mode if the scanning parameter belongs to the group B2. The processing device may classify a scanning parameter whose adjustment frequency is less than the second frequency threshold into the same group (e.g., also referred to as group C2). The adjustment mode of the scanning parameter may be a touch screen-based adjustment mode if the scanning parameter belongs to the group C2.

In some embodiments, the processing device may classify the multiple scanning parameters into four groups based on the count of adjustment levels of each of the scanning parameter and determine the adjustment mode of each scanning parameter based on the count of adjustment levels. For example, the processing device may classify a scanning parameter whose count of adjustment levels of each of the scanning parameter is less than a first count threshold into the same group (also referred to as group A3). The adjustment mode of the scanning parameter may be the excitation type adjustment control or the switch type adjustment control if the scanning parameter belongs to the group A3. The processing device may classify a scanning parameter whose count of adjustment levels of each of the scanning parameter exceeds the first count threshold and is less than a second count threshold into the same group (also referred to as group B3). The adjustment mode of the scanning parameter may be the tile type adjustment control if the scanning parameter belongs to the group B3. The processing device may classify a scanning parameter whose count of adjustment levels of each of the scanning parameter exceeds the second count threshold and is less than a third count threshold into the same group (also referred to as group C3). The adjustment mode of the scanning parameter may be the gear adjustment control if the scanning parameter belongs to the group C3. The processing device may classify a scanning parameter whose count of adjustment levels of each of the scanning parameter exceeds the third count threshold into the same group (also referred to as group D3). The adjustment mode of the scanning parameter may be the sliding type adjustment control if the scanning parameter belongs to the group D3.

In some embodiments, the processing device may classify the multiple scanning parameters into four groups based on the count of adjustment levels and the adjustment frequency of each of the scanning parameters. For example, the processing device may classify a scanning parameter in group A1 whose count of adjustment levels is greater than a count threshold (e.g., the parameters in the first quadrant in FIG. 5) into a first group. The adjustment mode of a scanning parameter in the first group may include a knob adjustment mode. The first group of scanning parameters may belong to group A1. The processing device may classify a scanning parameter in group A1 whose count of adjustment levels is less than the count threshold (e.g., the parameters in the second quadrant in FIG. 5) into a second group. The adjustment mode of a scanning parameter in the second group may include a button or key adjustment mode. The second group of scanning parameters may belong to group A1. The processing device may classify a scanning parameter in group B1 whose count of adjustment levels is less than the count threshold (e.g., the parameters in the third quadrant in FIG. 5) into a third group. The third group of scanning parameters may belong to group B1. The adjustment mode of a scanning parameter in the third group may include an excitation type adjustment control or a switch type adjustment control implemented on a touch screen. The processing device may classify a scanning parameter in group B1 whose the count of adjustment levels is greater than the count threshold (e.g., the parameters in the fourth quadrant in FIG. 5) in to a fourth group. The fourth group of scanning parameters may belong to group B1. The adjustment mode of a scanning parameter in the fourth group may include a tile type adjustment control, a gear adjustment control, or a sliding type adjustment control implemented on a touch screen.

In some embodiments, the frequency thresholds (e.g., the first frequency threshold, the second frequency threshold, etc.) and count thresholds (e.g., the first count threshold, the second count threshold, the third count threshold, etc.) may be a default setting of the system or set according to actual needs. For example, the count threshold may be 6, 4, 10, or the like, and the frequency threshold may be 10 times/week, 20 times/week, 50 times/week, or the like. In some embodiments, the frequency threshold and/or count threshold may be set independently by the operator.

In some embodiments, when the adjustment mode of the scanning parameter is determined as a control panel-based adjustment mode (e.g., a scanning parameter in group A1, or group B2), the processing device may determine the adjustment mode of a scanning parameter as knob adjustment mode or button adjustment mode based on the count of adjustment levels. For example, in FIG. 5, when a scanning parameter located in the first quadrant has a relatively high count of adjustment levels, the adjustment mode of the scanning parameter may be a knob adjustment mode; a scanning parameter located in the second quadrant has a relatively low the count of adjustment levels, the adjustment mode of the scanning parameter may be a button adjustment mode.

In some embodiments, if the adjustment mode of the scanning parameter is determined as a touch screen-based adjustment mode (e.g., a scanning parameter in group B1 or group C2), adjustment mode of the scanning parameter may be further determined as an excitation type adjustment mode or a sliding type adjustment mode based on the count of adjustment levels. For example, as shown in FIG. 5, for a scanning parameter located in the third quadrant, the count of adjustment levels may be relatively low, so that the adjustment mode of the scanning parameter in the third quadrant may be the excitation type adjustment mode; the adjustment mode of the scanning parameter located in the fourth quadrant whose count of adjustment levels is relatively high may be the sliding type adjustment mode.

In some embodiments, the processing device may classify a scanning parameter whose adjustment frequency is greater than a frequency threshold and count of adjustment levels exceeds a count threshold into a first group. Merely for example, as shown in FIG. 5, the horizontal axis represents the count of adjustment levels of the scanning parameter, and the vertical axis represents the adjustment frequency of the scanning parameter. The scanning parameter whose adjustment frequency is greater than the frequency threshold and the count of adjustment levels is greater than the count threshold, such as a depth, a dynamic range, a scale, a gain, etc., may be classified into the first group. In some embodiments, in response to determining that the scanning parameter belongs to the first group, the processing device may determine the adjustment mode (i.e., the type of the adjustment mode) of the scanning parameter as a knob adjustment mode for adjusting the scanning parameter using a knob implemented on the control panel-based adjustment mode.

In some embodiments, the processing device may classify a scanning parameter whose adjustment frequency is greater than a frequency threshold and count of adjustment levels is less than a count threshold into a second group. Merely for example, as shown in FIG. 5, the scanning parameter whose adjustment frequency is greater than the frequency threshold and count of adjustment levels is less than the count threshold, such as freezing, image storage, measuring, harmonic, frame rate, frame frequency, etc., may be classified into a second group. In some embodiments, in response to determining that the scanning parameter belongs to the second group, the processing device may determine the adjustment mode corresponding to the second group as a button adjustment mode for adjusting the scanning parameter using the button implemented on the control panel-based adjustment mode.

In some embodiments, the processing device may classify a scanning parameter whose adjustment frequency is less than the frequency threshold and the count of adjustment levels is less than the count threshold into a third group. Merely for example, as shown in FIG. 5, the scanning parameter whose adjustment frequency is less than the frequency threshold and count of adjustment levels is less than the count threshold, such as automatic optimization, spatial composition, fusion imaging, layout, etc., may be classified into the third group. In some embodiments, in response to determining that the scanning parameter belongs to the third group, the processing device may determine the adjustment mode of the scanning parameter corresponding to the third group as an excitation type adjustment control or a switch type adjustment control implemented on the touch screen-based adjustment mode.

In some embodiments, the processing device may classify a scanning parameter whose adjustment frequency is less than the frequency threshold and count of adjustment levels exceeds the count threshold into a fourth group. Merely for example, as shown in FIG. 5, the scanning parameter whose adjustment frequency is less than the frequency threshold and count of adjustment levels exceeds the quantity threshold, such as a gray scale chart, TGC, etc., may be classified into the fourth group. In some embodiments, in response to determining that the scanning parameter belongs to the fourth group, the processing device may the adjustment mode of the scanning parameter corresponding to the fourth group as a tile type adjustment control or a gear adjustment control implemented on the touch screen-based adjustment mode.

The count threshold and/or the frequency threshold may be a default setting of the system 100 or set by an operator of the ultrasound imaging scanner according to actual needs. In some embodiments, the system 100 may adjust and/or update the count threshold and/or the frequency threshold periodically or aperiodically.

According to the difference of scanning positions and personal habits of different operators, the adjustment frequencies of different scanning parameters may be different. For example, the adjustment frequency of the scanning parameter such as the depth or the gain is relatively high, while the adjustment frequency of a scanning parameter such as pseudo color is relatively low. For different scanning parameters, the count of adjustment levels may be completely different. For example, the gain includes over 100 adjustment levels available for the operators to select or adjust. The Pseudo color includes around 10 adjustment levels (i.e., options) for the operators to select or adjust. The image layout includes multiple adjustment levels (i.e., options) such as single display, double display, and four display for the operators to select or adjust. The automatic optimization includes two adjustment levels (i.e., options): on and off. The elasticity includes only one adjustment level (i.e., activation button), and the function of the elasticity may be activated by pressing the activation button. In some embodiments of the present disclosure, the scanning parameters may be comprehensively classified based on the adjustment frequency and the count of adjustment levels, which not only allows for the determination of more convenient adjustment modes of scanning parameters with relatively high adjustment frequency, but also allows for the selection of more convenient and less space consuming adjustment controls of scanning parameters with the relatively high count of adjustment levels, resulting in improving the convenience of parameter adjustment, thereby avoiding the problem of operator confusion caused by overly complex control panel or display interface, and effectively reducing the count of physical buttons appearing on the control panel.

According to parameter classified rules, different styles of parameter adjustment controls, and a matching rule between parameters and controls provided in the present disclosure, device designers or operators only need to classify the parameters based on the functions, importance degrees, or adjustment levels. After distinguishing different types of parameters, a clear and appropriate control can be selected, based on this, a new parameter design can be completed faster. In addition, operations can also find a corresponding position for adjusting the scanning parameter more quickly, which can effectively improve the efficiency and experience of parameter adjustment.

It should be noted that the above description of the process 400 is only for example and explanation, and does not limit the scope of application of the present disclosure. For those skilled in the field, various modifications and changes can be made to the process 400 under the guidance of the present disclosure. For example, in 410, a fifth group may be determined in response to the count of adjustment levels in the scanning parameter being greater than the quantity threshold; a sixth group may be determined in response to the count of adjustment levels in the scanning parameter being less than or equal to the quantity threshold. As another example, the operation 420 can be omitted, and after classification, the adjustment control of the scanning parameter may be determined directly based on the classified result. However, these modifications and changes are still within the scope of the present disclosure.

Some embodiments of the present disclosure provide a system including an ultrasound imaging scanner and a user terminal in communication with the ultrasound imaging scanner. The user terminal may include a user interface implemented on a touch screen. In response to receiving the operation instruction for entering a parameter configuration interface, the user interface may represent the parameter configuration interface. In response to receipt of an operation instruction for adjustment mode configuration (e.g., including a type of an adjustment mode and/or a position of the adjustment mode on a parameter adjustment interface) of a scanning parameter, the processing device may determine the type of the adjustment mode and/or position of the adjustment mode of the scanning parameter on the parameter adjustment interface based on the operation instruction for adjustment mode configuration or according to feature information of the scanning parameter as described elsewhere in the present disclosure. For example, the operation instruction for adjustment mode configuration inputted by an operator may include a type of an adjustment mode and/or a position of the adjustment mode on a parameter adjustment interface, and the processing device may configure the adjustment mode of the scanning parameter based on the type of the adjustment mode and/or the position of the adjustment mode on a parameter adjustment interface included in the operation instruction.

In response to receiving an operation instruction for entering the parameter adjustment interface, the user interface may represent the parameter adjustment interface. The parameter adjustment interface may include multiple adjustment controls of multiple scanning parameters, and a target position of each of the multiple adjustment controls in the parameter configuration interface. In some embodiments, at least apportion of the multiple adjustment controls of multiple scanning parameters and the target position of each of at least a portion of the multiple adjustment controls in the parameter configuration interface may be determined or adjusted according to an operation instruction for adjustment mode configuration input by an operator via the user interface, and each of the multiple adjustment controls may indicate a target adjustment mode of a scanning parameter. More descriptions of the ultrasound imaging scanner, the user terminal, the user interface may be found in FIG. 1 and related descriptions. More descriptions of the parameter configuration interface, the operation instruction, and the input may be found in FIG. 3 and related descriptions.

A system may be provided in some embodiments of the present disclosure, the system may further include at least one processing device in communication with the at least one storage medium. When executing the set of instructions, the at least one processing device may be directed to cause the system to perform operations including obtaining, from the user terminal, an operation instruction for confirming or adjusting an initial adjustment mode of the scanning parameter, determining, based on the operation instruction of the operator, the target adjustment mode of the scanning parameter; and configuring the ultrasound imaging scanner based on the target adjustment mode. More descriptions may be found in FIG. 3 and related descriptions.

Figure 9:
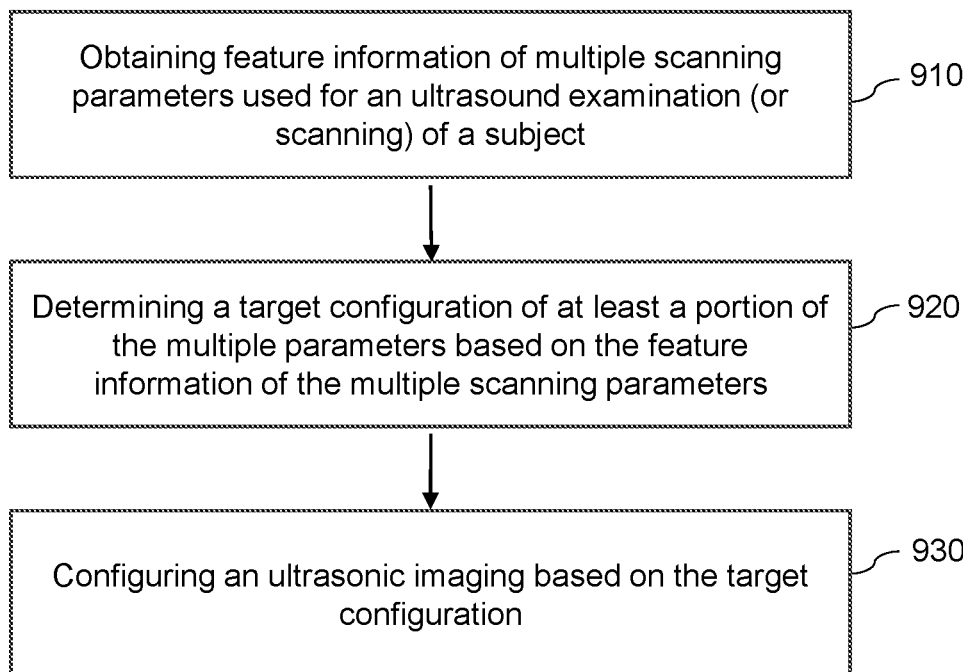
FIG. 9 is another schematic diagram illustrating an exemplary process of determining a target adjustment mode of a scanning parameter according to some embodiments of the present disclosure.

FIG. 9 is a schematic diagram illustrating another exemplary process of determining a target adjustment mode of a scanning parameter according to some embodiments of the present disclosure. In some embodiments, a process 900 may be executed by the processing device 120 or the ultrasound examination system 200. For example, process 900 may be implemented as instructions (e.g., application programs) and stored in memory such as the storage device 140 that may be accessed by the processing device 120. The processing device 120 may execute the instructions, and when executing the instructions, process 900 may be executed. Process 900 presented below is illustrative. In some embodiments, process 900 may be accomplished by utilizing one or more undescribed additional operations and/or one or more undescribed operations. In addition, an operation sequence of the process 900 is shown in FIG. 9 and described below is non-restrictive. In some embodiments, the process 900 may be executed by a processing device (e.g., the processing device 120 or a processing device for implementing modules of the ultrasound examination system 200. As shown in FIG. 9, the process 900 may include the following operations.

In 910, feature information of multiple scanning parameters used for an ultrasound examination (or scanning) of a subject may be obtained.

In some embodiments, the processing device may determine the multiple scanning parameters used for the ultrasound examination (or scanning) of the subject in response to receipt of an operation instruction for adjustment mode configuration generated by an operator of the ultrasound examination system through a terminal device of the ultrasound examination system (e.g., a user interface). Then the processing device may obtain the feature information of the determined scanning parameters.

In some embodiments, different scanning modes may correspond to different scanning parameters to be adjusted for ultrasound examination. In some embodiments, the scanning parameters under the scanning mode may be determined according to a corresponding relationship between scanning parameters and scanning modes. The corresponding relationship may indicate types of scanning parameters under each of the scanning modes. More descriptions of the scanning mode may be found in FIG. 3 and related descriptions.

In some embodiments, different scanning portions of the subject may correspond to different scanning parameters to be adjusted for ultrasound examination. In some embodiments, the scanning parameters for different scanning portions of the subject may be determined according to a corresponding relationship between scanning parameters and scanning portions of the subject. The corresponding relationship may indicate types of scanning parameters for each of the scanning portions.

In some embodiments, different subjects may correspond to different scanning parameters to be adjusted for ultrasound examination. In some embodiments, the scanning parameters for different subjects may be determined according to a corresponding relationship between scanning parameters and subjects. The corresponding relationship may indicate types of scanning parameters for each of the different subjects.

In some embodiments, the feature information may include at least one of a count of adjustment levels of the scanning parameter, an adjustment frequency of the scanning parameter, an adjustment stage, etc. More descriptions of the feature information of the scanning parameter may be found elsewhere in the present disclosure (e.g., FIG. 3 and related descriptions thereof).

In some embodiments, the processing device may obtain the feature information of the scanning parameters from the storage device and/or the ultrasound imaging scanner. More descriptions of obtaining the feature information of the scanning parameter may be found in FIG. 3 and related descriptions.

In 920, a target configuration of at least a portion of the multiple parameters may be determined based on the feature information of the multiple scanning parameters.

The target configuration of the adjustment mode of a scanning parameter may include at least one of the type or the arrangement of the adjustment mode. More descriptions regarding the type and/or the arrangement of the adjustment mode may be found elsewhere in the present disclosure (e.g., FIG. 3 and FIG. 4 and related descriptions thereof). For example, a type of an adjustment mode may include a probe-based adjustment mode, a control panel-based adjustment mode, a touch screen-based adjustment mode, a voice-based adjustment mode, an EEG-based adjustment mode, an eye interaction-based adjustment mode, a gesture-based adjustment mode, etc. The probe-based adjustment mode may further include a button-based adjustment mode, a knob-based adjustment mode, a sensor-based adjustment mode, etc. The control panel-based adjustment mode may further include a button-based adjustment mode, a knob-based adjustment mode, a trackball-based adjustment mode, etc. The touch screen-based adjustment mode may further include using an excitation type adjustment control, a switch type adjustment control, a tile type adjustment control, a gear adjustment control, a sliding type adjustment control, etc.

In some embodiments, the target configuration of a scanning parameter may be determined based on the feature information of the scanning parameter.

For example, the type of the scanning parameter may be determined based on the feature information of the scanning parameter according to process 400 as described in FIG. 4.

In some embodiments, the adjustment mode of the scanning parameter may be a probe-based adjustment mode if the adjustment frequency of the scanning parameter is greater than a first frequency threshold; the adjustment mode of the scanning parameter may be a control panel-based adjustment mode if the adjustment frequency of the scanning parameter is smaller than the first frequency threshold and exceed a second frequency threshold; the adjustment mode of the scanning parameter may be a touch screen-based adjustment mode if the adjustment frequency of the scanning parameter is smaller than the second frequency threshold. Further, for the scanning parameter whose adjustment frequency of the scanning parameter is greater than a first frequency threshold and the adjustment mode is a probe-based adjustment mode, the adjustment mode of the scanning parameter may be a knob-based adjustment mode if the count of adjustment levels of the scanning parameter is greater than a first count threshold; the adjustment mode of the scanning parameter may be a button-based adjustment mode or a sensor-based adjustment mode if the count of the adjustment levels of the scanning parameter is smaller than the count threshold. For the scanning parameter whose adjustment frequency of the scanning parameter is smaller than the first frequency threshold and exceed a second frequency threshold and the adjustment mode is a control panel-based adjustment mode, the adjustment mode of the scanning parameter may be a trackball-based adjustment mode if the count of adjustment levels of the scanning parameter is greater than a first count threshold; the adjustment mode of the scanning parameter may be a knob-based adjustment mode if the count of the adjustment levels of the scanning parameter is smaller than the first count threshold and exceeds a second count threshold; the adjustment mode of the scanning parameter may be a button-based adjustment mode if the count of the adjustment levels of the scanning parameter is smaller than the second count threshold. For the scanning parameter whose adjustment frequency of the scanning parameter is smaller than the second frequency threshold and the adjustment mode is a touch screen-based adjustment mode, the adjustment mode of the scanning parameter may include using a sliding type adjustment control if the count of adjustment levels of the scanning parameter is greater than a first count threshold; the adjustment mode of the scanning parameter may include using a gear adjustment control if the count of the adjustment levels of the scanning parameter is smaller than the first count threshold and exceeds a second count threshold; the adjustment mode of the scanning parameter may be a tile type adjustment control if the count of the adjustment levels of the scanning parameter is smaller than the second count threshold and exceeds a third count threshold; the adjustment mode of the scanning parameter may include using an excitation type adjustment control or the switch type adjustment control if the count of the adjustment levels of the scanning parameter is smaller than the third count threshold.

In some embodiments, the adjustment mode of the scanning parameter may be a touch screen-based adjustment if the adjustment frequency of the scanning parameter is greater than a first frequency threshold; the adjustment mode of the scanning parameter may be a control panel-based adjustment mode if the adjustment frequency of the scanning parameter is smaller than the first frequency threshold and exceed a second frequency threshold; the adjustment mode of the scanning parameter may be a probe-based adjustment mode if the adjustment frequency of the scanning parameter is smaller than the second frequency threshold.

In some embodiments, the adjustment mode of the scanning parameter may be a control panel-based adjustment if the adjustment frequency of the scanning parameter is greater than a first frequency threshold; the adjustment mode of the scanning parameter may be a probe-based adjustment mode if the adjustment frequency of the scanning parameter is smaller than the first frequency threshold and exceed a second frequency threshold; the adjustment mode of the scanning parameter may be a touch screen-based adjustment mode if the adjustment frequency of the scanning parameter is smaller than the second frequency threshold.

The first frequency threshold may be greater than the second frequency threshold. The first frequency threshold and/or the second frequency threshold may be a default setting of the system 100 or 200 or set by a operator according to actual requirements.

In some embodiments, for a scanning parameter whose adjustment mode includes a touch screen-based adjustment (e.g., a control-based adjustment mode including using an excitation type adjustment control, a switch type adjustment control, a tile type adjustment control, a gear adjustment control, and a sliding type adjustment control), the arrangement of the adjustment mode on a parameter adjustment interface may be determined based on the feature information of the scanning parameter. The arrangement of the adjustment mode of a scanning parameter may include a position of a control used for the adjustment mode of the scanning parameter (also referred to as an adjustment control) on the parameter adjustment interface.

In some embodiments, the parameter adjustment interface may include a parameter adjustment region. In some embodiments, an adjustment control corresponding to the scanning parameter may be displayed in the parameter adjustment region based on the feature information of the scanning parameter. For example, the processing device may arrange the adjustment control of a scanning parameter whose adjustment frequency exceeds a frequency threshold at a center of the parameter adjustment region; the processing device may arrange the adjustment control of a scanning parameter whose adjustment frequency is less than the frequency threshold at a boundary region of the parameter adjustment region. As another example, the processing device may arrange the adjustment control of a scanning parameter whose count of adjustment levels exceeds a count threshold at a center of the parameter adjustment region; the processing device may arrange the adjustment control of a scanning parameter whose count of adjustment levels is less than the count threshold at a boundary region of the parameter adjustment region. In some embodiments, the position of the scanning parameter may be determined based on the importance degree of the scanning parameter. For example, the processing device may display the scanning parameter with high importance degree (e.g., a parameter used in ultrasound measurement) at a center of a main page or at a convenient position for operation (e.g., on a left or right side of the interface).

In some embodiments, the adjustment controls corresponding to scanning parameters under a scanning mode may be displayed on the same or different pages in the parameter adjustment region based on the feature information of the scanning parameter. For example, the adjustment controls of scanning parameters whose adjustment frequencies exceeds a frequency threshold may be displayed on the first page in the parameter adjustment region; the adjustment controls of scanning parameters whose adjustment frequencies is smaller than the frequency threshold may be displayed on the second page, the third page, etc. Accordingly, the processing device may display a parameter with relatively high adjustment frequency on the main page (e.g., a first page) based on the adjustment frequency of the scanning parameter, and a parameter with relatively low adjustment frequency on the flipped page (e.g., a second or third page). Merely for example, as shown in FIG. 8, in a dashed rectangular box 813 at the bottom of the region 810, three small bars may be used to represent a total of three pages. An operator may switch between three different pages by flipping, different scanning parameters under a scanning mode may be displayed on each page. One of the three small bars may be highlighted to indicate a current page displaying adjustment control of scanning parameters.

In some embodiments, the count of pages may be determined based on a total count of scanning parameters under a scanning mode and a maximum count of scanning parameters under one page. For example, if the maximum count of scanning parameters under one page is 9, and there are more than 9 parameters in the same scanning mode, a vertical scroll bar, a horizontal scroll bar, or page turning may be used for displaying more than 9 parameters on different pages. As still another example, the adjustment control of the u scanning parameter with relatively high adjustment frequency may be displayed in a first row and first column of the first page of the parameter adjustment region. As still another example, the adjustment control of the u scanning parameter with relatively high importance degree may be displayed on a homepage of the parameter adjustment region. In some embodiments, the ultrasound scanning parameters may be classified based on the feature information, and the adjustment controls of the scanning parameters may be distributed in the parameter adjustment region based on the classified result. More descriptions may be found in FIG. 4 and related descriptions, which may not be repeated herein. For example, adjustment controls of the first group and/or the second group of scanning parameters may be displayed in a first row and first column of the first page of the parameter adjustment region. As another example, adjustment controls of the third group and/or the fourth group of scanning parameters may be displayed in a second row and second column of the next page of the parameter adjustment region.

In some embodiments, different scanning modes, scanning subjects, different operators, and/or different scanning portions, etc., may correspond to different scanning parameters and correspond to different target configurations of adjustment modes of the same scanning parameter. In some embodiments, under the same scanning mode, the count of scanning parameters whose adjustment controls are arranged on the parameter adjustment region may exceed a threshold (e.g., 6, 7, 8, 9, 10, etc.).

In some embodiments, the parameter adjustment interface may include a mode display region and/or a mode switch region.

The mode display region may be configured to display scanning modes, such as B mode, C mode, PW mode, etc. In some embodiments, the mode display region may highlight a scanning mode that is excited or selected by an operator and the parameter adjustment region may display scanning parameters corresponding to the highlighted scanning mode in the mode display region. In some embodiments, if the operator changes the scanning mode highlighted in the mode display region, the parameter adjustment region may display the scanning parameters corresponding to the changed scanning mode, but the scanning parameters corresponding to the changed scanning mode may be not adjusted via the adjustment controls displayed in the parameter adjustment region. The scanning parameters corresponding to the changed scanning mode may be different from or same as scanning parameters of a previous scanning mode.

The mode switch region may be configured to switch between different scanning modes. For example, the mode switch region may display one or more entrances for entering other scanning modes from a current scanning mode. In response to receipt of an operation instruction for selecting one entrance of a scanning mode, the scanning mode corresponding to the selected entrance may be excited and highlighted on the mode display region. The parameter adjustment region may display scanning parameters corresponding to the selected scanning mode and the scanning parameters corresponding to the selected scanning mode may be adjusted via the adjustment controls displayed on the parameter adjustment region. As shown in FIG. 8, scanning modes such as the B mode, the C mode, and the PW mode are displayed in region 810 representing a mode display region, and scanning modes, such as the contrast, the 3D/4D, the elasticity (STE), the fusion imaging (uFusion), and the panoramic imaging (Panorama) are displayed in region 820 representing a mode switch region, and scanning parameters corresponding to a scanning mode are displayed in region 830 representing the parameter adjustment region. Region 830 displays scanning parameters that need to be adjusted under B mode highlighted in region 810. If B mode is excited, the scanning parameters under B mode may be adjusted via adjustment controls displayed in region 830.

In some embodiments, the adjustment control of the scanning parameter corresponding to a target scanning mode may be displayed in the parameter adjustment region and the scanning parameter corresponding to the target scanning mode may be adjusted through the adjustment control. The target scanning mode may refer to a scanning mode that is excited or selected via an entrance in the mode switch region. Different scanning modes may correspond to the same or different scanning parameters. For example, if a scanning parameter M is allowed to be adjusted under mode B, mode B may be related to the scanning parameter M. Based on the feature information of scanning parameter M, the adjustment module 220 may distribute the adjustment control of the scanning parameter M in the parameter adjustment region under mode B.

In some embodiments, a position and/or page of the mode parameter adjustment region of the scanning parameter in the target mode may be determined based on the feature information of the scanning parameter.

In some embodiments, the processing device may optimize the layout of various adjustment controls or regions on the parameter adjustment interface based on the personal information of the operator. In some embodiments, the processing device may adjust a position of each region on the display interface according to the personal preferences of the operator, the operating habits, and other information. For example, region 810 may be set at the bottom of the parameter adjustment interface, and the region 830 may be set on a left side of the parameter adjustment interface. In some embodiments, for different operators, the scanning modes in the mode display region and/or in the mode switch region, or adjustment controls of the scanning parameters in the parameter adjustment region may be displayed in different positions or pages based on the historical operation events of the operator. For example, for an operator X,PW mode may be displayed at a top of region 820, and B mode may be displayed at a bottom of the region 820. As another example, for operator Y, scanning parameters including Wide View, Layout, and track range may be displayed on a left side of region 830 or scanning parameters such as rotation and track range may be displayed on a second page of region 830.

In some embodiments, the layout of each adjustment control and/or partition region on the parameter adjustment interface may be optimized based on the scanning portion of the target subject. In some embodiments, the layout of each adjustment control and/or partition region on the parameter adjustment interface may be optimized based on the operation instruction of an operator (also referred to as an operator). For example, the operator may customize the layout of various scanning parameters on the parameter adjustment interface. As a further example, the custom setting process for layout may include a long pressing the parameter adjustment control to activate the entire page, and dragging and dropping the parameter adjustment control on the page to adjust the position of the corresponding parameter adjustment control, adding a new parameter adjustment control, or deleting existing parameter adjustment control.

In some embodiments, the adjustment mode of the scanning parameter may be implemented based on the adjustment control. In some embodiments, the processing device may determine a parameter adjustment region on the user interface, and set multiple adjustment controls of multiple scanning parameters in the parameter adjustment region under the scanning mode based on the feature information of multiple scanning parameters. Each of the multiple scanning modes may include multiple certain scanning parameters and a certain arrangement of multiple certain scanning parameters in the parameter adjustment region. More descriptions of the feature information and the adjustment control may be found in FIG. 3 and related descriptions.

In some embodiments, the parameter adjustment region may be preset based on the system. As shown in FIG. 8, the system may preset the parameter adjustment region on a right side of the dashed line of the region 830. The parameter adjustment region may also be determined based on the operation instruction of the operator.

In some embodiments, the processing device may set the multiple adjustment controls of the multiple scanning parameters in the parameter adjustment region under the scanning mode through various processes based on the feature information of multiple scanning parameters. For example, the processing device may determine the scanning parameters of the touch screen-based adjustment mode of the ultrasonic imaging device in the candidate configuration of the scanning parameter as a certain scanning parameter in the parameter adjustment region based on the feature information of the scanning parameter, and determine a corresponding adjustment control based on the count of the adjustment levels of the certain scanning parameter, more descriptions may be found in FIG. 3 and related descriptions.

In some embodiments, the processing device may determine a target position of the certain scanning parameter in the parameter adjustment region as a specific arrangement in the parameter adjustment region. More description of a certain arrangement in the parameter adjustment region may be found in FIG. 3 and related descriptions.

In some embodiments of the present disclosure, the multiple parameter adjustment controls and the specific arrangement of scanning parameters in the parameter adjustment region may be designed based on the feature information of the ultrasound scanning parameter, which can better adjust the corresponding parameter and obtain good interface feedback.

In 930, an ultrasonic imaging device may be configured based on the target configuration. More descriptions of configuring the ultrasonic imaging device based on the target configuration may be found in FIG. 3 and related descriptions.

In some embodiments of the present disclosure, by determining the target configuration based on the feature information of multiple scanning parameters, and configuring the ultrasound imaging scanner based on the target configuration, the parameter adjustment interface of the ultrasound measurement device may be optimized, and the operator may obtain a more logical interface, which is more convenient for use.

A computer-readable storage medium may be provided in some embodiments of the present disclosure, the computer-readable storage medium may store computer instructions, when the computer executes computer instructions, the computer instruction may be configured to determine the adjustment mode of the scanning parameter as described above (e.g., the process 300 or process 900).

The beneficial effects in the embodiments of the present disclosure may include but are not limited to: (1) the scanning parameters may be classified based on the feature information of the scanning parameter and the adjustment process of the scanning parameter may be determined based on the classified result, which can help the device developers and/or device operators determine an optimal adjustment process of the parameters; (2) a variety of parameter adjustment controls have been designed for the touch screen interface, combined with the feature information of the scanning parameter, through the controls, the corresponding parameter can be better adjusted and good interface feedback can be obtained; (3) the parameter configuration interface of ultrasound imaging scanner has been optimized, and the display page has been reasonably partitioned, which can clarify the display and page flipping rules and obtain a more logical interface, resulting in using more conveniently; (4) after using the parameter adjustment process in the present disclosure, the operator can quickly find the position of the target parameter and adjust the scanning parameter based on the type of scanning parameter. The adjustment process is friendly and the feedback is intuitive, which effectively avoids the parameter search process, greatly improves the examination efficiency, and meets different user needs. It should be noted that different embodiments may produce different beneficial effects. In different embodiments, the possible beneficial effects may be any one or a combination of the above, or any other beneficial effect that may be obtained.

Figure 10:
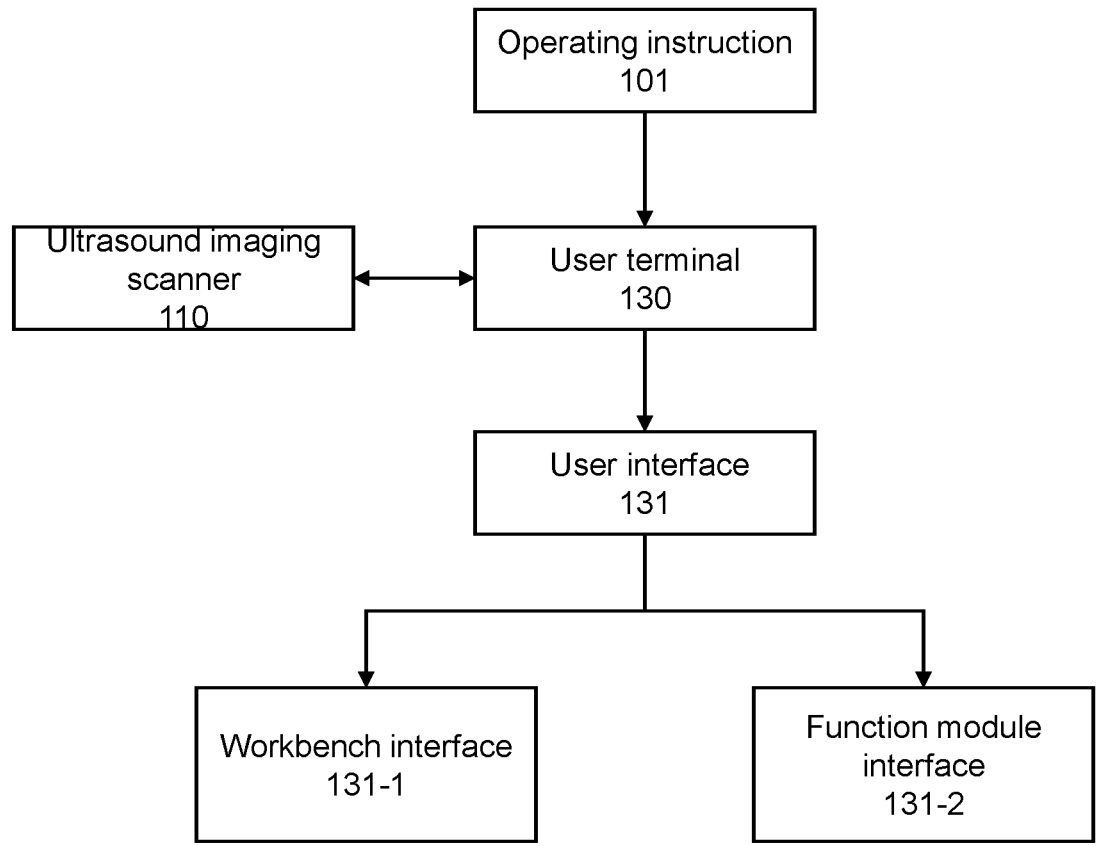
FIG. 10 is a schematic diagram illustrating an exemplary user interface representing a workbench interface or function modules according to some embodiments of the present disclosure.

FIG. 10 is a schematic diagram illustrating an exemplary user interface representing a workbench interface or function modules according to some embodiments of the present disclosure.

A system in some embodiments of the present disclosure may include an ultrasound imaging scanner 110 and a user terminal 130 in communication with the ultrasound imaging scanner. The user terminal 130 may include a user interface 131 implemented on the touch screen. In response to receiving an operating instruction 101, the user interface 131 may represent one of a workbench interface 131-1 or a function module interface 131-2.

More descriptions of the user interface, the touch screen, the user terminal, and the ultrasound imaging scanner may be found in FIG. 1 and related descriptions.

The operation instruction may include a relevant instruction for entering the workbench interface or the function module interface. More descriptions of the operation instruction and the obtaining the operation instruction may be found in FIG. 3 and related descriptions.

The function module interface 131-2 may be configured to facilitate an interaction between an operator and the ultrasound imaging scanner to cause or facilitate a function module corresponding to the function module interface 131-2 to perform one or more functions of the function module. Exemplary function modules of the ultrasound imaging scanner may include a patient management module, a clinic scene switch module, a probe switching module, a scanning parameter adjustment module, a measurement module, an annotation module, a review module, a reporting module, etc. Each of the function modules of the ultrasound imaging scanner may be configured to perform one or more functions. For example, the patient management module may be configured to manage patient information (e.g., information input, information modification, information deletion, etc.). The clinic scene module may be configured to switch different clinic scenes for ultrasound examination. The probe switching module may be configured to switch different probes for different ultrasound examination. The scanning parameter adjustment module may be configured to adjust scanning parameters. The measurement module may be configured to perform measurement (e.g., a size of a region of interest (ROI)) during the ultrasound examination. The annotation module may be configured to annotate ultrasound data (e.g., a measurement result). The review module may be configured to review ultrasound data (e.g., a measurement result, historical ultrasound image, etc.). The reporting module may be configured to generate a report based on the ultrasound data (e.g., a measurement result, historical ultrasound image, etc.).

In some embodiments, the function module of the ultrasound imaging scanner may include a parameter adjustment module, and one or more functions may include a parameter adjustment function of the multiple scanning parameter. The workbench interface may include a parameter adjustment region, and the parameter adjustment region may include multiple adjustment controls of the multiple scanning parameters. Each of the multiple adjustment controls may represent a target adjustment mode of the scanning parameters. The parameter adjustment module may refer to a function module used for parameter adjustment. The parameter adjustment function may be used to adjust the scanning parameters. More descriptions of the scanning parameter, the parameter adjustment region, the adjustment control, and the adjustment mode may be found in FIG. 3-FIG. 9 and related descriptions.

Figure 12:
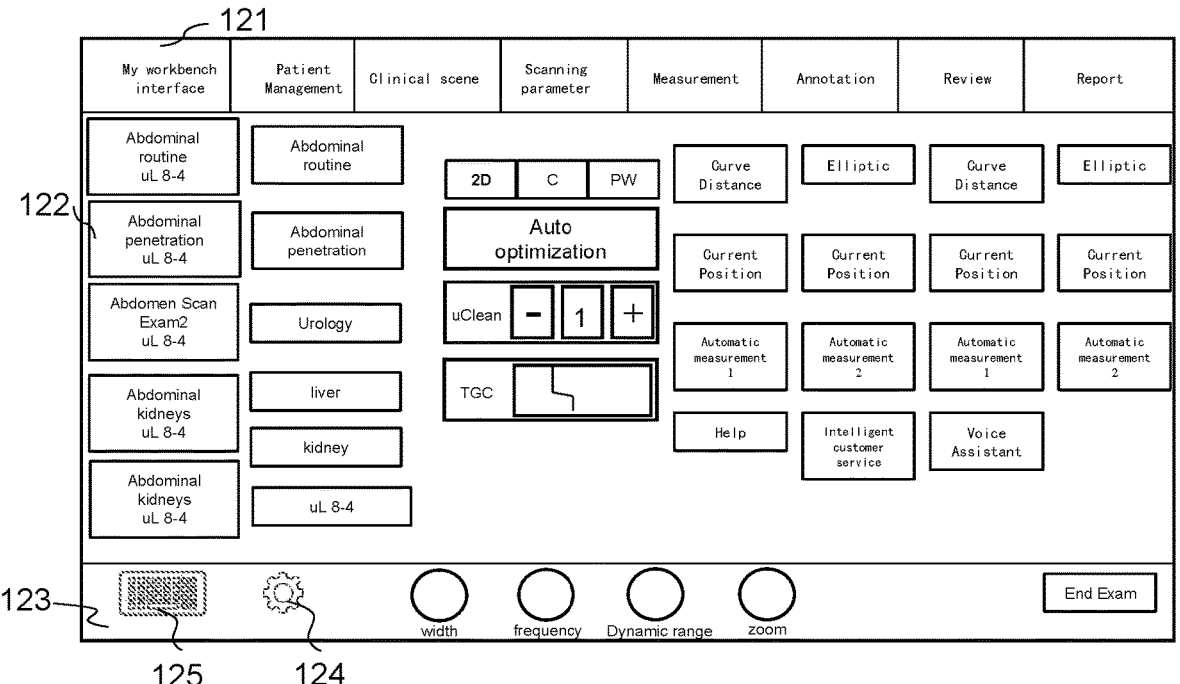
FIG. 12 is a schematic diagram illustrating an exemplary workbench imaging interface according to some embodiments of the present disclosure.

For example, the parameter adjustment module may include multiple adjustment functions of the scanning parameters, a display function, etc., such as a parameter display function achieved through the excitation type adjustment control and a parameter level adjustment function achieved through the gear adjustment control. As a further example, as shown in FIG. 12, the workbench interface may include a parameter adjustment region at a center of FIG. 12, and the parameter adjustment region may include an adjustment control corresponding to the scanning parameter such as TGC.

In some embodiments of the present disclosure, through the parameter adjustment module of the ultrasound imaging scanner and/or the parameter adjustment region on the workbench interface, the operator can quickly adjust the scanning parameter through the adjustment control, which helps to improve the efficiency of parameter adjustment. In some embodiments, the operator may adjust the scanning parameters by the multiple adjustment controls in the parameter adjustment region of the workbench interface.

In some embodiments, each of the function modules of the ultrasound imaging scanner may ultrasound examination correspond to a function module interface. In response to receipt of an operation instruction for entering a function module interface (i.e., the user interface represents or switches to the function module interface) corresponding to a function module, the processing device may cause the user interface to present the function module interface. An operator may interact with the ultrasound imaging scanner through the function module interface to facilitate a function module corresponding to the function module interface to perform one or more functions of the function module.

The workbench interface 131-1 may be configured to facilitate an interaction between an operator and the ultrasound imaging scanner to cause or facilitate the ultrasound imaging scanner to perform one or more functions from each of the one or more function modules. In other words, the workbench interface 131-1 may include an integration of functions from different function modules. For example, the workbench interface 131-1 may include an integration of functions from the clinic scene switch module, the probe switching module, the scanning parameter adjustment module, and the measurement module. As another example, the workbench interface 131-1 may include an integration of functions from the patient management module, the clinic scene switch module, the probe switching module, the scanning parameter adjustment module.

In some embodiments, the processing device may cause the user interface to display the workbench interface on the user interface based on the operation instruction of the user for entering the workbench interface. In some embodiments, the user interface may switch between the workbench interface 131-2 and the function module interface 131-1 according to an operation instruction. For example, the processing device may cause the user interface to switch from one of the functions interfaces to the workbench interface 131-2 based on the operation instruction of the operator for entering the workbench interface. As another example, the processing device may cause the user interface to switch from the workbench interface 131-2 to one of the functions interfaces based on the operation instruction of the operator for entering the function module interface. As a further example, the user interface may be configured to represent the function module interface for the parameter adjustment function in response to receipt of an operation instruction for entering the function module interface for the parameter adjustment function from the workbench interface. The function module interface for the parameter adjustment function may represent adjustment modes of multiple scanning parameters. In some embodiments, an adjustment mode of one of the multiple scanning parameters may be in a target configuration determined based on feature information of the scanning parameter according to process 300, 400, and/or 900 as described in the present disclosure. In some embodiments, after the user interface switches from the workbench interface to a function module interface, the user interface may return to the workbench interface automatically, for example, for a certain time interval after the user interface switches e to the function module interface, or after exiting from the function module interface.

The workbench interface 131-2 may be configured by an operator. For example, the operator may add one or more new functions to the workbench interface 131-2, delete one or more functions from the workbench interface 131-2, adjust positions of one or more functions on the workbench interface 131-2, etc. As another example, the operator may delete the workbench interface 131-2 from the user interface. Functions in the workbench interface 131-2 may be performed through other function module interfaces. As still another example, the workbench interface 131-2 may be set as a main interface of the touch screen-based adjustment mode. In some embodiments, after the workbench interface 131-2 is set as the main interface of the touch screen-based adjustment mode, if an operator switches to another function module interface and a function corresponding to the function module interface is performed or quit from the function module interface, the user interface may back to the workbench interface 131-2 automatically. For example, after the probe switch module performs probe switching, the user interface may back to the workbench interface 131-2 automatically. As another example, after the user interface is switched to the function module interface for the parameter function adjustment module and after the scanning parameter is adjusted, the user interface may back to the workbench interface 131-2 automatically. In some embodiments, when an operator operates on the workbench interface 131-2 for performing different functions, e.g., scanning parameter adjustment, measurement, annotation, etc., the workbench interface 131-2 may be not switched to other interface (e.g., the parameter adjustment interface, the measurement interface, the annotation interface, etc.). Accordingly, the workbench interface 131-2 may be shown to the operator for a long time, and other functions of the function modules maybe not affected. The operator may complete the ultrasound examination through the workbench interface 131-2, no switching between different function module interfaces needs for the ultrasound examination, thereby sampling the operation of the operation.

In some embodiments, multiple different workbench interfaces may be set by the same operator or different operators. As used herein, different workbench interface may refer to different configurations of the same workbench interface or different workbench interface (e.g., at different touch screen) in the same configurations or different configurations. For example, the same operator may configure the same workbench interface with different configurations corresponding to different scanning portions (e.g., the abdomen, the chest, a leg, etc.). As another example, different operators may configure different workbench interfaces on the same ultrasound imaging scanner or different ultrasound imaging scanners. In some embodiments, the workbench interface may be bound to an operator. The workbench interface bound to the operator may display completely content that the operator configures after the operator logs on to the ultrasound imaging scanner. In some embodiments, different operators may log to different workbench interfaces and the different workbench interfaces may be in different configuration (e.g., display different contents) to different operators (corresponding to different accounts). More descriptions for workbench interface configuration may be found in FIG. 19 and FIG. 20, and related descriptions. In some embodiments, in response to receiving the operation instruction for entering the workbench interface, the user interface may represent the workbench interface. The workbench interface may present a target configuration. The target configuration of the workbench interface may include one or more functions of each of different function modules of the ultrasound imaging scanner. An ultrasound examination may be performed based on the one or more functions of each of different function modules of the ultrasound imaging scanner. An operator may interact with the ultrasound imaging scanner to cause the ultrasound imaging scanner to perform the one or more functions through the workbench interface.

In some embodiments, the target configuration may include types of one or more functions of each of one or more different function modules of the ultrasound imaging scanner and/or arrangement of the one or more functions on the workbench interface. For example, the target configuration may include functions corresponding to each module of at least a portion of the clinical scene switch module, the probe preset switch module, the parameter adjustment module, the measurement module, the annotation module, etc. As a further example, the multiple functions of (or corresponding to) the probe switching module may include a probe switching function, a parameter preset switching function, and an overall probe parameter preset switching function. One or more of the probe switching function, the parameter preset switching function, and the overall probe parameter preset switching function may be integrated into the workbench interface. As still another example, functions of the parameter adjustment module may include functions of adjusting multiple scanning parameters. Functions of adjusting at least a portion of the multiple scanning parameters may be integrated into the workbench interface. In some embodiments, functions of at least two function modules may be integrated into the workbench interface.

In some embodiments, the target configuration may include an arrangement of one or more functions on the workbench interface. More descriptions of the arrangement of one or more functions on the workbench interface may be found in FIG. 12 and FIG. 15, and related descriptions.

In some embodiments, the target configuration of the workbench interface may be determined by an operator. The operator may determine the target configuration of the workbench interface according to different clinic scenes, scanning portions of the subject, scanning modes, personal habits, etc. In some embodiments, the target configuration of the workbench interface may be determined by the system 1000 according to different clinic scenes, scanning portions of the subject, scanning modes, personal habits, etc.

In some embodiments, by configuring the workbench interface with the target configuration including one or more functions from different function modules, the operator may quickly find the needed functions through the workbench interface, no switching between different function modules is needed when functions from different function modules are needed to perform an ultrasound examination, thereby improving ultrasound examination efficiency.

In some embodiments, different scanning subjects (e.g., a leg, a breast, a liver, a kidney, etc.) or clinical scene (e.g., the chest, the abdomen, etc.), or different scanning modes (e.g., B mode, PW mode, etc.) of scanning subjects may correspond to different target configurations. More descriptions of the scanning subject and the scanning mode may be found in FIG. 3 and related descriptions.

The clinical scene refers to a clinical scene in which the ultrasound examination is performed. The clinical scenes may be defined by a range of a subject under the ultrasound examination, such as the abdomen, the chest, etc. The scanning portions of a subject may refer to different portions in a clinical scene. For example, in the clinical scene of the abdomen, the scanning portions may include a liver, a kidney, a blood vessel, etc. In the clinical scene of the chest, the scanning portions may include the heart, the blood vessel, etc.

Figure 19:
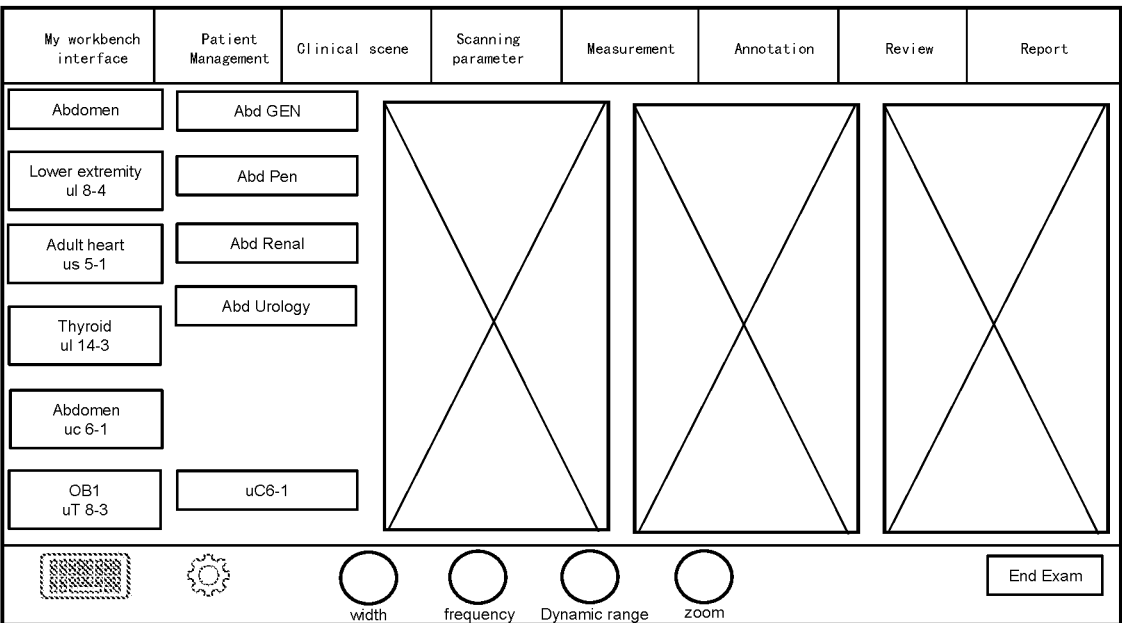
FIG. 19 is a schematic diagram illustrating an exemplary workbench interface according to some embodiments of the present disclosure.
Figure 20:
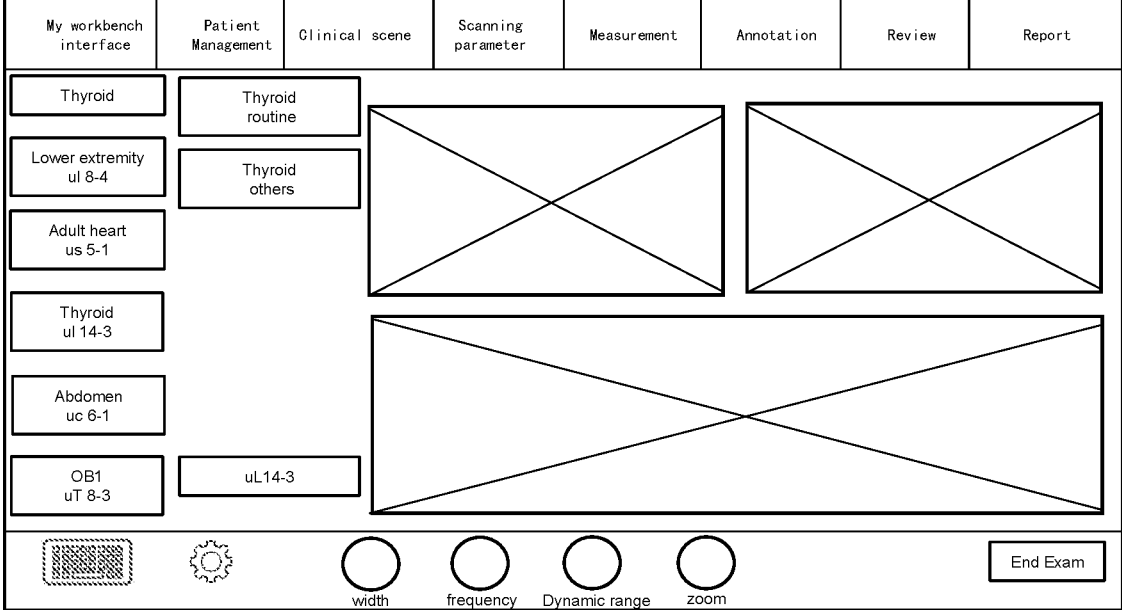
FIG. 20 is a schematic diagram illustrating another exemplary workbench interface according to some embodiments of the present disclosure.

For example, when the abdomen of the scanning subject receives the ultrasound examination, the target configuration of the workbench interface may include function controls required for the ultrasound examination of the abdomen, the target configuration of the workbench interface. As a further example, as shown in FIG. 19, the target configuration of the workbench interface shown in FIG. 19 include function controls required for the ultrasound examination of the abdomen, scanning parameters that need to be adjusted during the ultrasound examination of the abdomen, such as parameter adjustment controls, a measurement function control, an annotation control, a review control, etc. When the thyroid of the scanning subject receives the ultrasound examination, the target configuration may include function controls required for the ultrasound examination of the thyroid, the target configuration of the workbench interface shown in FIG. 20 includes function controls required for the ultrasound examination of the thyroid, such as parameter adjustment controls, a measurement function control, an annotation control, etc. More descriptions of the function controls may be found in FIG. 12 and related descriptions. As shown in FIGS. 19 and 20, for different ultrasound examinations of different scanning portions of a subject, the operator may set different configuration of the workbench interface. In addition, for the same ultrasound examination of the same portion of different subjects, different operators may set different target configurations for the workbench interface according to their own habits.

In some embodiments, different scanning modes of the same scanning portion may correspond to different target configurations. For example, the target configuration of the workbench interface under a first scanning mode may include one or more functions of each of a first portion of function modules of the ultrasound imaging scanner, such as the patient management module, the clinic scene switch module, the probe switching module, the scanning parameter adjustment module, the measurement module, the annotation module, the review module, the reporting module, etc. The target configuration of the workbench interface under a second scanning mode may include one or more functions of each of a second portion of function modules of the ultrasound imaging scanner, such as the patient management module, the clinic scene switch module, the probe switching module, the scanning parameter adjustment module, the measurement module, the annotation module, the review module, the reporting module, etc. Functions in the first portion and the second portion may be partially different. Functions, integrated into the target configuration, of the same function module in the first portion and the second function may be partially different. For example, scanning parameters under the first scanning mode may be different from scanning parameters under the second scanning mode, and an arrangement of adjustment controls of the scanning parameters under the first scanning mode may be different an arrangement of adjustment controls of the scanning parameters under the second scanning mode.

Figure 21:
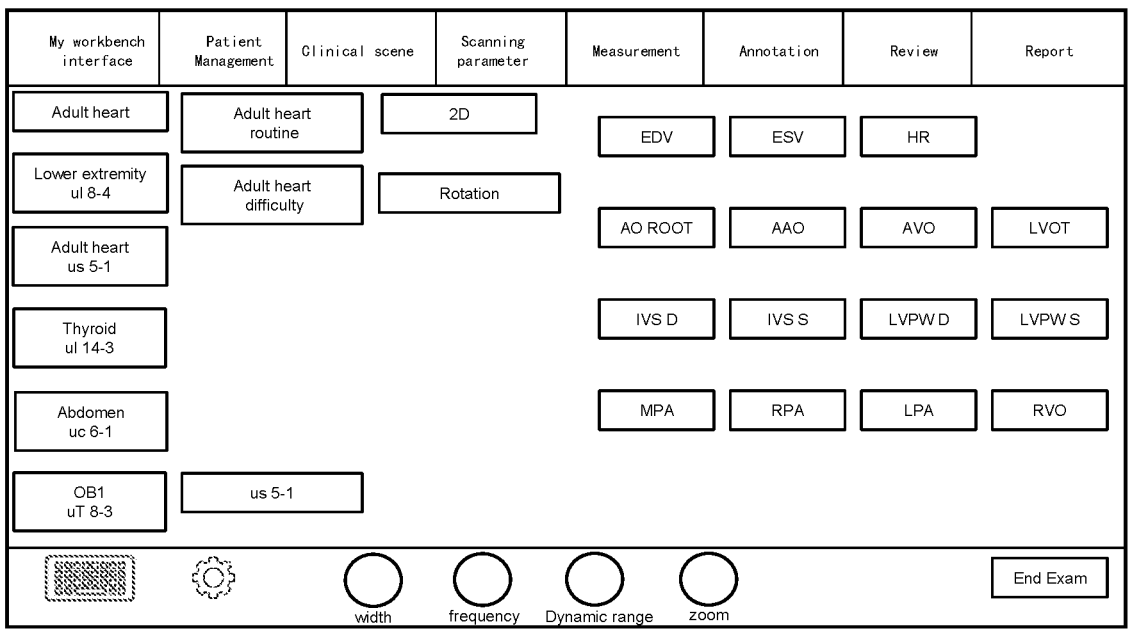
FIG. 21 is a schematic diagram illustrating an exemplary workbench interface under a two-dimension (2D) model according to some embodiments of the present disclosure.
Figure 22:
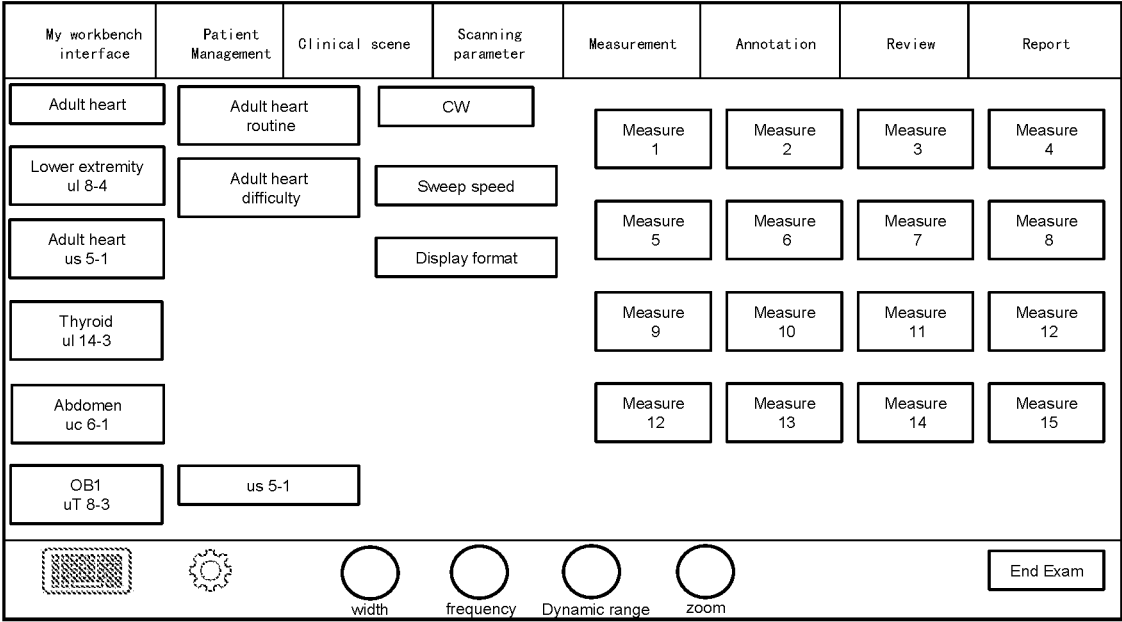
FIG. 22 is a schematic diagram illustrating an exemplary workbench interface under a CW model according to some embodiments of the present disclosure.

As a further example, the target configuration under 2D mode of the heart ultrasound examination may be shown in FIG. 21. The target configuration e under CW mode of the heart ultrasound examination may be shown in FIG. 22. As shown in FIG. 21, the target configuration under2D mode of the heart ultrasound examination may include the functions required under 2D mode, such as relevant annotation (e.g., indicators) for the ultrasound examination (e.g., EDV, HR, etc.); as shown in FIG. 22, the target configuration under CW mode of the heart ultrasound examination include functions required under CW mode, such as multiple measurement operations.

In some embodiments, through different clinical scenes, different scanning subjects, or different scanning modes of scanning subjects corresponding to different target configurations, the operator may perform the ultrasound examination on the workbench interface that is suitable for the current clinical scene, the scanning subject, and/or the scanning mode, which can improve the flexibility of the workbench interface, adapt to different examination needs, and improve the user experience.

In some embodiments, the target configuration of the workbench interface may be determined by an operator. For example, the operator may input an operation instruction for configuring the workbench interface (e.g., entering a configuration interface). The user interface may represent a configuration interface through which the operator may configure the workbench interface. The operator may input one or more operation instructions through the configuration interface. Each of the one or more operation instructions may include configuration information (e.g., the functions from each of one or more function modules, positions of the functions) of the workbench interface. In some embodiments, the configuration interface may provide one or more candidate configurations. The operator may determine and/or modify one of the candidate configuration from the one or more candidate configurations as the target configuration.

In some embodiments, the processing device may determine the target configuration and/or the one or more candidate configurations based on the scanning portions, clinical scene, scanning modes, and/or personal operations of the operator. More descriptions for configuration of the workbench interface may be found in FIG. 11 and related descriptions.

Figure 11:
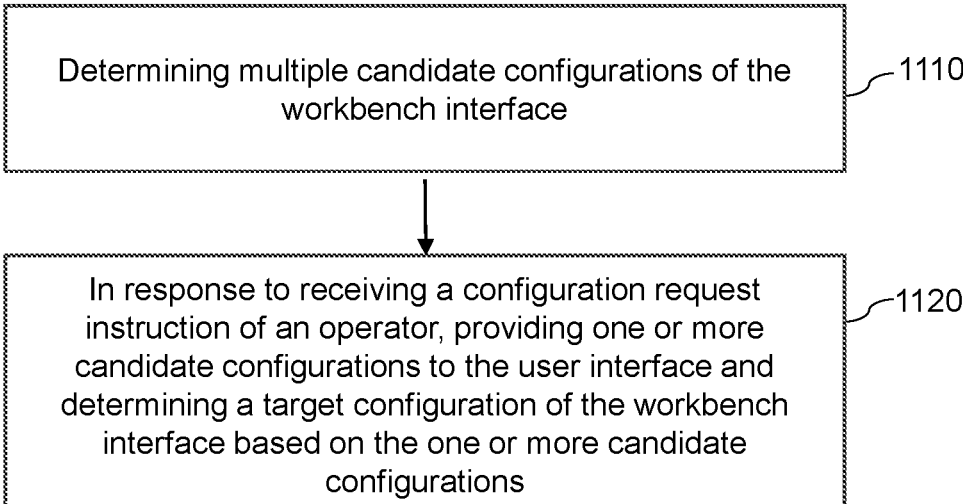
FIG. 11 is a flowchart illustrating an exemplary process of determining a target configuration based on candidate configurations according to some embodiments of the present disclosure.

FIG. 11 is a flowchart illustrating an exemplary process of determining a target configuration according to some embodiments of the present disclosure. In some embodiments, the process 1100 may be executed by a processor. As shown in FIG. 11, the process 1100 may include the following operations:

In 1110, multiple candidate configurations of the workbench interface may be determined.

A candidate configuration may include relevant configuration information of the workbench interface. For example, a candidate configuration may include one or more candidate functions of each of the different function modules of the ultrasound imaging scanner. In some embodiments, each of the multiple candidate configurations may include one or more candidate functions and/or candidate arrangement of the one or more candidate functions on the workbench interface. More descriptions of the function module and functions of the function module may be found in FIG. 10 and related descriptions.

In some embodiments, the processing device may determine the candidate configurations in various ways. For example, the processing device may determine a historical configuration with a highest usage frequency in historical operations as a candidate configuration based on the historical operation, more descriptions of the historical operation may be found in the following descriptions of FIG. 11.

In some embodiments, the processing device may determine the candidate configurations based on at least one of personalized information of operators, the historical operations of the operators, the clinical scenes, the scanning subjects, or the scanning modes for the scanning subjects. More descriptions of the operators, the scanning subjects, and the scanning modes may be found in FIG. 3 and FIG. 10 and related descriptions thereof.

A historical operation of an operator may include operation information of the operator using the workbench interface. For example, the historical operation of the operator may include a historical arrangement of one or more functions determined by the operator on the workbench interface and functions used in the historical ultrasound examination, or the like.

In some embodiments, the processing device may obtain the historical operations of the operators from the terminal device (e.g., the user terminal 130), the storage device (e.g., the storage device 140), or the ultrasound imaging scanner (e.g., the ultrasound imaging scanner 110). In some embodiments, the processing device may identify one or more functions in the historical operations of the operators template in ultrasound examinations of the same scanning portion under the same scanning mode with a usage frequency being greater than the usage frequency threshold as candidate functions in a candidate configuration corresponding to the scanning portion under the scanning mode, and an arrangement or a random arrangement of the one or more functions may be designated as a candidate arrangement of the candidate configuration based on a preset rule. The frequency threshold may be preset based on actual situations. In some embodiments, the processing device may determine a candidate configuration based on the clinical scene and the scanning mode by querying a preset table, and the preset table may include a corresponding relationship between the clinical scenes, the scanning modes, and the candidate configurations. The preset table may be obtained based on the historical data of ultrasound examinations.

In some embodiments, by determining the candidate configurations through at least one of the operators, the historical operations of the operators, the clinical scenes, the scanning subjects, and/or the scanning modes for the scanning subjects, multiple factors may be combined to determine the candidate configurations that are more in line with the actual scenes and satisfy the needs of the operator, which helps to determine the target configuration more accurately.

In some embodiments, the processing device may use a trained machine learning model (also referred to as a second trained machine learning model) to determine the multiple candidate configurations based on at least one of personalized information of the operators or subjects to be scanned, the historical operations of the operators, the clinical scenes, the scanning subjects, the scanning modes for the scanning subjects, or the scanning results (e.g., ultrasound images).

The machine learning model may be a trained model for determining a configuration template or a target configuration.

The trained machine model may be trained based on a large count of training samples (also referred to as second training samples) with a label (also referred to as second label). In some embodiments, a training sample may include personalized information of sample operators or subjects being scanned, historical operations of sample operators, sample clinical scenes, sample scanning subjects, and scanning modes of sample scanning subjects. The training samples may be obtained based on the historical data. The label may be a historical candidate configuration corresponding to the training sample, and the label may be manually labeled.

A training process of the machine learning model may be same as the training process of the first trained machine learning model, more descriptions may be found FIG. 3 and related descriptions.

In some embodiments, the multiple candidate configurations may be determined through the machine learning model, which can utilize a self-learning ability of machine learning to find patterns in a large amount of data and determine the multiple candidate configurations that are more in line with operator and actual needs.

In 1120, in response to receiving a configuration request instruction of an operator, one or more candidate configurations may be provided to the user interface and a target configuration of the workbench interface may be determined based on the one or more candidate configurations. In 1130, an ultrasound imaging scanner (e.g., the workbench interface) may be configured based on the target configuration.

In some embodiments, in response to receiving the configuration request instruction of the operator, the processing device may interact with the user interface through the network and transmit the one or more candidate configurations to the user interface.

In some embodiments, the operator may determine a target configuration based on the multiple candidate configurations.

In some embodiments, the processing device may display the multiple candidate configurations in response to receiving an operation to configure the workbench interface from the operator; the processing device may determine a target configuration from the multiple candidate configuration in response to receiving an operation instruction of selecting a target configuration from the operator. The target configuration of the workbench interface based on the target configuration. For example, the operator may adjust the target configuration to determine the target configuration. As a further example, the operator may add or delete one or more functions to the target configuration. As another example, the operator may adjust positions of one or more functions in the target configuration.

In some embodiments, the operator may configure the workbench interface and/or select a configuration template through the operation instruction. For example, the operator may configure the workbench interface or select a configuration template by clicking, double-clicking, and other operation instructions.

In some embodiments, the operator may configure the workbench interface and/or select a configuration template through function controls, more descriptions may be found in FIG. 12 and related descriptions.

In some embodiments, the processing device may determine the target configuration based on the operation instruction. For example, the processing device may use the candidate configuration clicked by the operator as a target configuration. In some embodiments, the operator may configure the workbench interface through the user interface, and the processing device may display the multiple candidate configurations on the user interface in response to receiving the operation of selecting the configuration template from the operator. In some embodiments, the operator may select a desired configuration template through the user interface, and the processing device may determine a candidate configuration corresponding to the selected configuration template as a target configuration in response to receiving the operation of selecting the configuration template from the operator.

In some embodiments, the multiple candidate configurations may be displayed after receiving the operation of configuring the workbench interface from the operator. After receiving the operation of selecting the configuration template from the operator, the target configuration may be determined from the multiple configuration templates, which not only displays the multiple candidate configuration to the operator for selection, but also enables the operator to quickly select the desired candidate configurations, resulting in improving the efficiency of determining the target configuration and making the target configuration more user-friendly.

In some embodiments, the processing device may modify the target configuration selected by the operator based on the operation instruction of the operator for modifying the target configuration, thereby determining the target configuration. The operation instruction for modifying configurations refers to an operation instruction used to modify the candidate configuration.

For example, the operator may modify an arrangement of functions in the target configuration through the operation instruction, and/or modify the functions in target configuration (e.g., deletion, addition, modification, etc.).

In some embodiments, the processing device may control the function controls on the workbench interface to be in an updatable state in response to receiving the operation instruction for modification from the operator The workbench interface may be displayed on the user interface of the touch screen-based adjustment mode, and the processing device may control the multiple function controls on the workbench interface to be in an updatable state in response to receiving the operation instruction for modification from the operator, i.e., making all function controls on the workbench interface in a state that can be modified, deleted, added, or moved. The operation instruction inputted by the operator to modify the target configuration may be a long press operation at any position on the workbench interface; or a click or slide operation on a configuration control (e.g., an activation control) of the workbench interface.

In some embodiments, the processing device may adjust (or update) a function control in response to receiving a trigger operation on the function control in an updatable state. If multiple function controls on the workbench interface are in an updatable state, the processing device may update one of the multiple function controls in response to the trigger operation on the function control in the updatable state. In some embodiments, a function control in an updatable state may include a deletion mark (e.g., at an upper right corner of the function control), and the processing device may achieve a deletion of the function control in response to an operation of clicking the deletion mark for the function control from the operator. In some embodiments, the processing device may achieve a modification of the function control in response to an operation of modifying the function control from the operator. In some embodiments, the ultrasound imaging scanner may include a function library, and the processing device processing device may select a new function in the function library to replace the function of the feature control or add a new function in the function control in response to the operation of deleting or adding the function control from the operator.

In some embodiments, the processing device may control the function control on the workbench interface to be in an updatable state for the operator to update the function control in response to the operation of deleting the configuration from the operator, which allows the operator to update the function control on the workbench interface according to the own work habits, making it more efficient for the operator to perform the ultrasound examination using an updated workbench interface.

In some embodiments, the operator may modify the candidate configuration selected by the operator by inputting the operation instruction for modifying the configuration through the user interface. After receiving the operation instruction for modifying the configuration, the processing device may determine the target configuration modified by the operator as the target configuration.

In some embodiments, the one or more candidate configurations may be modified through the instruction of the operator to determine the target configuration, which can make the target configuration more in line with operator habits and actual needs. In an actual ultrasonic scanning process, the efficiency of the operator performing the ultrasonic examination can be improved based on the workbench interface.

In some embodiments, by providing the operator with the multiple candidate configurations, the operator can quickly select the target configuration that is suitable for the current ultrasound scan based on the provided candidate configurations. While saving operators time, the requirements for workbench interface configuration can be satisfied, which can better adapt to the habits of the operator, and improve the operator experience.

FIG. 12 is a schematic diagram illustrating an exemplary workbench interface according to some embodiments of the present disclosure.

In some embodiments, each of one or more functions may be implemented through a control (also referred to as a function control). More descriptions for functions may be found in FIG. 10 and related descriptions. The control corresponding to a function may be used to cause the ultrasound imaging scanner to perform a function corresponding to the control based on an operation on the control.

In some embodiments of the present disclosure, the workbench interface may include a navigation region and a control display region. The navigation region may be configured to display labels of multiple function modules, and the control display region may be configured to display controls for each function in multiple function modules. The workbench interface may be reasonably partitioned for operator convenience.

For example, as shown in FIG. 12, the workbench interface may include a navigation region 121 and a control display region 122.

In some embodiments, the navigation region 121 may be configured to provide entrances of function modules (or function model interface) and the workbench interface. The function modules may be entered through the entrances of the function modules. The entrances of the function modules may be displayed in the navigation region 121 as labels of multiple function modules. As shown in the navigation region 121 at the top of FIG. 12, the labels may represent entrances of the workbench interface (i.e., the my workbench interface), the patient (i.e., the scanning subject) management module, the clinical scenes switching module, the scanning parameter adjustment module, the measurement module, the annotation module, the review module, and the report module.

In some embodiments, the control display region 122 may be configured to display one or more controls for each function in multiple function modules. For example, when performing the ultrasound examination on the abdomen of the scanning subject, as shown in FIG. 12, a left region of the control display region 122 may display a corresponding control for an examination item (e.g., abdomen routine, abdomen penetration, abdomen kidney, Abdomen Scan Exanm2, etc.) included in the abdomen examination and a corresponding probe for each examination item. The control display region 122 may also display controls of scanning modes (e.g., the 2D mode) corresponding to each examination item and adjustment controls of scanning parameters of the parameter adjustment module, such as auto optimization, uclean, TGC, etc., in a middle region of the control display region 122. The right region in the control display region 122 may display the function controls of functions corresponding to the measurement module and the annotation module under 2D mode of the abdomen penetration. For example, the function control may include a curve distance, a current position, an automatic measurement, or the like. The bottom region of the control display region 122 may display adjustment controls of scanning parameters of the parameter adjustment module, such as width, frequency, dynamic range, zoom, etc. It should be noted that controls and arrangement of the controls in FIG. 12 is merely an example, the target configuration of the workbench interface may be in other forms.

In some embodiments, the control may also be referred to as a function control, and a function control may be configured to integrate one or more functions.

Figure 15:
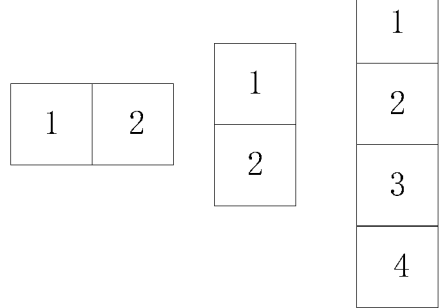
FIG. 15 is a schematic diagram illustrating an exemplary arrangement of the one or more function controls according to some embodiments of the present disclosure.

FIG. 15 is a schematic diagram illustrating an exemplary arrangement of the one or more function controls according to some embodiments of the present disclosure. As shown in images (a), (b), (c), (d), and (e) of FIG. 15, the workbench interface may include multiple cells (e.g., 2, 4, 9, etc.) of the same size or different sizes divided based on pixels. Each cell may be filled with different function controls. In some embodiments, the cells may be arranged regularly. For example, the cells may be arranged as a matrix (e.g., 2*1, 1*2, 1*4, 2*2, 3*3, etc.) In some embodiments, the cells may be arranged irregularly. In some embodiments, the workbench interface may include a control configured to trigger a first operation interface to work. The first operation interface may be configured for selecting the workbench interface.

In some embodiments, the first operation interface may include multiple first controls. Each of the first controls may correspond to a workbench interface. The first control corresponding to a workbench interface may be configured to trigger the workbench interface to work. The count of the first controls may be the same as the count of workbench interfaces, each of the first controls in the multiple first controls may correspond to one of the multiple workbench interfaces. Each workbench interface in the multiple workbench interfaces may correspond to one of multiple ultrasound examination tasks.

Figure 13:
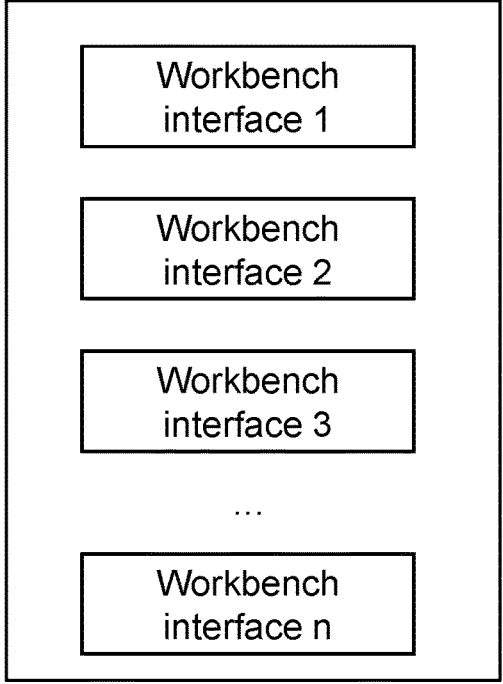
FIG. 13 is a schematic diagram illustrating an exemplary first operation interface according to some embodiments of the present disclosure.

FIG. 13 is a schematic diagram illustrating an exemplary first operation interface according to some embodiments of the present disclosure. As shown in FIG. 13, the first operation interface may include n first controls, and the operator may select one of the first controls on the first operation interface. The user interface may display the workbench interface corresponding to the first control selected by the operator. In some embodiments, the operator may select the first control on the first operation interface through the operation instruction.

If the count of the workbench interfaces corresponding to an operator is one, the processing device may display the workbench interface in response to receiving the operation instruction of displaying the workbench interface. If the count of workbench interfaces corresponding to the operator exceeds one, the processing device may rank the multiple workbench interfaces corresponding to the operator according to a priority. The processing device may display a workbench interface with a highest priority among the multiple workbench interfaces corresponding to the operator in response to receiving the operation instruction of displaying the workbench interface. The workbench interface with the highest priority may be a workbench interface corresponding to the operator.

In some embodiments, the processing device may display a corresponding workbench interface of the operator in response to the click operation of the operator. That is to say, when the operator performs a click operation on the user interface, the processing device may display the workbench interface in response to the click operation of the operator. This way, without the need for the operator to log in, the workbench interface may be displayed by clicking directly, which is very convenient and fast. In some embodiments, the priority configuration of the multiple workbench interfaces corresponding to the operator by the processing device may be set based on the count of times multiple workbench interfaces are used. The processing device may periodically update the priority configuration of the multiple workbench interfaces corresponding to the operator.

In some embodiments, a user login interface may be first displayed on the user interface. The operator may input login information on the user login interface, and the processing device may display the first operation interface of the operator on the user interface in response to the login information.

In some embodiments, the processing device may display the workbench interface corresponding to the first control in response to receiving an operation of selecting the first control from the operator. After displaying the first operation interface on the user interface, the processing device may display the workbench interface corresponding to the first control selected by the operator in response to receiving the operation of selecting the first control from the operator. The operation of selecting the first control from the operator refers to a user clicking operation on the first control among the multiple first controls on the first operation interface. The first control may correspond to the workbench interface.

In some embodiments of the present disclosure, the processing device may display the first operation interface in response to receiving the instruction from the operator, which facilitates the operator to select the first control corresponding to the ultrasound examination and display the workbench interface required to perform the ultrasound examination. The ultrasound examination process has a high practicality and can improve the efficiency of performing the ultrasound examination.

In some embodiments of the present disclosure, based on the first operation interface, the operator may choose the first control corresponding to the execution of the ultrasound examination to display the workbench interface required for performing the ultrasound examination, making the workbench interface more practical and improving the efficiency of performing the ultrasound examination.

In some embodiments, the workbench interface may include the control configured to trigger a second operation interface. The second operation interface may be configured for configuring the workbench interface. The second operation interface of the workbench configuration interface refers to an operation interface configured to configure the workbench interface.

As shown in FIG. 12, the control 124 of the workbench configuration interface may trigger a second operation interface for inputting the workbench configuration interface. The operator may trigger the control 124 of the workbench configuration interface through the operation instruction on the user interface. In response to receiving the operation instruction, the processing device may display the second operation interface.

In some embodiments, the second operation interface may provide the multiple candidate configurations for the workbench interface. More descriptions of the multiple candidate configurations of the workbench interface may be found in FIG. 11 and related descriptions.

In some embodiments, the second operation interface may be suspended above the control display region. In some embodiments, the second operation interface may occupy the control display region, i.e., the second operation interface may be displayed in the control display region.

In some embodiments, the processing device may display the second operation interface in response to receiving an operation of triggering the control configured to trigger the second operation interface from the operator. The processing device may display the second operation interface in response to receiving the operation of triggering the control configured to trigger the second operation interface from the operator. The second operation interface may be suspended and displayed above the control display region, or the control display region with the multiple function controls may be replaced by the second operation interface, that is, the second operation interface may be displayed in the control display region. The triggering operation for the control configured to trigger the second operation interface may be a click operation or a double-click operation.

In some embodiments, the processing device may update the workbench interface in response to receiving an operation of configuring the workbench interface from the operator. When the second operation interface is displayed on the user interface, the processing device may update the workbench interface in response to receiving the operation of configuring the workbench interface from the operator, that is, updating the control display region of the multiple function controls corresponding to the previously displayed multiple functions in the workbench interface. The updating process for the workbench interface may be to update the arrangement (i.e., the position) of the multiple function controls on the control display region, or to update (e.g., delete, add, modify) the function controls on the control display region. The specific updating process may not be limited in the embodiments, as long as the function can be implemented.

As shown in FIG. 12, the control for triggering the second operation interface may be displayed in a function bar 123 of the workbench interface, and the function bar 123 refers to a function region configured to implement functions of the workbench interface.

In some embodiments of the present disclosure, by using the controls for triggering the second operation interface, the operator may display the second operation interface by triggering the control. Based on the second operation interface, the operator may update the workbench interface, making the updated workbench interface more in line with the usage habits, thereby improving the efficiency of the operator performing the ultrasound examination based on the workbench interface.

In some embodiments, the second operation interface may include a target configuration of the multiple workbench interfaces, which involves an implementation method of updating the workbench interface in response to a configuration operation on the second operation interface, including:

In response to an operation of selecting the target configuration of the multiple workbench interface, a target workbench interface may be update based on the target configuration.

When the second operation interface is displayed on the user interface, the processing device may determine the target configuration in response to receiving the operation of selecting the candidate configurations for the multiple workbench interfaces on the second operation interface. The configuration on the workbench interface may be updated based on the target configuration. The operation of the selecting the candidate configurations for the multiple workbench interfaces on the second operation interface may be a click operation on one of the candidate configurations on the multiple workbench interfaces, and the candidate configuration is the target configuration.

In some embodiments of the present disclosure, the second operation interface may include preset multiple candidate configurations of the multiple workbench interfaces. The operator may directly select the target configuration from the multiple candidate configurations to update the workbench interface, making the ultrasound examination process provided in the embodiments practical. Moreover, the target user does not need to set the target configuration, which can improve the efficiency of performing the ultrasound examination.

In some embodiments of the present disclosure, by configuring the control to trigger the second operation interface for inputting the workbench configuration interface, the operator may display the second operation interface through the control. Based on the second operation interface, the operator may determine the target configuration of the workbench interface, making the workbench interface more in line with the usage habits and needs of the operator, thereby improving the efficiency of the operator performing the ultrasound examination based on the workbench interface.

In some embodiments, the workbench interface may include a control configured to trigger a third operation interface representing a virtual keyboard for input. The third operation interface refers to a user interface that includes a virtual keyboard.

In some embodiments, the processing device may display the virtual keyboard on the workbench interface in response to receiving an operation of triggering the control 125 of the virtual keyboard. The processing device may display the virtual keyboard on the workbench interface in response to the operation of triggering the control 125 of the virtual keyboard from the operator. The virtual keyboard may be suspended above the workbench interface. The operation of triggering the control 125 of the virtual keyboard may be a click operation.

As shown in FIG. 12, the control 125 may trigger a third operation interface representing the virtual keyboard used for input. An operator may trigger the control 125 through performing an operation on the control 125. For example, the operator may click the control 125 to trigger the control

125, such that the third operation interface may be triggered to work. In some embodiments, the virtual keyboard may be suspended above the workbench interface.

In some embodiments of the present disclosure, the processing device may display the virtual keyboard in response to receiving the operation of triggering the control 125 of the virtual keyboard on the workbench interface from the operator, which can facilitate the operator to operate on the virtual keyboard and input a corresponding parameter on the workbench interface, thereby making the ultrasound examination provided in the embodiment practical.

In some embodiments of the present disclosure, by triggering the control representing the third operation interface of the virtual keyboard used for input, the processing device may display the virtual keyboard in response to receiving the operation instruction of the operator, making it convenient for the operator to operate on the virtual keyboard and input a scanning parameter on the workbench interface, which helps to improve the practicality of the ultrasound imaging scanner.

In some embodiments, the control display region may include multiple controls for selecting a scanning mode, and the target configuration may include function controls corresponding to functions of different function modules under the target scanning mode. More descriptions of the scanning mode may be found in FIG. 3 and related descriptions, more descriptions of the control display region may be found in FIG. 12 and related descriptions, more descriptions of the target configuration may be found in FIG. 10 and related descriptions. The target scanning mode refers to a scanning mode used by the ultrasound imaging scanner for the ultrasound examination.

As shown in FIG. 12, a middle region of the control display region may include multiple controls for selecting the multiple scanning modes for ultrasound examination. For example, the multiple controls may include controls corresponding to 2D mode, C mode, and PW mode.

In some embodiments, the processing device may determine the scanning mode selected by the operator as a target scanning mode in response to receiving an operation instruction for selecting a scanning mode generated by the operator through the workbench interface. In some embodiments, in response to selecting the target scanning mode, the control display region may display the function controls corresponding to the functions of different function modules under the target scanning mode.

In some embodiments, the control display region may further include multiple controls for selecting the scanning mode. As shown in FIG. 12, there are multiple controls for selecting the scanning mode for the ultrasound examination in the middle region of the control display region, such as the 2D mode, the C mode, and the PW mode. When the control display region includes the multiple controls for selecting the scanning mode, in some embodiments, the processing device may display the function controls of functions under the target scanning mode on the control display region in response to receiving the operation instruction of triggering the control representing the target scanning mode in the multiple controls for scanning mode selection.

The processing device may display the function controls of functions under the target scanning mode in the control display region in response to the operation of triggering the control representing the target scanning mode from the operator. That is to say, the function controls of functions under the target scanning mode may be displayed below the control used to select the scanning mode in the control display region. The function control refers to a function control for various parameters required for the target scanning mode. The operation of triggering the control used to select the scanning mode from the operator may be a click operation.

In some embodiments of the present disclosure, the control display region may include controls used to select the scanning mode. When the parameters in different scanning modes need to be updated for the ultrasound examination, the multiple scanning modes may be switched under a current workbench interface, thereby improving the efficiency of performing the ultrasound examination.

In some embodiments of the present disclosure, the control display region may include multiple controls used to select the scanning mode. When the parameters in different scanning modes need to be updated for the ultrasound examination, the multiple scanning modes may be switched under the current workbench interface, thereby improving the efficiency of executing ultrasound examination.

In some embodiments, the workbench interface may include a taskbar, and the taskbar may include multiple examination items, and the target configuration may include function controls corresponding to the functions of different function modules under a target examination item. The taskbar refers to a long bar region on the workbench interface used to display the multiple examination items. The examination item refers to an ultrasound examination content performed by the ultrasound imaging scanner, such as abdominal routine, abdominal penetration, or the like. The target examination item may be an ultrasound examination item determined to be performed by the ultrasound imaging scanner.

As shown in FIG. 12, a leftmost region of the control display region 120 is the taskbar. The multiple examinations displayed in the taskbar are the multiple examination items during the ultrasound examination. The ultrasound imaging scanner may receive a selection operation for an examination item generated by the operator via the function control corresponding to the examination item, determine a target examination item, and display the function controls of functions corresponding to one or more of multiple function modules required for the target examination item in the right region of the control display region. For example, the function controls of functions corresponding to one or more of multiple function modules required for the target examination item may include a function control corresponding to the probe required for the target examination item, a functional control corresponding to the measurement required for the target ultrasound examination item, or the like.

In some embodiments of the present disclosure, for different ultrasound examination items, the workbench interface may display corresponding function controls of the ultrasound examination device, which can improve the efficiency of performing the ultrasound examination project and thus improve the efficiency of performing the ultrasound examination.

In some embodiments of the present disclosure, for different examination items, the workbench interface may display the function controls corresponding to the examination items, which can improve the efficiency of performing the ultrasound examination, thereby improving the efficiency of performing the ultrasound examination, and also improving the convenience of the operator switching between different examination items, resulting in improving the operator experience.

In some embodiments, the workbench interface may include a taskbar, and the taskbar may include multiple examination tasks. The target configuration may include function controls corresponding to the functions of different function modules under the target examination task. The examination task refers to an ultrasound examination task performed by the ultrasound imaging scanner, such as lower limb blood vessels, mid to late pregnancy, or the like. The target examination task refers to an ultrasound examination performed by the ultrasound imaging scanner.

After displaying a corresponding workbench interface on the user interface, the processing device may perform the ultrasound examination task in response to receiving a trigger operation of triggering the one or more function controls on the workbench interface from the operator. The operation of triggering the one or more function controls on the workbench interface from the operator may be a click operation, a double click operation, a sliding operation, an input operation, or the like. The operation of triggering the one or more function controls by the target user may be related to the ultrasound examination task. A sequence of the operation of triggering the function control and the count of triggered function controls may be related to a workflow of the ultrasound examination, which may not be limited herein.

The ultrasound examination method provided in the embodiments of the present disclosure may include in response to the triggering operation from the operator, a corresponding workbench interface of the operator may be displayed, the workbench interface may include function controls corresponding to the multiple function configurations required for the ultrasound examination; in response to the operation of triggering at least one function control on the workbench interface, the ultrasound examination may be performed. In some embodiments, the workbench interface corresponding to the operator may display all the function controls corresponding to the required function configuration for the ultrasound examination. The operator may directly trigger one or more function controls on the workbench interface to perform the entire ultrasound examination without the need for frequent switching between interfaces corresponding to multiple function configurations, which can improve the efficiency of performing the ultrasound examination. Moreover, all the function controls displayed on the workbench interface may be required for performing the ultrasound examination without the need for the target user to search based on professional knowledge, which can avoid the situation where the function controls required for performing the ultrasound examination cannot be found, thereby improving the efficiency of performing the ultrasound examination.

Figure 17:
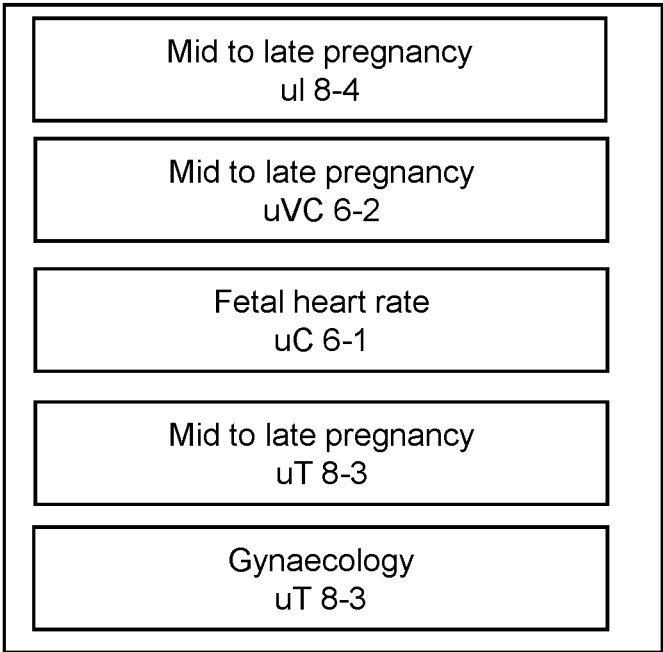
FIG. 17 is a schematic diagram illustrating an exemplary function control according to some embodiments of the present disclosure.
Figure 18:
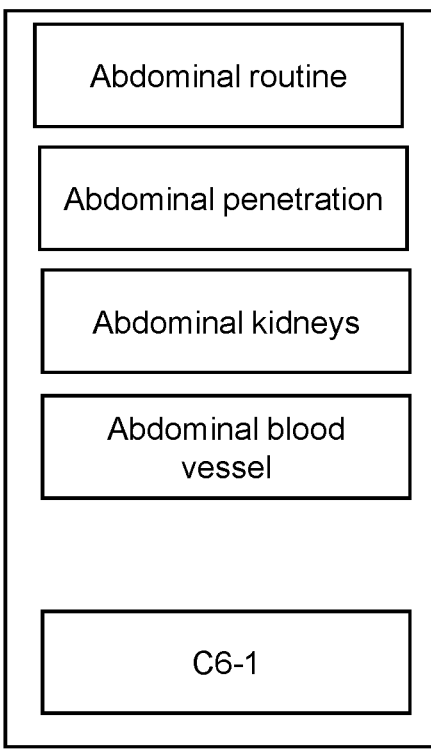
FIG. 18 is a schematic diagram illustrating another exemplary function control according to some embodiments of the present disclosure.

In some embodiments, the target configuration may include function controls corresponding to functions of different function modules under the target examination task. The function controls corresponding to the functions of different function modules under the target examination task may be determined based on the operator needs or actual situations. For example, as shown in FIG. 17, under a certain ultrasound examination, the operator still has a need to switch the probe switching module and the preset scanning parameter module. A combination switch bar of the probe and preset parameter may bind the probe and preset parameter that need to be switched together (e.g., uC 6-1 and uC 6-2 under a mid to late pregnancy examination), and the operator may perform a selection operation (e.g., the click operation) on the combination switch bar of the probe and the preset parameter, thus achieving an overall switch between the probe and the preset parameter. As another example, as shown in FIG. 18, a separate switch bar for the probe and the preset parameter may be displayed on the workbench interface. Under a certain ultrasound examination task, the user may switch the probe by an operation of selecting the probe; when determining the probe, the workbench interface may display a corresponding preset parameter for the probe, and the operator may switch the preset parameter by the operation of selecting the probe. Specifically, when determining the probe, the processing device may highlight a preset parameter for the probe (e.g., C6-1) by default, i.e., the preset parameter may be determined by default.

In some embodiments, the arrangement of multiple examination tasks may be arranged according to a sequence of performing the examination tasks.

Figure 14:
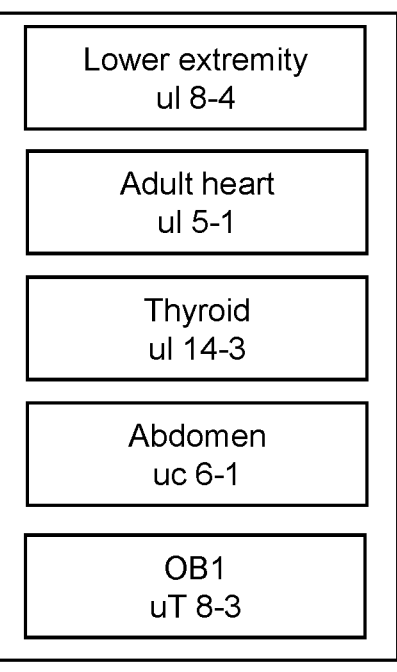
FIG. 14 is a schematic diagram illustrating an exemplary navigation region according to some embodiments of the present disclosure.

In some embodiments, the multiple examination tasks may be displayed in the taskbar, and the sequence of the multiple examination tasks in the taskbar may be updated in real-time. The sequence of the multiple examination tasks may be arranged according to the sequence of performing the examination tasks. As shown in FIG. 14, the current target examination task (e.g., lower limb blood vessels) may be located at a top (i.e., first) of the task bar and highlighted to indicate that the target examination tasks is being performed. The previous examination tasks (e.g., adult heart) may be located in a second section of the taskbar. By analogy, the sequence of the multiple examination tasks (thyroid, abdomen, OB1, etc.) may be arranged.

In some embodiments of the present disclosure, the taskbar may include multiple examination tasks, and the multiple examination tasks may be arranged according to the sequence of performing the examination tasks. The frequently performed examination tasks may be located at the front of the taskbar, making it easy for the operator to select and switch. In addition, the operator may switch between examination tasks by selecting the multiple examination tasks in the taskbar, which can improve the efficiency of performing the ultrasound examination.

In some embodiments of the present disclosure, the taskbar may include multiple examinations, and the multiple examinations may be arranged according to the sequence of performing the examinations. This way, the frequently performed examinations may be located at the front of the taskbar, making it easy for the operator to select and switch. In addition, the operator may switch between examinations by selecting the multiple examinations in the taskbar, which can improve the efficiency of performing the ultrasound examination.

In some embodiments of the present disclosure, by implementing the one or more functions through the controls, the operator can implement functions in different function modules on the workbench interface, which can reduce the need for page switching and making it convenient for the operator to use.

Figure 16:
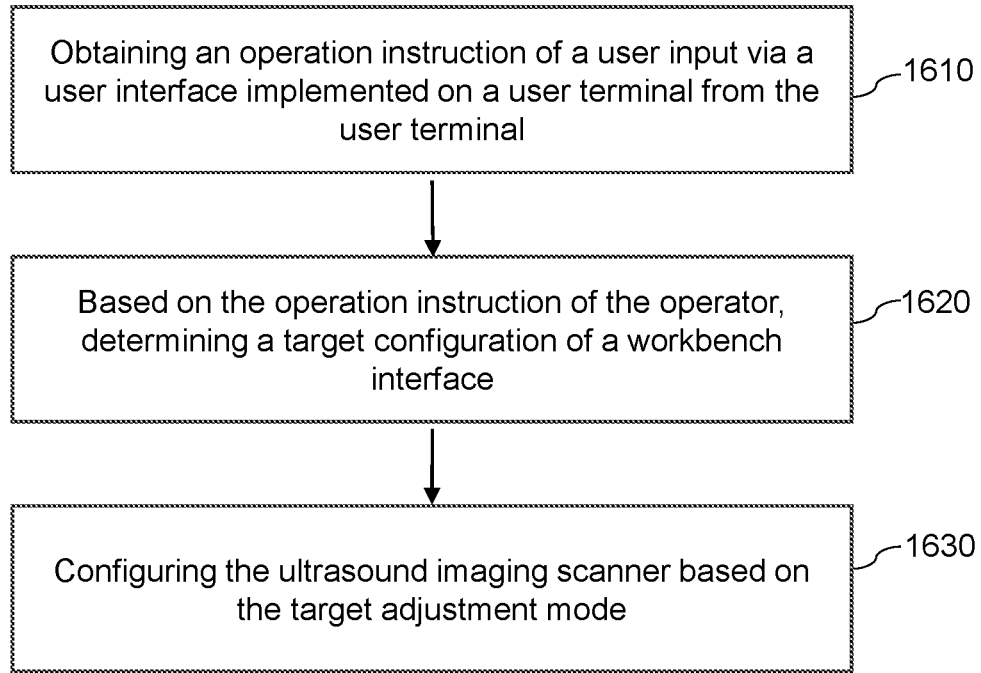
FIG. 16 is a flowchart illustrating an exemplary process of configurating an ultrasound imaging system according to some embodiments of the present disclosure.

FIG. 16 is a flowchart illustrating an exemplary process of configurating an ultrasound imaging system according to some embodiments of the present disclosure. In some embodiments, the process 1600 may be executed by a processing device. As shown in FIG. 16, the process 1600 may include the following operations:

In 1610, an operation instruction of a user input via a user interface implemented on a user terminal may be obtained from the user terminal.

In some embodiments, the operation instruction may be configured to configure a workbench interface. More descriptions of the user terminal and the user interface may be found in FIG. 1 and related descriptions. More descriptions of the instruction operation and the obtaining the instruction operation may be found in FIG. 3, FIG. 10. FIG.

11, and related descriptions. More descriptions of the workbench interface may be found in FIG. 10-FIG. 12 and related descriptions.

In 1620, based on the operation instruction of the operator, a target configuration of a workbench interface may be determined.

In some embodiments, the workbench interface may be configured to represent one or more function modules of each of different function modules of the ultrasound imaging scanner e. The target configuration may include one or more functions of each of the different function modules of the ultrasound imaging scanner.

In some embodiments, the processing device may display a first operation interface representing the workbench selection interface, and determine the workbench interface based on one of multiple first controls selected by the operator through the first operation interface. More descriptions regarding the first operation interface may be found in FIG. 12 and related descriptions.

In some embodiments, in response to receiving the operation instruction of the operator, the processing device may display a second operation interface representing the workbench interface configuration; and determine the target configuration of the workbench interface based on the operator input through the second operation interface. More descriptions regarding the second operation interface may be found in FIG. 12 and related descriptions.

In some embodiments, the processing device may determine the operator inputs on the second operation interface as a target configuration of the workbench interface.

In some embodiments, the operator may determine the target configuration based on the second operation interface, which can make the target configuration more in line with the usage habits, thereby improving the efficiency of performing the ultrasound examination based on the workbench interface.

In some embodiments, the second operation interface may include multiple candidate configurations of the workbench interface, and the processing device may determine the workbench interface based on one of the multiple candidate configurations selected by the operator through the second operation interface. More descriptions regarding the second operation interface may be found in FIG. 12 and related descriptions.

In some embodiments of the present disclosure, the operator may directly select a target configuration from multiple candidate configurations on the second operation interface, which improves the practicality of the workbench interface and eliminates the need for the operators to set the target configurations by themselves, thereby improving the efficiency of performing the ultrasound examination.

In some embodiments, different scanning modes may correspond to different target configurations of the workbench interface, more descriptions may be found in FIG. 10 and related descriptions.

In some embodiments, the processing device may obtain an image obtained by the ultrasound imaging scanner and update the target configuration of the workbench interface based on the image.

In some embodiments, the processing device may obtain the image obtained by the ultrasound imaging scanner based on network interruption or in real-time, and the ultrasound image may be displayed on the workbench interface.

In some embodiments, the processing device may identify, analyze, and process the image to obtain various feature information of the image, which can indirectly represent relevant parameters when obtaining the image. The processing device may update and process the relevant parameters or function controls on the workbench interface based on the identified information. For example, the processing device may determine a quality of the image and update the target configuration based on the quality of image, and the updated target configuration may be used to cause the quality of subsequent images obtained based on the updated target configuration satisfies a condition. As another example, the processing device may obtain a diagnostic result based on the image and update the target configuration based on the diagnostic result. The updated target configuration may be adapted to acquire subsequent images that are used for further diagnostic related to the diagnostic result. For example, the updated target configuration may be adapted to acquire subsequent images of another ROI associated with an ROI in the diagnostic result.

In some embodiments of the present disclosure, by updating the target configuration of the workbench interface based on the obtained images through the processing device, various function controls or related parameters of the workbench interface can be more in line with practical applications, and more accurate images can be obtained by performing the ultrasound examination, thereby making the ultrasound examination process more practical and reliable.

In 1630, the ultrasound imaging scanner may be configured based on the target adjustment mode, more description may be found in FIG. 3 and related descriptions.

In some embodiments of the present disclosure, by configuring the ultrasound imaging scanner through the target configuration, the workbench interface can be more adapted to different examination processes and user needs, breaking through the limitations between various function modules. The operator can complete various functions on the workbench interface, which can effectively reduce the count of times the operator switching the pages, reduce the average scanning time, and improve the scanning efficiency.

In some embodiments, the processing device may obtain information associated with at least one of the historical operations of the operators, clinical scenes, scanning subjects, or scanning modes for the scanning subjects, and determine the target configuration of the workbench interface based on information associated with at least one of the historical operations of the operators, clinical scenes, scanning subjects, or scanning modes for the scanning subjects, and configure the ultrasound imaging scanner based on target configuration.

In some embodiments, the processing device may obtain at least one associated information of the operators, the historical operations of the operators, clinical scenes, scanning subjects, or scanning modes for the scanning subjects from the storage device and/or ultrasound imaging scanner through the network. More descriptions of the operators and the ultrasound imaging scanner may be found in FIG. 1 and related descriptions, more descriptions of the operators and the historical operations of the operators may be found in FIG. 10 and related descriptions, more descriptions of the clinical scenes, scanning subjects, and the scanning modes for the scanning subjects may be found in FIG. 3, FIG. 10, and related descriptions.

FIG. 23 is a flowchart illustrating an exemplary process for ultrasound examination according to some embodiments of the present disclosure. In some embodiments, the process 2300 may be executed by a processing device. As shown in FIG. 23, the process 2300 may include the following operations:

In 2310, in response to receiving an operation instruction from a user terminal, the first operation interface may be displayed. The first operation interface may include multiple first controls, each of the multiple first controls may correspond to different ultrasound examinations, more descriptions may be found in FIG. 12, FIG. 13, and related descriptions.

In 2320, in response to receiving an operation of selecting the first control on the first operation interface from the operator, the workbench interface may be displayed. The workbench interface may include function controls corresponding to the multiple functions required for the ultrasound examination, more descriptions may be found in FIG. 12 and related descriptions.

In 2330, in response to receiving an operation of triggering the at least one function control from the operator, the ultrasound examination may be performed, more descriptions may be found in FIG. 12 and related descriptions.

In 2340, in response to receiving an operation of triggering the control of the second operation interface from the operator, the second operation interface may be displayed. The second operation interface may include multiple workbench interface layout modes, more descriptions may be found in FIG. 12 and related descriptions.

In 2350, in response to receiving an operation of selecting the target configuration of the multiple workbench interfaces, a target workbench interface may be updated according to the target configuration, more descriptions may be found in FIG. 12 and related descriptions.

In 2360, in response to receiving an operation of triggering the control of the virtual keyboard, the virtual keyboard may be displayed on the workbench interface, more descriptions may be found in FIG. 12 and related descriptions.

In 2370, in response to receiving an operation of modifying the operation instruction of the configuration from the operator, the function control on the workbench interface may be controlled to be in an updatable state, more descriptions may be found in FIG. 12 and related descriptions.

In 2380, in response to receiving an operation of controlling the function control on the workbench interface to be in an updatable state, the function control may be updated, more descriptions may be found in FIG. 12 and related descriptions.

Figure 24:
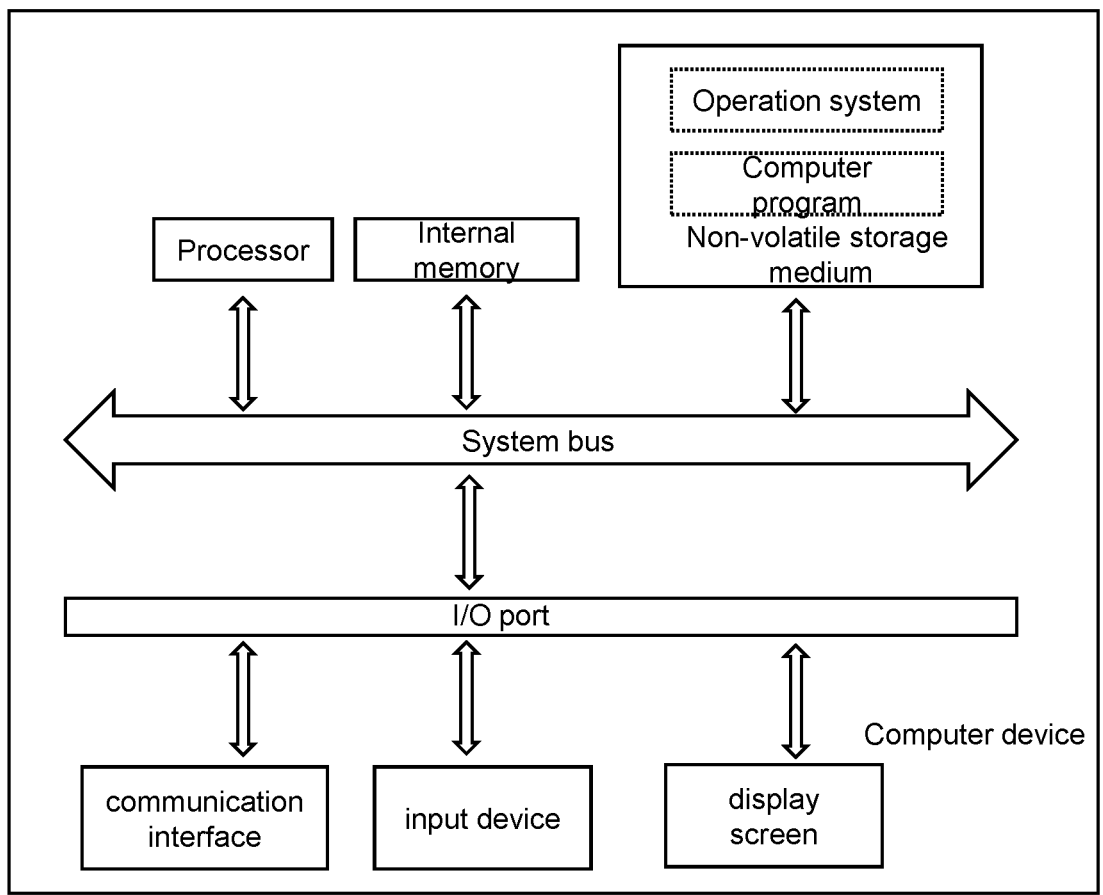
FIG. 24 is a schematic diagram illustrating an exemplary structure of an ultrasound host according to some embodiments of the present disclosure.

FIG. 24 is a schematic diagram illustrating an exemplary structure of an ultrasound host according to some embodiments of the present disclosure.

The ultrasound host may be a component of the ultrasound imaging scanner. The ultrasound host may be configured to receive the ultrasound examination instruction, and based on the ultrasound examination instruction, an ultrasound probe may be configured to emit ultrasound waves to the scanning subject. The ultrasound host may be a computer device. The computer device may include but are not limited to industrial computers, laptops, tablets, or the like. An internal structure diagram of the computer device is shown in FIG. 23. The computer device may include a processing device, memory, communication interface, display screen, and input device connected through a system bus. The processing device of the computer device may provide computing and control capabilities. The memory of the computer device may include a non-volatile storage media and a memory storage. The non-volatile storage medium may store an operation system and a computer program. The memory storage may provide an environment for the operation of the operation system and computer program on non-volatile storage media. The communication interface of the computer device may be used for wired or wireless communication with external terminals. The wireless process may be implemented through WIFI, mobile cellular networks, NFC (Near Field Communication), or other technologies. The computer program may be executed by the processing device to implement the ultrasound examination process. The display screen of the computer device may be a liquid crystal display screen or an electronic ink display screen. The input device of the computer device may be a touch layer covered on the display screen, a button, a trackball, a touchpad set on the computer device shell, an external keyboard, a touchpad, a mouse, or the like. The I/O interface may be a hardware circuit designed to process, initialize, and move data within semiconductor chips. The I/O interface may provide one or more interfaces to facilitate communication between the computer devices. The display unit may be configured to form a visually visible image, which can be a display screen, projection device, or virtual reality imaging device.

More descriptions of the ultrasound imaging scanner may be found in FIG. 1 and related descriptions.

The basic concepts have been described. Obviously, for those skilled in the art, the detailed disclosure may be only an example and may not constitute a limitation to the present disclosure. Although not explicitly stated here, those skilled in the art may make various modifications, improvements, and amendments to the present disclosure. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of the specification are not necessarily all referring to the same embodiment. In addition, some features, structures, or features in the present disclosure of one or more embodiments may be appropriately combined.

Moreover, unless otherwise specified in the claims, the sequence of the processing elements and sequences of the present application, the use of digital letters, or other names are not used to define the order of the application flow and methods. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various assemblies described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure and aiding in the understanding of one or more of the various embodiments. However, this disclosure may not mean that the present disclosure subject requires more features than the features mentioned in the claims. In fact, the features of the embodiments are less than all of the features of the individual embodiments disclosed above.

In some embodiments, the numbers expressing quantities, properties, and so forth, used to describe and claim certain embodiments of the application are to be understood as being modified in some instances by the term "about," "approximate," or "substantially." Unless otherwise stated, "about," "approximate," or "substantially" may indicate a ±20% variation of the value it describes. Accordingly, in some embodiments, the numerical parameters set forth in the description and attached claims are approximations that may vary depending upon the desired properties sought to be obtained by a particular embodiment. In some embodiments, the numerical parameters should be construed in light of the number of reported significant digits and by applying ordinary rounding techniques. Although the numerical domains and parameters used in the present application are used to confirm the range of ranges, the settings of this type are as accurate in the feasible range in the feasible range in the specific embodiments.

Each patent, patent application, patent application publication, and other materials cited herein, such as articles, books, instructions, publications, documents, etc., are hereby incorporated by reference in the entirety. In addition to the application history documents that are inconsistent or conflicting with the contents of the present disclosure, the documents that may limit the widest range of the claim of the present disclosure (currently or later attached to this application) are excluded from the present disclosure. It should be noted that if the description, definition, and/or terms used in the appended application of the present disclosure is inconsistent or conflicting with the content described in the present disclosure, the use of the description, definition and/or terms of the present disclosure shall prevail.

At last, it should be understood that the embodiments described in the disclosure are used only to illustrate the principles of the embodiments of this application. Other modifications may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A system, comprising:

at least one storage medium including a set of instructions;

at least one processor in communication with the at least one storage medium, wherein when executing the set of instructions, the at least one processor is directed to cause the system to perform operations including:

obtaining feature information of each of at least a portion of multiple scanning parameters, the feature information of each of the at least the portion of the multiple scanning parameters including a count of adjustment levels of the scanning parameter and an adjustment frequency of the scanning parameter, wherein each of the adjustment levels of the scanning parameter refers to a degree, a value, a range, or a state that the scanning parameter is able to be adjusted to, the adjustment frequency of the scanning parameter indicates a count or times of the scanning parameter that has been adjusted in ultrasound examinations over a certain period of time;

automatically determining a target configuration of an adjustment mode of each of at least a portion of the multiple scanning parameters based on the feature information of each of at least a portion of the multiple scanning parameters, wherein the target configuration of the adjustment mode of the scanning parameter includes a type and an arrangement of the adjustment mode on a user interface, the type of the adjustment mode of the scanning parameter includes a probe-based adjustment mode, an adjustment mode implemented on a control panel of an ultrasound imaging scanner, an adjustment mode implemented on a touch screen of the ultrasound imaging scanner, an eye interaction-based adjustment mode, or a gesture-based adjustment mode, the arrangement of the adjustment mode includes a distribution position of the adjustment mode on a component of the user interface; and configuring an ultrasound imaging device based on the target configuration.

2. The system of claim 1, wherein the operations further include:

providing one or more candidate configurations of the adjustment mode of a scanning parameter based on feature information of the scanning parameter; and sending the one or more candidate configurations of the adjustment mode to a user terminal of an operator of the ultrasound imaging device, wherein the target configuration is determined based on the one or more candidate configurations according to an operation instruction of the operator.

3. The system of claim 2, wherein the type of adjustment mode of each of the one or more candidate configurations include a probe-based adjustment mode in response to determining, by a processing device, that the adjustment frequency of the scanning parameter is greater than a first frequency threshold, and an adjustment mode implemented on a control panel-based adjustment mode in response to determining, by the processing device, that the adjustment frequency of the scanning parameter is smaller than the first frequency threshold and greater than a second frequency threshold.

4. The system of claim 1, wherein the adjustment mode using the adjustment control on the touch screen of the ultrasound imaging device includes using one of an excitation type adjustment control, a switch type adjustment control, a tile type adjustment control, a gear adjustment control, and a sliding type adjustment control;

the adjustment mode including using the excitation type adjustment control or the switch type adjustment control in response to determining that the count of the adjustment levels of the scanning parameter is less than a first count threshold, and the excitation type adjustment control or the switch type adjustment control activating or turning off a corresponding function of the scanning parameter by clicking or other operations; or the adjustment mode including using the tile type adjustment control in response to determining that the count of the adjustment levels of the scanning parameter exceeds the first count threshold and is less than a second count threshold, and the tile type adjustment control displaying options in tile types; or the adjustment mode including using the gear adjustment control in response to determining that the count of the adjustment levels of the scanning parameter exceeds the second count threshold and is less than a third count threshold, and the gear adjustment control being used to increase or decrease the scanning parameter; or the adjustment mode including using the sliding type adjustment control in response to determining that the count of the adjustment levels of the scanning parameter exceeds the third count threshold.

5. The system of claim 1, wherein a same entity is used to adjust the multiple scanning parameters in different adjustment modes, and the different adjustment modes including a B mode, a C mode, and a PW mode.

6. The system of claim 1, wherein an adjustment control of a scanning parameter with an adjustment frequency greater than a frequency threshold and a count of adjustment levels greater than a quantity threshold is displayed on a homepage and/or a target position of a parameter adjustment region in a target mode, and the target position is a position on a display interface.

7. The system of claim 1, wherein the operations further include:

classifying the at least a portion of the multiple scanning parameters into one or more groups based on the feature information of each of the multiple scanning parameters;

determining the target configuration based on the feature information of scanning parameters in a same group, wherein the one or more groups includes at least one of a first group, a second group, a third group, or a fourth group, the first group including scanning parameters including a depth, a dynamic range, a scale, and a gain, the second group including scanning parameters including a freezing, an image storage, a measuring, a harmonic, a frame rate, and a frame frequency, the third group including scanning parameters including an automatic optimization, a spatial composition, a fusion imaging, and a layout, and the fourth group including scanning parameters including a gray scale chart and a time gain compensation (TGC);

an adjustment frequency of each scanning parameter in the first group exceeds a frequency threshold and an adjustment level of each scanning parameter in the first group exceeds a count threshold, the type of the adjustment mode for a scanning parameter in the first group includes an adjustment mode using a knob implemented on the control panel of the ultrasound imaging device;

an adjustment frequency of each scanning parameter in the second group exceeds the frequency threshold and an adjustment level of each scanning parameter in the second group is less than the count threshold, the type of the adjustment mode for a scanning parameter in the second group includes an adjustment mode using a key implemented on the control panel of the ultrasound imaging device;

an adjustment frequency of each scanning parameter in the third group is less than the frequency threshold and an adjustment level of each scanning parameter in the third group is less than the count threshold, the type of the adjustment mode for the scanning parameter in the third group includes an adjustment mode using an excitation type adjustment control or a switch type adjustment control implemented on the touch screen of the ultrasound imaging device;

an adjustment frequency of each scanning parameter in the fourth group is less than the frequency threshold and an adjustment level of each scanning parameter in the fourth group exceeds the count threshold, the type of the adjustment mode for the scanning parameter in the fourth group includes an adjustment mode using a tile type adjustment control, a gear adjustment control, or a sliding type adjustment control implemented on the touch screen of the ultrasound imaging device.

8. A system, comprising:

at least one storage medium including a set of instructions;

at least one processor in communication with the at least one storage medium, wherein when executing the set of instructions, the at least one processor is directed to cause the system to perform operations including:

obtaining, from a user terminal, an operation instruction of an operator input via a user interface implemented on the user terminal, the operation instruction being for configuring an adjustment mode of a scanning parameter of an ultrasound imaging device;

automatically determining, based on the operation instruction of the operator, a target configuration of the adjustment mode of the scanning parameter, wherein the target configuration of the adjustment mode of the scanning parameter includes a type and an arrangement of the adjustment mode on the user interface, the type of the adjustment mode of the scanning parameter includes a probe-based adjustment mode, an adjustment mode implemented on a control panel of the ultrasound imaging scanner, an adjustment mode implemented on a touch screen of the ultrasound imaging scanner, an eye interaction-based adjustment mode, and a gesture-based adjustment mode, the arrangement of the adjustment mode includes a distribution position of the adjustment mode on a component of the ultrasound imaging scanner or system; and configuring the ultrasound imaging device based on the target configuration.

9. A system, comprising:

an ultrasound imaging device; and a user terminal in communication with the ultrasound imaging device, the user terminal including a user interface implemented on a touch screen, the user interface representing one of a workbench interface in a target configuration or a function module interface in response to receipt of an operation instruction for entering inputted by an operator, wherein the target configuration of the workbench interface includes one or more functions of each of different function modules of the ultrasound imaging device, the workbench interface is configured to facilitate an interaction between the operator and an ultrasound imaging scanner to cause or facilitate the ultrasound imaging scanner to perform one or more functions from each of different function modules, the workbench interface includes an integration of functions from the different function modules, the workbench interface includes an integration of functions from a clinic scene switch module, a probe switching module, a scanning parameter adjustment module, and a measurement module, the function module interface is configured to facilitate an interaction between the operator and the ultrasound imaging scanner to cause or facilitate a function module corresponding to the function module interface to perform one or more functions of the function module.

10. The system of claim 9, wherein the target configuration includes one or more types of the one or more functions of each of different function modules of the ultrasound imaging device and/or an arrangement of the one or more functions in the workbench interface.

11. The system of claim 9, wherein the system further includes:

at least one storage medium including a set of instructions;

at least one processor in communication with the at least one storage medium, wherein when executing the set of instructions, the at least one processor is directed to cause the system to perform operations including:

determining one or more candidate configurations of the workbench interface, each of the one or more candidate configurations including one or more candidate functions and/or a candidate arrangement of the one or more candidate functions on the workbench interface, wherein the one or more candidate configurations are determined based on at least one of operators, historical operations of the operators, clinical scenes, scanning subjects, or scanning modes for the scanning subjects; and providing the one or more candidate configurations to the user interface, wherein the target configuration is determined based on the one or more candidate configurations; wherein the user interface represents a parameter adjustment interface, the parameter adjustment interface includes a mode display region, a mode switch region, and a parameter adjustment region; the mode display region is configured to display a switchable mode supported by the ultrasound imaging scanner, the switchable mode includes a contrast, a B mode, a C mode, a CW mode, or a PW mode, the mode switch region is configured to display an entrance of other modes allowed to enter in a current scanning mode, and the parameter adjustment region is configured to display the scanning parameter that are allowed to be adjusted in the current scanning mode corresponding to the mode display region.

12. The system of claim 11, wherein the operations further include:

in response to receiving an operation instruction for a workbench interface configuration from the operator, displaying the one or more candidate configurations; and in response to receiving an operation instruction for configuration selection from the operator, determining the target configuration from the one or more candidate configurations, the target configuration is a selected candidate configuration or determined by modifying the selected candidate configuration of the operator according to an operation instruction for configuration modification from the operator.

13. The system of claim 9, wherein different clinical scenes, or different scanning subjects, or different scanning modes for the scanning subjects correspond to different target configurations.

14. The system of claim 9, wherein the workbench interface includes a navigation region and a control display region, the navigation region is configured to display labels of the different function modules, and the control display region is configured to display a control of each function from the different function modules.

15. The system of claim 9, wherein the workbench interface includes a control configured to trigger a first operation interface for workbench interface selection to be entered, the first operation interface including multiple first controls, each of the multiple first controls corresponding to one of multiple workbench interfaces, each of the multiple workbench interfaces corresponding to one of multiple examination tasks.

16. The system of claim 9, wherein the workbench interface includes a control configured to trigger a second operation interface for workbench interface configuration to be entered, the second operation interface provides multiple candidate configurations of the workbench interface and/or the workbench interface includes a control configured to trigger a third operation interface representing a virtual keyboard to be entered.

17. The system of claim 14, wherein the control display region includes multiple controls for selecting scanning modes, the target configuration includes function controls correspond to the one or more functions of each of the different functions modules under a target scanning mode, and the scanning modes refer to a scanning mode used by the ultrasound imaging scanner for the ultrasound examination, and the scanning modes include a contrast, a B mode, a C mode, a CW mode, and a PW mode.

18. The system of claim 9, wherein the workbench interface includes a taskbar, and the taskbar includes multiple examination items and the target configuration includes function controls corresponding to the one or more functions of each of different functions modules under a target examination item and/or the workbench interface includes a taskbar, and the taskbar includes multiple examination tasks and the target configuration includes function controls corresponding to the one or more functions of each of different functions modules under a target examination task.

19. The system of claim 9, wherein the different function modules of the ultrasound imaging device incudes a parameter adjustment module, and the one or more functions includes a parameter adjustment function of multiple scanning parameters, the workbench interface includes a parameter adjustment region including multiple adjustment controls of the multiple scanning parameters, each of the multiple adjustment controls indicating a target adjustment mode of a scanning parameter.

20. The system of claim 9, wherein the user interface is configured to switch between the function module interface for a parameter adjustment function and the workbench interface, the function module interface for the parameter adjustment function represents adjustment modes of multiple scanning parameters, an adjustment mode of one of the multiple scanning parameters is in a target configuration determined based on feature information of the scanning parameter.

* * * * *